(12) United States Patent
Winssinger et al.

(10) Patent No.: US 8,513,440 B2
(45) Date of Patent: Aug. 20, 2013

(54) COMPOSITIONS AND METHODS COMPRISING ANALOGUES OF RADICICOL A

(75) Inventors: Nicolas Winssinger, Strasbourg (FR); Sofia Barluenga, Strasbourg (FR)

(73) Assignees: Universite de Strasbourg, Strasbourg (FR); Centre National de la Recherche Scientifique, Paris (FR)

( * ) Notice: Subject to any disclaimer, the term of this patent is extended or adjusted under 35 U.S.C. 154(b) by 366 days.

(21) Appl. No.: 12/663,079

(22) PCT Filed: Jun. 5, 2008

(86) PCT No.: PCT/IB2008/002497
§ 371 (c)(1),
(2), (4) Date: May 24, 2010

(87) PCT Pub. No.: WO2008/149244
PCT Pub. Date: Dec. 11, 2008

(65) Prior Publication Data
US 2010/0233279 A1  Sep. 16, 2010

Related U.S. Application Data

(60) Provisional application No. 60/933,171, filed on Jun. 5, 2007.

(51) Int. Cl.
*C07D 493/00* (2006.01)
(52) U.S. Cl.
USPC .......................................................... 549/270
(58) Field of Classification Search
USPC .......................................................... 549/270
See application file for complete search history.

(56) References Cited

FOREIGN PATENT DOCUMENTS

| | | |
|---|---|---|
| JP | 2004292315 | 10/2004 |
| WO | WO-02/16369 A2 | 2/2002 |
| WO | WO-03/076424 A1 | 9/2003 |
| WO | WO 03076424 * | 9/2003 |
| WO | WO-2006/036941 A2 | 4/2006 |

OTHER PUBLICATIONS

Winssinger et al. Chem. Commun., 2007, 22-36.*

* cited by examiner

*Primary Examiner* — Nizal Chandrakumar
(74) *Attorney, Agent, or Firm* — Saliwanchik, Lloyd & Eisenschenk

(57) ABSTRACT

Disclosed are novel analogues of the natural product radicicol A of formulae I, .Ia, pi, Ha, lib and HI, pharmaceutical compositions comprising the compounds. The compounds of the invention are kinase and phosphatase inhibitors and find utility in the treatment or prevention of kinase and phosphatase-mediated disorders. Also provided are uses and methods for the treatment or prevention of kinase- and phosphatase-mediated disorders and synthetic processes for the preparation of the compounds.

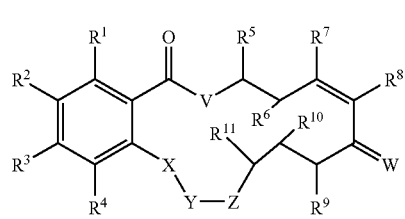

(I)

16 Claims, 2 Drawing Sheets

COMPOSITIONS AND METHODS COMPRISING ANALOGUES OF RADICICOL A

CROSS REFERENCE TO RELATED APPLICATIONS

This application is a 35 U.S.C. 371 national phase patent application and claims priority to International Patent Application Number PCT/IB2008/002497, filed Jun. 5, 2008, and entitled "Compositions And Methods Comprising Analogues Of Radicicol A," which claims priority to U.S. Provisional Patent Application No. 60/933,171, filed Jun. 5, 2007, which are hereby incorporated by reference in their entirety.

FIELD OF THE INVENTION

The present invention is directed to novel derivatives, analogues and intermediates of the natural product radicicol A and related resorcylic acid lactones, and to their syntheses. The present invention is further directed to use of these compounds, which are potent inhibitors of kinases and phosphatases, including ATPases, for the treatment or prevention of disorders that are mediated by kinases or phosphatases.

BACKGROUND OF THE INVENTION

Protein kinases mediate intracellular signal transduction by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell. Examples of such stimuli include environmental and chemical stress signals (e.g. osmotic shock, heat shock, ultraviolet radiation, bacterial endotoxin, $H_2O_2$), cytokines (e.g. interleukin-1 (IL-1) and tumor necrosis factor alpha (TNF-alpha)), and growth factors (e.g. granulocyte macrophage-colony-stimulating factor (GM-CSF), and fibroblast growth factor (FGF). An extracellular stimulus may effect one or more cellular responses related to cell growth, migration, differentiation, secretion of hormones, activation of transcription factors, muscle contraction, glucose metabolism, control of protein synthesis and regulation of cell cycle.

Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

Thus, selective kinase and phosphatase inhibitors have emerged as important drug targets, and inhibition of kinase phosphorylation activity is one of the most promising strategies for chemotherapy. Multiple small molecule kinase inhibitor drugs are already approved: Gleevec, which inhibits Abl, and Iressa and Tarceva, which both inhibit EGFR, Sorafenib (Nexavar, BAY 43-9006) which inhibits Raf, Dasatinib (BMS-354825) and Nilotinib (AMN-107, Tasigna) which also inhibits Abl, Lapatinib which also inhibits EGFR, Temsirolimus (Torisel, CCI-779) which targets the mTOR pathway, Sunitinib (Stuten, SU11248) which inhibits several targets including VGFR as well as specific antibodies inactivating kinase receptors: Herceptin and Avastin

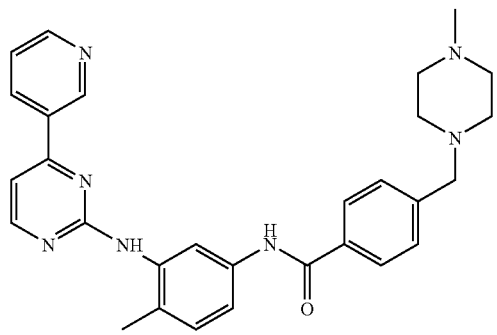

Gleevec (imatinib) - STI 571
inhibitor of the Abelson kinase;
approved for chronic myelogenous leukemia

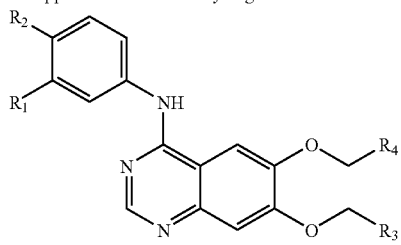

Tarceva (erlotinib) - OSI774
R1 = CCH; R2 = H; R3 = R4 = $CH_2OCH_3$

Iressa (gefitinib) - ZD1839
R1 = Cl; R2 = F; R3 = H; R4 = 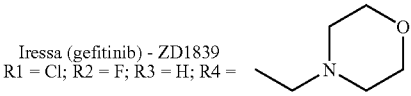

inhibitors of epidermal growth factor receptor (EGFR);
approved for lung cancer

Some resorcylic acid macrolides had been known as kinase or phosphatase inhibitors (U.S. Pat. Nos. 5,674,892; 5,728,726; 5,731,343; and 5,795,910; all of which are hereby incorporated by reference in their entirety), or to inhibit other enzymes (U.S. Pat. No. 5,710,174, which is hereby incorporated by reference in its entirety, discloses inhibition of FXIIIa catalysis of fibrin cross-linking). Resorcylic acid macrolides were also employed for other medical indications (U.S. Pat. Nos. 3,453,367; 3,965,275; 4,035,504; 4,670,249; 4,778,821; 4,902,711; and 6,635,671; all incorporated by reference in their entirety).

Radicicol and the pochonins are resorcylic acid lactone natural products, and intermediates for synthesizing some of their analogues may be obtained by fermentation. However, relying only upon those natural products or their fermentation derivatives severely limits the range of compounds. Thus, a number of novel resorcylic acid macrolides have been synthesized. Many of these are zearalane and related compounds in which the macrocyclic ring contains no carbon-carbon double bond other than between carbons of the phenyl ring. (U.S. Pat. Nos. 3,373,038; 3,586,701; 3,621,036; 3,631,179; 3,687,982; 3,704,249; 3,751,431; 3,764,614; 3,810,918; 3,836,544; 3,852,307; 3,860,616; 3,901,921; 3,901,922; 3,903,115; 3,957,825; 4,042,602; 4,751,239; 4,849,447; and U.S. Publication No. 2005-0256183; all of which are incorporated herein by reference). Syntheses have also been reported for resorcylic acid macrolides characterized by one double bond between ring carbons outside the phenyl ring. (U.S. Pat. Nos. 3,196,019; 3,551,454; 3,758,511; 3,887,583; 3,925,423; 3,954,805; and 4,088,658; all of which are incorporated herein by reference). Most of those are 14-member macrocycles, but syntheses have also been reported for the 12-member macrocycle analogues. (U.S. Pat. Nos. 5,710,174; 6,617,348; and U.S. Publication No. 2004-0063778 and PCT Publication No. WO 02/48135; all of which are incorporated by reference in their entirety).

Syntheses have also been reported for radicicol-related compounds having two non-aromatic double bonds and either a halide or a 1,2-oxo group (i.e., an epoxide) on the macrocyclic ring. (U.S. Pat. Nos. 4,228,079; 5,597,846; 5,650,430; 5,977,165; 7,115,651; and Japanese Publication Nos. JP 6-279279A, JP 6-298764A, JP 9-202781A, JP 10-265381A2; and JP 2000-236984). Syntheses of oximes of radicicol-related compounds are disclosed in U.S. Pat. Nos. 5,977,165; 6,239,168; 6,316,491; 6,635,662; 2001-0027208; 2004-0053990; Japanese Publication No. JP 2003-113183A2; and PCT Publication No. WO 99/55689. Synthesis of cyclopropa-analogues of radicicol is disclosed in U.S. Pat. No. 7,115,651 and PCT Publication No. WO 05/061481. Syntheses of some other resorcylic acid macrolide analogues are disclosed in U.S. Publication No. 2006-0247448 and in PCT Publication No. WO 02/48135. Radicicol as well as Pochonins A and C have also been synthesized (S. Barluenga et al., *Angew. Chemie*, 43(26):3467-3470 (2004); S. Barluenga et al., *Chemistry—A European Journal*, 11(17):4935-4952 (Aug. 19, 2005); E. Moulin et al., et al., *Organic Letters*, 7(25):5637-5639 (Dec. 8, 2005).

Radicicol A (F87-25909.04, 1) shown below belongs to the family of resorcylic acid lactones (RAL) and was first reported by researchers from Sandoz who identified this fungal metabolite from a screen for IL1β inhibition (see published European Application No. EP 0606044 A1, which is incorporated herein by reference in its entirety, and N. Winssinger, S. Barluenga, *Chem Commit* (*Camb*) 2007, 22; T. Kastelic, J. Schnyder, A. Leutwiler, R. Traber, B. Streit, H. Niggli, A. Mackenzie, D. Cheneval, *Cytokine* 1996, 8, 751). While it was observed that this compound accelerated the degradation of specific mRNA sequences including IL1βs, its precise molecular target was not identified (D. Cheneval, P. Ramage, T. Kastelic, T. Szelestenyi, H. Niggli, R. Hemmig, M. Bachmann, A. Mackenzie, *Journal of Biological Chemistry* 1998, 273, 17846). Subsequently, two other related resorcylic acid lactones containing a cis-enone, compounds 3 and 5 below, were reported to be potent irreversible yet selective kinase inhibitors (J. Ninomiya-Tsuji, T. Kajino, K. Ono, T. Ohtomo, M. Matsumoto, M. Shiina, M. Mihara, M. Tsuchiya, K. Matsumoto, *Journal of Biological Chemistry* 2003, 278, 18485; A. Zhao, S. H. Lee, M. Mojena, R. G. Jenkins, D. R. Patrick, H. E. Huber, M. A. Goetz, O. D. Hensens, D. L. Zink, D. Vilella, A. W. Dombrowski, R. B. Lingham, L. Huang, *Journal of Antibiotics* 1999, 52, 1086). More recently, Santi and co-workers showed that hypothemycin, which also bears the cis-enone moiety, covalently inactivates ERK2 by reacting with a cysteine residue positioned in the active site, Cys166 (A. Schirmer, J. Kennedy, S. Murli, R. Reid, D. V. Santi, *Proc Natl Acad Sci USA* 2006, 103, 4234).

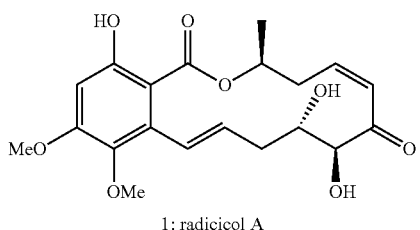

1: radicicol A

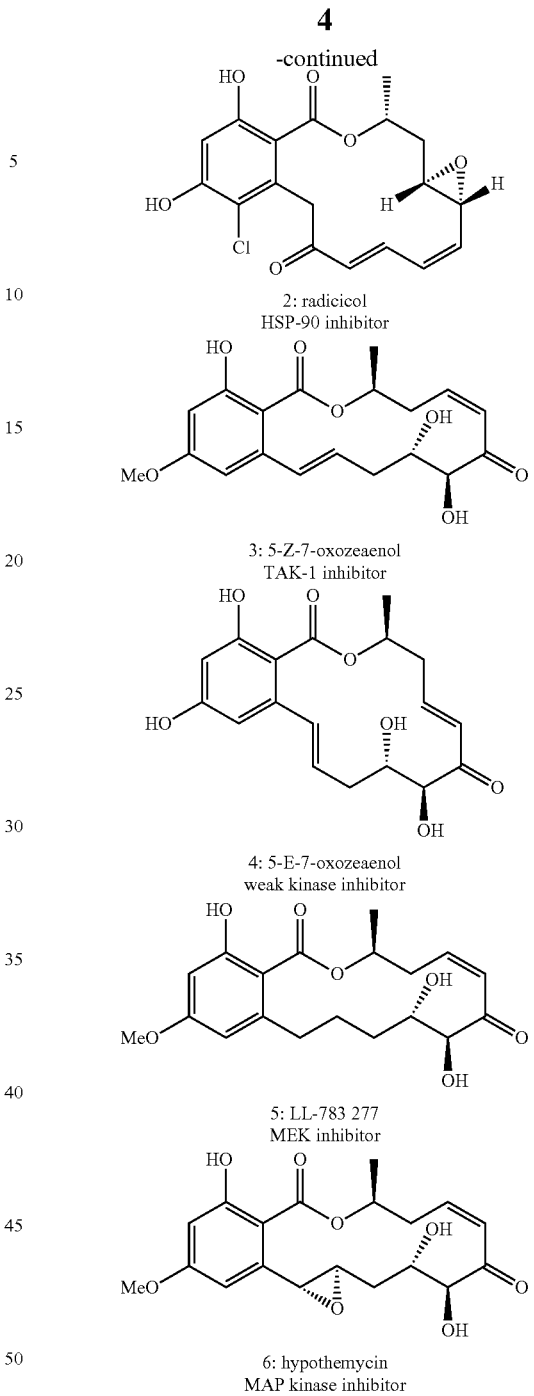

2: radicicol
HSP-90 inhibitor

3: 5-Z-7-oxozeaenol
TAK-1 inhibitor

4: 5-E-7-oxozeaenol
weak kinase inhibitor

5: LL-783 277
MEK inhibitor

6: hypothemycin
MAP kinase inhibitor

Published Japanese Patent Application No. JP 08040893 A discloses macrocycles containing a cis-enone group which are related to radicicol A as useful inhibitors of interleukin-1 (IL-1). The compounds are disclosed to be useful for the treatment of diseases caused by the overproduction of IL-1. Published U.S. Patent Application Nos. US2004/0224936 and 2006/0247448 and published International Application No. WO 03/076424, all which are hereby incorporated by reference in their entirety, describe analogues of radicicol A, which are potent kinase inhibitors and are disclosed to be useful in treating kinase-mediated diseases. Published International Patent Applications No. WO 02/48135, WO 02/48135, WO 2006/036941 and WO 02/48135 and British Patent Application No. GB 2323845 A, all incorporated herein by reference, disclose compounds and compositions related to radicicol A, which are disclosed to be kinase inhibitors.

Interest in the RALs stems from the observation that a significant fraction of the family of natural products has been shown to inhibit kinases and ATPases. Despite the lack of obvious similarities between the RALs and ATPases, these compounds have been shown to bind to the ATP-binding pocket of kinases and ATPase.

Despite the progress described above, chemical biologists continue to suffer from a limited ability to knock out specific kinase activity in order to deconvolute the role of specific kinases within complex signaling networks. Small molecules that can permeate cells have promise for solving this problem. And it has become increasingly apparent that the biological function of kinases is often regulated by their conformation, which is in turn dictated by their phosphorylation level and by intra- and inter-molecular associations. Small molecule inhibitors also have the potential to discriminate between different conformations of a given kinase; thus, small molecules offer a means to dissect the respective functions of those conformations.

Thus, there is an ongoing need for kinase inhibitors and ATPase inhibitors that have improved potency and selectivity. Moreover, the design and synthesis of such inhibitors and of targeted libraries of inhibitors remains challenging; thus, there is an ongoing need for improved synthetic methods.

SUMMARY OF THE INVENTION

Novel analogues of radicicol A and related resorcylic acid lactones (RAL), tautomers thereof, pharmaceutically acceptable salts, solvates, esters or prodrugs thereof, and pharmaceutical compositions comprising the compounds for the treatment of kinase-mediated or phosphatase-mediated disorders are provided. Also presented are methods for the treatment of kinase-mediated or phosphatase-mediated disorders using the compounds of the invention. Uses of the compounds in the treatment or prevention of kinase-mediated or phosphatase-mediated disorders and use of the compounds in the manufacture of a medicament for the treatment of a kinase-mediated or phosphatase-mediated disorder are provided. The compounds of the invention are active as kinase inhibitors and inhibitors of phosphatase, including ATPases. In addition, improved processes for the preparation of the compounds that are amenable to automated synthesis techniques are provided.

The compounds of the invention specifically exclude the compounds radicicol A (1), 5-Z-7-oxozeanol (3), hypothemycin (6), or LL-783,277 (5) or stereoisomers of these compounds.

In a first embodiment of the invention, a compound of formula I, a tautomer thereof, or a pharmaceutically acceptable salt, solvate, ester or prodrug thereof, is provided:

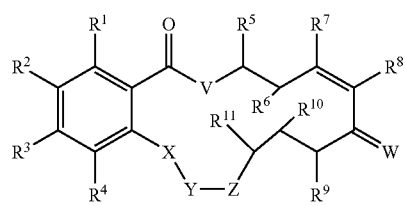

I wherein:

$R^1$, $R^2$, $R^3$ and $R^4$ are each independently hydrogen, halogen, cyano, —OR, —NRR$^X$, —NRS(O)R$^X$, —NRS(O)$_2$R$^X$, —SR, —S(O)R, —S(O)$_2$R, —OC(O)R, —C(O)R, —C(O)OR, —NRC(O)R$^X$, —C(O)NRR$^X$, —OC(O)OR, aliphatic, heteroaliphatic, acyl, aryl, heteroaryl, alkylaryl, arylalkyl, alkylheteroaryl or heteroarylalkyl;

$R^5$ and $R^6$ are each independently hydrogen, halogen, cyano, aliphatic, heteroaliphatic, aryl, heteroaryl, alkylaryl, arylalkyl, alkylheteroaryl, heteroarylalkyl, halogen or a leaving group;

$R^7$ and $R^8$ are each independently hydrogen, halogen, cyano, —OR, —NRR$^X$, —NRS(O)R$^X$, —NRS(O)$_2$R$^X$, —SR, —S(O)R, —S(O)$_2$R, —OC(O)R, —C(O)R, —C(O)OR, —NRC(O)R$^X$, —C(O)NRR$^X$, —OC(O)OR, aliphatic, heteroaliphatic, aryl, heteroaryl, alkylaryl, arylalkyl, alkylheteroaryl, heteroarylalkyl, or a leaving group;

$R^9$, $R^{10}$ and $R^{11}$ are each independently hydrogen, azide, —OR, —NRR$^X$, —NRS(O)R$^X$, —NRS(O)$_2$R$^X$, —SR, —S(O)R, —S(O)$_2$R, —OC(O)R, —C(O)R, —C(O)OR, —NRC(O)R$^X$, —C(O)NRR$^X$, —OC(O)OR, aliphatic, heteroaliphatic, aryl, heteroaryl, alkylaryl or alkylheteroaryl;

V is O, S or NR;

W is O, S, N—R, N—OR, N—NHS(O)$_2$R, N-acyl, or N—NH-acyl;

X and Y are independently CH$_2$, O, S or NR; or X and Y together represent —CHR—CHR—; cis- or trans —CR═CR$^X$—; —CH(OH)—CH(OH)—; —CH(halogen)-CH(OH); —CH(OH)—CH(halogen); or one of X and Y is O, S or NR and the other of X and Y is CH$_2$; or one of X or Y is N and the other of X or Y is ═CH; or X and Y together represent 1,2-cyclopropadiyl, or 1,2-oxirane; or X together with Y represent a covalent bond; or Y together with Z represent a covalent bond;

Z is CRR$^X$, ═CR—, O, S, ═N, NR or Z represents a covalent bond, or Z together with Y represent a covalent bond; and R and R$^X$ are independently hydrogen, aliphatic, heteroaliphatic, aryl, arylalkyl, alkylaryl, heteroaryl, alkylheteroaryl, heteroarylalkyl, acyl including acetyl, sulfonyl or a protecting group; with the proviso that when Z is a covalent bond, W is O and $R^6$ is lower alkyl, then $R^7$ is not hydrogen; and with the additional proviso that $R^7$ is not hydrogen when Z is a covalent bond; W is O; $R^4$ is hydrogen, OMe or —CO$_2$Me; X and Y together form trans —CH═CH— or —C(CH$_3$)═CH— or X and Y together form an epoxide ring or a cyclopropyl ring; and with the further proviso that when Z is a covalent bond; $R^5$ is methyl; $R^3$ is OH, C$_{1-4}$ alkoxy or C$_{1-4}$alkylCOO—; $R^4$ is H, OH, C$_{1-4}$ alkoxy or C$_{1-4}$alkylCOO—; V is O; W is O; X and Y together represent —CH$_2$—CH$_2$ or —CH═CH—; $R^9$ or $R^{10}$ are H, OH, C$_{1-4}$ alkoxy or C$_{1-4}$alkylCOO—; then $R^7$ or $R^8$ are not both hydrogen or $R^7$ or $R^8$ are not OH, C$_{1-4}$alkoxy or C$_{1-4}$alkylCOO—;

wherein aliphatic, aryl, heteroaryl, alkylaryl, arylalkyl, heteroarylalkyl or alkylheteroaryl are optionally substituted.

In another embodiment of the invention, a compound of formula Ia, a tautomer thereof, or a pharmaceutically acceptable salt, solvate, ester or prodrug thereof, is provided:

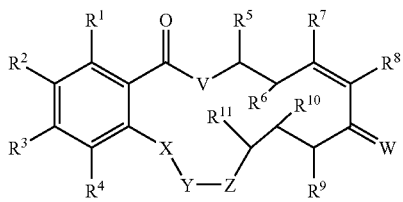

Ia wherein:

$R^1, R^2, R^3, R^4, R^5, R^6, R^7, R^8, V, W, R^9, R^{10}, R^{11}, Z, Y,$ and X are as defined for the compound of formula I; with the proviso that when $R^8$ is hydrogen or halogen, $R^7$ is not hydrogen, OH, $C_{1-4}$alkoxy, or $C_{1-4}$alkylCOO—.

In another embodiment of the invention, a compound of formula Ib, a tautomer thereof, or a pharmaceutically acceptable salt, solvate, ester or prodrug thereof, is provided:

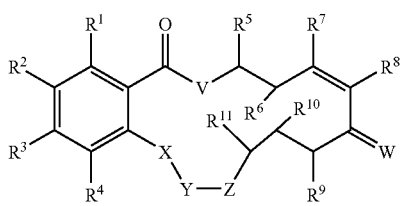

Ib wherein:

$R^1, R^2, R^3, R^4, R^5, R^6, R^7, R^8, V, W, R^9, R^{10}, R^{11}, Z, Y,$ and X are as defined for the compound of formula I; with the proviso that (1) when Z is a covalent bond, W is O and $R^6$ is lower alkyl, then $R^7$ is not hydrogen; and with the additional proviso that (2) $R^7$ is not hydrogen when Z is a covalent bond; W is O; $R^4$ is hydrogen, OMe or —CO$_2$Me; X and Y together form trans —CH═CH— or —C(CH$_3$)═CH— or X and Y together form an epoxide ring or a cyclopropyl ring; and with the further proviso (3) that when Z is a covalent bond; V is O; $R^5$ is methyl; $R^3$ is OH, $C_{1-4}$ alkoxy or $C_{1-4}$alkylCOO—; $R^4$ is H, OH, $C_{1-4}$ alkoxy or $C_{1-4}$alkylCOO—; V is O; W is O; X and Y together represent —CH$_2$—CH$_2$— or —CH═CH—; $R^9$ or $R^{10}$ are H, OH, $C_{1-4}$ alkoxy or $C_{1-4}$alkylCOO—; then $R^7$ or $R^8$ are not both hydrogen or $R^7$ or $R^8$ are not OH, $C_{1-4}$alkoxy or $C_{1-4}$alkylCOO—; and with the additional proviso (4) that when $R^1$ is OH or —O-lower acyl; $R^3$ is OH, lower alkoxy or —O-lower acyl; $R^4$ is H or halogen; $R^5$ is lower alkyl; $R^9$ and $R^{10}$ are OH; Z is a covalent bond; V is O; W is O; and X and Y together represent a trans- —CH═CH—; then $R^7$ is not hydrogen.

In one embodiment of formulae I, Ia or Ib, V is O. In another embodiment of formula I or Ia, V is S or NR.

In another embodiment, a compound of formula II is provided

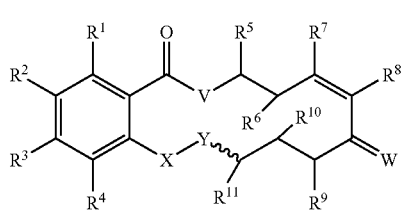

II wherein $R^1, R^2, R^3, R^4, R^5, R^6, R^7, R^8, W, R^9, R^{10}, R^{11}, X$ and Y are as defined for the compound of formula I.

In other embodiments, compounds of formulae I, Ia, Ib or II are provided, wherein X and Y together represent —CHR—CHR—; or cis- or trans —CR═CR$^x$—.

In other embodiments, the compound of formulae I, Ia, Ib or II are provided, wherein X and Y together represent —CHR—CHR—; or cis- or trans —CR═CR$^x$—.

In still another embodiment, a compound formula III is provided

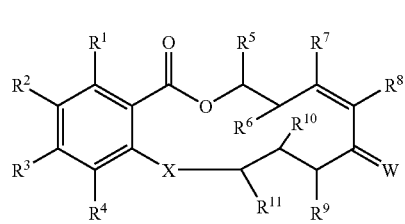

III wherein $R^1, R^2, R^3, R^4, R^5, R^6, R^7, R^8, W, R^9, R^{10}, R^{11}$ and X are as defined for the compound of formula I.

In some embodiments, compounds of formulae I, Ia, Ib, II or III are provided wherein X is O or CH$_2$.

In other embodiments, compounds of formulae I, Ia, Ib II or III are provided, wherein X is O or S.

In still other embodiments, compounds of formulae I, Ia, Ib or II are provided wherein Y is O or S.

In another embodiment of the invention, a compound of formula IIa is provided:

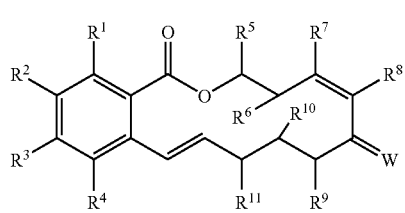

IIa wherein $R^1, R^2, R^3, R^4, R^5, R^6, R^7, R^8, W, R^9, R^{10}$ and $R^{11}$ are as defined for the compound of formula I.

In various embodiments, compounds of formulae I, Ia, Ib II, III or IIa are provided wherein W is O or S.

In other embodiments, compounds of formulae I, Ia, Ib, II, III or IIa are provided wherein W is N—R, N—OR, N—NHS(O)$_2$R, N-acyl or N—NH-acyl.

In various other embodiments of the invention, compounds of formulae I, Ia, Ib, II, III or IIa are provided wherein $R^{10}$ and $R^{11}$ are independently H, OH or NR.

In still other embodiments of the invention, compounds of formulae I, Ia, Ib, II, IIa, or III are provided wherein $R^1$ is OH; $R^3$ is OR, NR or halogen; and $R^4$ is H or halogen. In another embodiment of formulae I, Ia, Ib, II, IIa or II, $R^1$ is OH and $R^4$ is chloro. In still another embodiment, $R^1$ is OH and $R^4$ is hydrogen.

In still another embodiment, a compound of formula IIb is provided

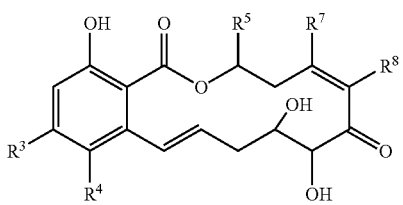

wherein $R^1$, $R^2$, $R^3$, $R^4$, $R^5$, $R^6$, $R^7$ and $R^8$ are as defined for the compound of formula I.

In various embodiments, compounds of formulae I, Ia, Ib, II, IIa, IIb or III are provided wherein $R^3$ is OR, NR or halogen; and $R^4$ is H or halogen. In another embodiment of formulae I, Ia, Ib, II, IIa, IIb or III, $R^3$ is OR and $R^4$ is chloro. In still another embodiment of formulae I, Ia, Ib, II, IIa, IIb or III, $R^3$ is OR and $R^4$ is hydrogen.

In other embodiments, compounds of formulae I, Ia, Ib, II, IIa, IIb or III are provided wherein $R^5$ is H or methyl, and $R^7$ is hydrogen, halogen or lower alkyl.

In other embodiments, compounds of formulae I, Ia, Ib, II, IIa, IIb or III are provided wherein $R^5$ is H or methyl, and $R^8$ is hydrogen, halogen or lower alkyl.

In still other embodiments, of formulae I, Ia, Ib, II, IIa, IIb or III are provided wherein $R^5$ is H or methyl, $R^7$ is lower alkyl, chloro or fluoro; and $R^8$ is hydrogen or fluoro.

In particular embodiments of the invention, specific compounds having the formulae shown in the Table 1 below are provided.

In another aspect of the invention a pharmaceutical composition comprising an effective kinase-inhibiting amount of a compound of formulae I, Ia, Ib, II, IIa, IIb or III is provided in combination with a pharmaceutically acceptable carrier.

In one embodiment, the pharmaceutical composition comprises particles that are less than about 2 microns average particle size. In another embodiment, the composition is incorporated into a biodegradable or non-biodegradable polymer.

In yet another embodiment of the invention, the pharmaceutical compositions comprising the inventive radicicol A analogues further comprise an additive. In some embodiments, the additive is selected from an anti-oxidant, a buffer, a bacteriostat, a liquid carrier, a solute, a suspending agent, a thickening agent, a flavoring agent, a gelatin, glycerin, a binder, a lubricant, an inert diluent, a preservative, a surface active agent, a dispersing agent, a biodegradable polymer, or any combination thereof.

In various embodiments, the pharmaceutical compositions comprise a carrier that is suitable for oral, parenteral, inhalation, topical, or intradermal administration.

Also provided in the invention are methods of treating or preventing a disease in a patient comprising administering to the patient with the disease an effective amount of a compound of formulae I, Ia, Ib, II, IIa, IIb or III, wherein the disease is an autoimmune disease, inflammatory disease, neurological or neurodegenerative disease, an infectious disease, cancer, cardiovascular disease, allergy, asthma, or a hormone-related disease.

In one embodiment, a method of treating a patient with a cancer comprising administering to the patient having the cancer an effective cancer-treating amount of a compound of formulae I, Ia, Ib, II, IIa, IIb or III is provided.

In several embodiments, the cancer may be a solid tumor, blood borne tumor, breast, ovary, cervix, prostate, testis, genitourinary tract, esophagus, larynx, glioblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity, pharynx, lip, tongue, mouth, pharynx, small intestine, colon-rectum, large intestine, rectum, brain and central nervous system, or leukemia.

In another embodiment, a method of treating or preventing a disease in a patient associated with undesirable neovascularization comprising administering to the patient with the undesirable neovascularization an effective amount of a compound of formulae I, Ia, Ib, II, IIa, IIb or III is provided.

In various embodiments, the disease associated with undesirable neovascularization comprises ocular neovascular disease, diabetic retinopathy, retinopathy of prematurity, corneal graft rejection, neovascular glaucoma and retrolental fibroplasias, epidemic keratoconjunctivitis, Vitamin A deficiency, contact lens overwear, atopic keratitis, superior limbic keratitis, pterygium keratitis sicca, Sjögren's syndrome, acne rosacea, phylectenulosis, syphilis, *Mycobacteria* infections, lipid degeneration, chemical burns, bacterial ulcers, fungal ulcers, *Herpes simplex* infections, *Herpes zoster* infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, Scleritis, Steven-Johnson disease, pemphigoid, radial keratotomy, or corneal graph rejection, sickle cell anemia, sarcoid, pseudoxanthoma elasticum, Paget's disease, vein occlusion, artery occlusion, carotid obstructive disease, chronic uveitis/vitritis, Lyme's disease, systemic lupus erythematosis, Eales' disease, Bechet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, or post-laser complications.

In still another embodiment of the invention, a method of treating or preventing an inflammatory disease associated with inflammation in a patient comprising administering to the patient with the inflammatory disease an effective amount of a compound of formulae I, Ia, Ib, II, IIa, IIb or III is provided. In various embodiments, the inflammatory disease is excessive or abnormal stimulation of endothelial cells, atherosclerosis, vascular malfunctions, abnormal wound healing, inflammatory and immune disorders, Bechet's disease, gout or gouty arthritis, abnormal angiogenesis accompanying rheumatoid arthritis, skin diseases, psoriasis, diabetic retinopathy, retinopathy of prematurity, retrolental fibroplasia, macular degeneration, corneal graft rejection, neovascular glaucoma or Osler Weber syndrome.

These and other aspects of the present invention will be better understood by reference to the following detailed description and accompanying figures.

DETAILED DESCRIPTION OF THE INVENTION

Figure 1:
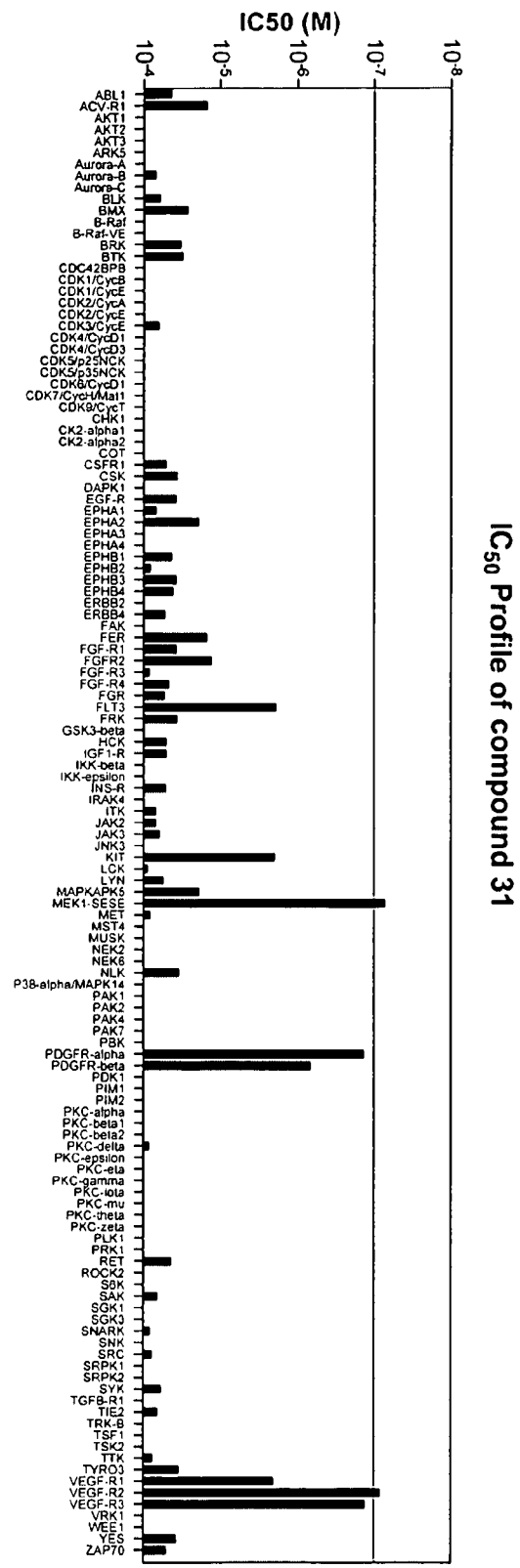
FIG. 1 shows the inhibitory activity of compound 31 ($IC_{50}$) in a panel of 127 kinases.

Provided are novel compounds based on the resorcylic acid lactones that are useful as inhibitors of kinases and phosphatases, including ATPases. Also provided are compositions comprising the compounds and processes for the preparation of the compounds. Use of the compounds for the inhibition of kinases and phosphatases, and methods for the treatment or prevention of kinase-mediated or phosphatase-mediated diseases comprising administering an effective kinase-inhibiting amount or an effective phosphatase-inhibiting amount of a compound of formulae I, Ia, Ib, II, III, IIa or IIb to a patient with a kinase-mediated or phosphatase-mediated disease, are provided.

Macrocycles related to radicicol A have been shown to be potent inhibitors of NF-κβ activation, AP-1 activation and protein kinases (for example, MEKK, MEK1, PDGFr, VEGFr and the like). Based on these mechanisms of action, the compounds inhibit the production of various pro-inflammatory and/or immunologic cytokines such as TNF-α, IL-1, IL-6, IL-8, IL-2 etc, and also inhibit the production of various pro-inflammatory molecules under the regulation of NF-κβ pathway such as prostaglandins produced from COX-2, ICAM-1 and MMP-1 and 3 etc. In addition, macrocycles related to radicicol A have ability to inhibit cell proliferation under the regulation of AP-1 pathway through the inhibition of MEK1. In addition, the compounds have ability to inhibit angiogenesis based on the inhibitory activities on VEGFr and PDGFr kinases. Thus, the compounds of the invention, and pharmaceutical compositions thereof, are useful as anti-inflammatory and/or immunosuppressive agents for the treatment of various inflammatory diseases, and abnormal cell proliferation or as antiangiogenesis agents for the treatment of cancer. In other embodiments, the compounds are useful for the treatment of neurodegenerative disorders, and in the treatment of infectious diseases such as malaria or mycobacterial diseases. In certain embodiments, the compounds of the present invention can be used for the treatment of diseases and disorders including, but not limited to, sepsis, rheumatoid arthritis, psoriatic arthritis, osteoarthritis, inflammatory bowel disease (Crohn's disease and ulcerative colitis), multiple sclerosis, atopic dermatitis, psoriasis, asthma, osteoporosis, allergic rhinitis, ocular inflammation, hepatitis, autoimmune disorders, systemic lupus erthematosus, allograft rejection/graft versus host disease, diabetes, AIDS, solid tumor cancers, leukemia, lymphomas, non-Hodgkin's B-cell lymphomas, chronical lymphocytic leukemia (CLL), multiple myeloma, eczema, urticaria, myasthenia gravis, idiopathic thrombocytopenia purpura, cardiovascular disease (e.g., myocardial infarction, atherosclerosis), hepatitis, glomerulonephropathy, productive nephritis, adenovirus, diseases/disorders of the central nervous system (e.g., stroke, Alzheimer's disease, epilepsy) and for the treatment of the symptoms of malaria, to name a few. The inventive compounds also find use in the prevention of restenosis of blood vessels subject to traumas such as angioplasty and stenting.

Compounds

Novel analogues of radicicol A and related resorcylic acid lactones (RAL), tautomers thereof, pharmaceutically acceptable salts, solvates, esters or prodrugs thereof, and pharmaceutical compositions comprising the compounds for the treatment of kinase-mediated or phosphatase-mediated disorders are provided. Also presented are methods for the treatment of kinase-mediated or phosphatase-mediated disorders using the compounds of the invention. The compounds of the invention are active as kinase inhibitors and inhibitors of phosphatase. In addition, improved processes for the preparation of the compounds that are amenable to automated synthesis techniques are provided.

In a first embodiment of the invention, a compound of formula I, a tautomer thereof, or a pharmaceutically acceptable salt, solvate, ester or prodrug thereof, is provided:

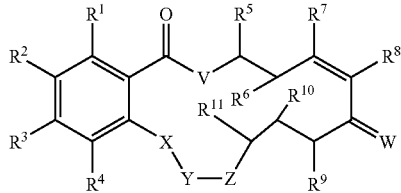

I wherein:
$R^1$, $R^2$, $R^3$ and $R^4$ are each independently hydrogen, halogen, cyano, —OR, —NRR$^X$, —NRS(O)R$^X$, —NRS(O)$_2$R$^X$, —SR, —S(O)R, —S(O)$_2$R, —OC(O)R, —C(O)R, —C(O)OR, —NRC(O)R$^X$, —C(O)NRR$^X$, —OC(O)OR, aliphatic, heteroaliphatic, acyl, aryl, heteroaryl, alkylaryl, arylalkyl, alkylheteroaryl or heteroarylalkyl;

$R^5$ and $R^6$ are each independently hydrogen, halogen, cyano, aliphatic, heteroaliphatic, aryl, heteroaryl, alkylaryl, arylalkyl, alkylheteroaryl, heteroarylalkyl, halogen or a leaving group;

$R^7$ and $R^8$ are each independently hydrogen, halogen, cyano, —OR, —NRR$^X$, —NRS(O)R$^X$, —NRS(O)$_2$R$^X$, —SR, —S(O)R, —S(O)$_2$R, —OC(O)R, —C(O)R, —C(O)OR, —NRC(O)R$^X$, —C(O)NRR$^X$, —OC(O)OR, aliphatic, heteroaliphatic, aryl, heteroaryl, alkylaryl, arylalkyl, alkylheteroaryl, heteroarylalkyl, or a leaving group;

$R^9$, $R^{10}$ and $R^{11}$ are each independently hydrogen, azide, —OR, —NRR$^X$, —NRS(O)R$^X$, —NRS(O)$_2$R$^X$, —SR, —S(O)R, —S(O)$_2$R, —OC(O)R, —C(O)R, —C(O)OR, —NRC(O)R$^X$, —C(O)NRR$^X$, —OC(O)OR, aliphatic, heteroaliphatic, aryl, heteroaryl, alkylaryl or alkylheteroaryl;

V is O, S or NR;

W is O, S, N—R, N—OR, N—NHS(O)$_2$R, N-acyl, or N—NH-acyl;

X and Y are independently CH$_2$, O, S or NR; or X and Y together represent —CHR—CHR—; cis- or trans —CR=CR$^X$—; —CH(OH)—CH(OH)—; —CH(halogen)-CH(OH); —CH(OH)—CH(halogen); or one of X and Y is O, S or NR and the other of X and Y is CH$_2$; or one of X or Y is N and the other of X or Y is =CH; or X and Y together represent 1,2-cyclopropadiyl, or 1,2-oxirane; or X together with Y represent a covalent bond; or Y together with Z represent a covalent bond;

Z is CRR$^X$, =CR—, O, S, =N, NR or Z represents a covalent bond, or Z together with Y represent a covalent bond; and R and R$^X$ are independently hydrogen, aliphatic, heteroaliphatic, aryl, arylalkyl, alkylaryl, heteroaryl, alkylheteroaryl, heteroarylalkyl, acyl including acetyl, sulfonyl or a protecting group; with the proviso that when Z is a covalent bond, W is O and R$^6$ is lower alkyl, then R$^7$ is not hydrogen; and with the additional proviso that R$^7$ is not hydrogen when Z is a covalent bond; W is O; R$^4$ is hydrogen, OMe or —CO$_2$Me; X and Y together form trans —CH=CH— or —C(CH$_3$)=CH— or X and Y together form an epoxide ring or a cyclopropyl ring; and with the further proviso that when Z is a covalent bond; R$^5$ is methyl; R$^3$ is OH, C$_{1-4}$ alkoxy or C$_{1-4}$alkylCOO—; R$^4$ is H, OH, C$_{1-4}$ alkoxy or C$_{1-4}$alkylCOO—; V is O; W is O; X and Y together represent —CH$_2$—CH$_2$ or —CH=CH—; R$^9$ or R$^{10}$ are H, OH, C$_{1-4}$ alkoxy or $C_{1-4}$alkylCOO—; then $R^7$ or $R^8$ are not both hydrogen or $R^7$ or $R^8$ are not OH, $C_{1-4}$alkoxy or $C_{1-4}$alkylCOO—;

wherein aliphatic, aryl, heteroaryl, alkylaryl, arylalkyl, heteroarylalkyl or alkylheteroaryl are optionally substituted.

In another embodiment of the invention, a compound of formula Ia, a tautomer thereof, or a pharmaceutically acceptable salt, solvate, ester or prodrug thereof, is provided:

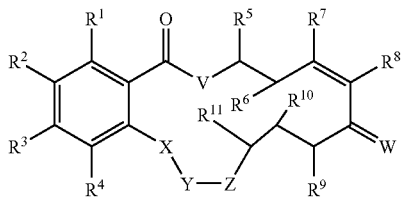

Ia wherein:
$R^1, R^2, R^3, R^4, R^5, R^6, R^7, R^8, V, W, R^9, R^{10}, R^{11}, Z, Y,$ and X are as defined for the compound of formula I; with the proviso that when $R^8$ is hydrogen or halogen, $R^7$ is not hydrogen, OH, $C_{1-4}$alkoxy, or $C_{1-4}$alkylCOO—.

In another embodiment of the invention, a compound of formula Ib, a tautomer thereof, or a pharmaceutically acceptable salt, solvate, ester or prodrug thereof, is provided:

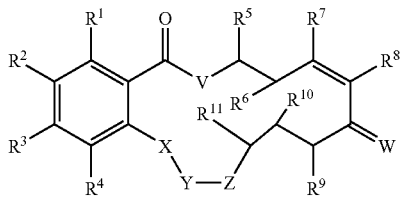

Ib wherein:
$R^1, R^2, R^3, R^4, R^5, R^6, R^7, R^8, V, W, R^9, R^{10}, R^{11}, Z, Y,$ and X are as defined for the compound of formula I; with the proviso that (1) when Z is a covalent bond, W is O and $R^6$ is lower alkyl, then $R^7$ is not hydrogen; and with the additional proviso that (2) $R^7$ is not hydrogen when Z is a covalent bond; W is O; $R^4$ is hydrogen, OMe or —$CO_2Me$; X and Y together form trans —CH=CH— or —C($CH_3$)=CH— or X and Y together form an epoxide ring or a cyclopropyl ring; and with the further proviso (3) that when Z is a covalent bond; V is O; $R^5$ is methyl; $R^3$ is OH, $C_{1-4}$ alkoxy or $C_{1-4}$alkylCOO—; $R^4$ is H, OH, $C_{1-4}$ alkoxy or $C_{1-4}$alkylCOO—; V is O; W is O; X and Y together represent —$CH_2$—$CH_2$— or —CH=CH—; $R^9$ or $R^{10}$ are H, OH, $C_{1-4}$ alkoxy or $C_{1-4}$alkylCOO—; then $R^7$ or $R^8$ are not both hydrogen or $R^7$ or $R^8$ are not OH, $C_{1-4}$alkoxy or $C_{1-4}$alkylCOO—; and with the additional proviso (4) that when $R^1$ is OH or —O-lower acyl; $R^3$ is OH, lower alkoxy or —O-lower acyl; $R^4$ is H or halogen; $R^5$ is lower alkyl; $R^9$ and $R^{10}$ are OH; Z is a covalent bond; V is O; W is O; and X and Y together represent a trans- —CH=CH—; then $R^7$ is not hydrogen.

In one embodiment of formulae I, Ia or Ib, V is O or S. In another embodiment, V is NR.

In one embodiment of formulae I, Ia or Ib, Y and Z together represent a covalent bond.

In another embodiment of formulae I, Ia or Ib, Z represents a covalent bond. In another embodiment, Z is O, S or NR. In still another embodiment of formulae I, Ia or Ib, Z is =CR or $CRR^x$.

In another embodiment of formulae I, Ia or Ib, Z represents a covalent bond and X and Y together represent cis- or trans —CH=CH—.

In another embodiment of formulae I, Ia or Ib, Z represents a covalent bond and X and Y together represent a 1,2-oxirane group or a 1,2-cyclopropadiyl group.

In another embodiment of formulae I, Ia or Ib, X and Y together represent —CH(OH)—CH(OH)—; —CH(halogen)-CH(OH)—; or —CH(OH)—CH(halogen)-.

In one embodiment of formulae I, Ia or Ib, W is O and X is S or O.

In another embodiment of formulae I, Ia or Ib, W is O and X is NR or $CH_2$.

In still another embodiment of formulae I, Ia or Ib, Y is O or S.

In another embodiment of formulae I, Ia or Ib, $R^9$ and $R^{10}$ are OH and W is O.

In one embodiment of the compound of formulae I, Ia or Ib, $R^1$ is OR, $R^3$ is OR or NR and $R^4$ is H or halogen.

In one embodiment of the compound of formulae I, Ia or Ib, $R^2$ is OR, NR or halogen; and $R^4$ is H or halogen.

In another embodiment, of the compound of formula I, Ia or Ib, $R^1$ is OR; $R^2$ is OR, NR or halogen; and $R^4$ is H or halogen.

In another embodiment of formulae I, Ia or Ib, $R^1$ is OH, $R^4$ is OH or halogen, and W is O.

In another embodiment of formulae I, Ia or Ib, $R^5$ is H or aliphatic, $R^9$ and $R^{10}$ are independently OR or NR, and W is O.

In another embodiment of formulae I, Ia or Ib, $R^5$ is H or aliphatic, $R^9$ and $R^{10}$ are independently OR or NR, and W is N—R, N—OR, N—NHS(O)$_2$R, N-acyl or N—NH-acyl.

In another embodiment of formulae I, Ia or Ib, $R^5$ is H or aliphatic; $R^{11}$ is H, OR or NR; and W is O.

In another embodiment of formulae I, Ia or Ib, $R^5$ is H or aliphatic; $R^{11}$ is H, OR or NR; and W is N—R, N—OR, N—NHS(O)$_2$R, N-acyl or N—NH-acyl.

In another embodiment of formulae I, Ia or Ib, $R^1$ is OH, $R^4$ is H or halogen, X is $CH_2$ or O and W is O.

In another embodiment of formulae I, Ia or Ib, $R^1$ is OH; $R^4$ is H or halogen; X is $CH_2$ or O; and W is N—R, N—OR, N—NHS(O)$_2$R, N-acyl or N—NH-acyl.

In another embodiment of formulae I, Ia or Ib, $R^5$ is H or lower alkyl; $R^7$ is hydrogen, aliphatic or halogen; and $R^8$ is hydrogen or halogen.

In another embodiment of formulae I, Ia or Ib, $R^5$ is H or lower alkyl; $R^7$ is methyl, chloro or fluoro; and $R^8$ is hydrogen.

In another embodiment of formulae I, Ia or Ib, $R^5$ is H or lower alkyl; $R^7$ is hydrogen, aliphatic or halogen; and $R^8$ is hydrogen, aliphatic or halogen.

In another embodiment of formulae I, Ia or Ib, $R^5$ is H or lower alkyl; $R^7$ is hydrogen, aliphatic or halogen; and $R^8$ is methyl, chloro or fluoro.

In another embodiment of formulae I, Ia or Ib, $R^5$ and $R^6$ are independently H or lower alkyl; $R^7$ is hydrogen, aliphatic or halogen; and $R^8$ is hydrogen or halogen.

In another embodiment of formulae I, Ia or Ib, $R^5$ and $R^6$ are independently H or lower alkyl; $R^7$ is methyl, chloro or fluoro; and $R^8$ is hydrogen.

In another embodiment of formulae I, Ia or Ib, $R^5$ and $R^6$ are independently H or lower alkyl; $R^7$ is hydrogen, aliphatic or halogen; and $R^8$ is hydrogen, aliphatic or halogen.

In another embodiment of formulae I, Ia or Ib, $R^5$ and $R^6$ are independently H or lower alkyl; $R^7$ is hydrogen, aliphatic or halogen; and $R^8$ is methyl, chloro or fluoro.

In another embodiment of formulae I, Ia or Ib, $R^1$ is OH; $R^2$ is H, OR, NR or halogen; $R^3$ is OR, NR or —NHS(O)$_2$R; $R^4$ is H or halogen; $R^5$ is H or lower alkyl; $R^7$ is hydrogen, aliphatic or halogen; and Z is a bond.

In another embodiment of formulae I, Ia or Ib, $R^1$ is OH; $R^2$ is OR, NR or halogen; $R^3$ is OR, NR or —NHS(O)$_2$R; $R^4$ is H or halogen; $R^5$ is H or lower alkyl; $R^8$ is hydrogen, aliphatic or halogen; and W is O.

In another embodiment of formulae I, Ia or Ib, $R^1$ is OH; $R^2$ is OR, NR or halogen; $R^3$ is OR, NR or —NHS(O)$_2$R; $R^4$ is H or halogen; $R^5$ is H or lower alkyl; $R^7$ is hydrogen, aliphatic or halogen; W is O; and X and Y together represent —CH=CH—.

In another embodiment of formulae I, Ia or Ib, $R^1$ is OH; $R^2$ is OR, NR or halogen; $R^3$ is OR, NR or —NHS(O)$_2$R; $R^4$ is H or halogen; $R^5$ is H or lower alkyl; $R^8$ is hydrogen, aliphatic or halogen; W is O; and X and Y together represent —CH=CH—.

In another embodiment of formulae I, Ia or Ib, $R^1$ is OH; $R^2$ is OR, NR or halogen; $R^3$ is OR, NR or —NHS(O)$_2$R; $R^4$ is H or halogen; $R^5$ is H or alkyl; $R^7$ is hydrogen, aliphatic or halogen; X is O; and Z and Y together represent a covalent bond.

In another embodiment of formulae I, Ia or Ib, $R^1$ is OH; $R^2$ is OR, NR or halogen; $R^3$ is OR, NR or —NHS(O)$_2$R; $R^4$ is H or halogen; $R^5$ is H or alkyl; $R^8$ is hydrogen, aliphatic or halogen; X is O; and Z and Y together represent a covalent bond.

In another embodiment of formulae I, Ia or Ib, $R^1$ is OH; $R^2$ is OR, NR or halogen; $R^3$ is OR, NR or —NHS(O)$_2$R; $R^4$ is H or halogen; $R^5$ is H or alkyl; $R^7$ is hydrogen, aliphatic or halogen; X is O; and Z is —CH$_2$—.

In another embodiment of formulae I, Ia or Ib, $R^1$ is OH; $R^2$ is OR, NR or halogen; $R^3$ is OR, NR or —NHS(O)$_2$R; $R^4$ is H or halogen; $R^5$ is H or alkyl; $R^8$ is hydrogen, aliphatic or halogen; X is O; and Z is —CH$_2$—.

In another embodiment of formulae I, Ia or Ib, $R^1$ is OH; $R^2$ is OR, NR or halogen; $R^3$ is OR, NR or —NHS(O)$_2$R; $R^4$ is H or halogen; $R^5$ and $R^6$ are independently H or alkyl; $R^7$ is aliphatic or halogen; $R^8$ is hydrogen; $R^9$ and $R^{10}$ are H, OR or NR; X and Y together represent cis or trans —CH=CH—; and Z is —CH$_2$—.

In another embodiment of formulae I, Ia or Ib, $R^1$ is OH; $R^2$ is OR, NR or halogen; $R^3$ is OR, NR or —NHS(O)$_2$R; $R^4$ is H or halogen; $R^5$ and $R^6$ are independently H or alkyl; $R^7$ is hydrogen, aliphatic or halogen; $R^8$ is aliphatic or halogen; $R^9$ and $R^{10}$ are H, OR or NR; X and Y together represent cis or trans —CH=CH—; and Z is —CH$_2$—.

In another embodiment of formulae I, Ia or Ib, $R^1$ is OH; $R^2$ is OR, NR or halogen; $R^3$ is OR, NR or —NHS(O)$_2$R; $R^4$ is H or halogen; $R^5$ and $R^6$ are independently H or alkyl; $R^7$ is aliphatic or halogen; $R^8$ is hydrogen; $R^9$ and $R^{10}$ are H, OR or NR; X and Y together represent —CH(OH)—CH(OH)—; —CH(halogen)-CH(OH); or —CH(OH)—CH(halogen); and Z is —CH$_2$—.

In another embodiment of formulae I, Ia or Ib, $R^1$ is OH; $R^2$ is OR, NR or halogen; $R^3$ is OR, NR or —NHS(O)$_2$R; $R^4$ is H or halogen; $R^5$ and $R^6$ are independently H or alkyl; $R^7$ is hydrogen, aliphatic or halogen; $R^8$ is aliphatic or halogen; $R^9$ and $R^{10}$ are H, OR or NR; X and Y together represent —CH(OH)—CH(OH)—; —CH(halogen)-CH(OH); or —CH(OH)—CH(halogen); and Z is —CH$_2$—.

In another embodiment of formulae I, Ia or Ib, $R^1$ is OH; $R^2$ is OR, NR or halogen; $R^3$ is OR, NR or —NHS(O)$_2$R; $R^4$ is H or halogen; $R^5$ and $R^6$ are independently H or alkyl; $R^7$ is aliphatic or halogen; $R^8$ is hydrogen; $R^9$ and $R^{10}$ are H, OR or NR; X and Y together represent a 1,2-oxirane group or a 1,2-cyclopropadiyl group; and Z is —CH$_2$—.

In another embodiment of formulae I, Ia or Ib, $R^1$ is OH; $R^2$ is OR, NR or halogen; $R^3$ is OR, NR or —NHS(O)$_2$R; $R^4$ is H or halogen; $R^5$ and $R^6$ are independently H or alkyl; $R^7$ is hydrogen, aliphatic or halogen; $R^8$ is aliphatic or halogen; $R^9$ and $R^{10}$ are H, OR or NR; X and Y together represent a 1,2-oxirane group or a 1,2-cyclopropadiyl group; and Z is —CH$_2$—.

In yet another embodiment of formulae I, Ia or Ib, $R^1$ is OH; $R^2$ is OR, NR or halogen; $R^3$ is OR or NR or —NHS(O)$_2$R; $R^4$ is H or halogen; $R^5$ and $R^6$ are independently H or methyl; $R^7$ is lower alkyl or halogen; $R^8$ is hydrogen; $R^9$ and $R^{10}$ are H, OR or NR; X and Y together represent cis or trans —CH=CH—; and Z is —CH$_2$—.

In another embodiment of formulae I, Ia or Ib, $R^1$ is OH; $R^2$ is OR, NR or halogen; $R^3$ is OR, NR or —NHS(O)$_2$R; $R^4$ is H or halogen; $R^5$ and $R^6$ are independently H or methyl; $R^7$ is hydrogen, aliphatic or halogen; $R^8$ is lower alkyl or halogen; $R^9$ and $R^{10}$ are H, OR or NR; X and Y together represent cis or trans —CH=CH—; and Z is —CH$_2$—.

In a another embodiment of the invention, a compound of formula II, a tautomer thereof, or a pharmaceutically acceptable salt, solvate, ester or prodrug thereof, is provided:

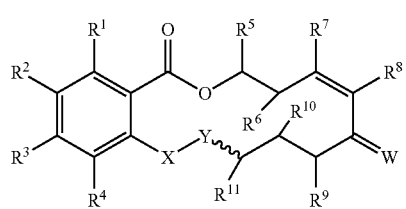

wherein, R, $R^1$, $R^2$, $R^3$, $R^4$, $R^5$, $R^6$, $R^7$, $R^8$, $R^9$, $R^{10}$, $R^{11}$, W, X and Y are as defined for formula I above.

In one embodiment of formula II, X and Y together represent cis- or trans-CH=CH—.

In another embodiment of formula II, X and Y together represent a 1,2-oxirane group or a 1,2-cyclopropadiyl group.

In another embodiment of formula II, X and Y together represent —CH(OH)—CH(OH)—; —CH(halogen)-CH(OH); or —CH(OH)—CH(halogen).

In one embodiment of formula II, W is O and X is S or O.

In another embodiment of formula II, W is O and X is NR or CH$_2$.

In still another embodiment of formula II, Y is O or S.

In another embodiment of formula II, $R^9$ and $R^{10}$ are OH and W is O.

In one embodiment of the compound of formula II, $R^1$ is OR, $R^3$ is OR or NR and $R^4$ is H or halogen.

In one embodiment of the compound of formula II, $R^2$ is OR, NR or halogen; and $R^4$ is H or halogen.

In another embodiment of the compound of formula II, $R^1$ is OR, $R^2$ is OR, NR or halogen and $R^4$ is H or halogen.

In another embodiment of formula II, $R^1$ is OH, $R^4$ is OH or halogen, and W is O.

In another embodiment of formula II, $R^5$ is H or aliphatic, $R^9$ and $R^{10}$ are independently OR or NR, and W is O.

In another embodiment of formula II, $R^5$ is H or aliphatic, $R^9$ and $R^{10}$ are independently OR or NR, and W is N—R, N—OR, N—NHS(O)$_2$R, N-acyl or N—NH-acyl.

In another embodiment of formula II, $R^5$ is H or aliphatic; $R^{11}$ is H, OR or NR, and W is O.

In another embodiment of formula II, $R^5$ is H or aliphatic; $R^{11}$ is H, OR or NR; and W is N—R, N—OR, N—NHS(O)$_2$R, N-acyl or N—NH-acyl.

In another embodiment of formula II, $R^1$ is OH, $R^4$ is H or halogen, X is CH$_2$ or O and W is O.

In another embodiment of formula II, $R^1$ is OH; $R^4$ is H or halogen; X is CH$_2$ or O; and W is N—R, N—OR, N—NHS(O)$_2$R, N-acyl or N—NH-acyl.

In another embodiment of formula II, $R^5$ and $R^6$ are independently H or lower alkyl; $R^7$ is hydrogen, aliphatic or halogen; and $R^8$ is hydrogen or halogen.

In another embodiment of formula II, $R^5$ and $R^6$ are independently H or lower alkyl; $R^7$ is methyl, chloro or fluoro; and $R^8$ is hydrogen.

In another embodiment of formula II, $R^5$ and $R^6$ are independently H or lower alkyl; $R^7$ is hydrogen, aliphatic or halogen; and $R^8$ is hydrogen, aliphatic or halogen.

In another embodiment of formula II, $R^5$ and $R^6$ are independently H or lower alkyl; $R^7$ is hydrogen, aliphatic or halogen; and $R^8$ is methyl, chloro or fluoro.

In another embodiment of formula II, $R^1$ is OH; $R^2$ is H, OR, NR or halogen; $R^3$ is OR, NR or —NHS(O)$_2$R; $R^4$ is H or halogen; $R^5$ is H or lower alkyl; and $R^7$ is hydrogen, aliphatic or halogen.

In another embodiment of formula II, $R^1$ is OH; $R^2$ is OR, NR or halogen; $R^3$ is OR, NR or —NHS(O)$_2$R; $R^4$ is H or halogen; $R^5$ is H or lower alkyl; $R^8$ is hydrogen, aliphatic or halogen; and W is O.

In another embodiment of formula II, $R^1$ is OH; $R^2$ is OR, NR or halogen; $R^3$ is OR, NR or —NHS(O)$_2$R; $R^4$ is H or halogen; $R^5$ is H or lower alkyl; $R^7$ is hydrogen, aliphatic or halogen; W is O; and X and Y together represent —CH=CH—.

In another embodiment of formula II, $R^1$ is OH; $R^2$ is OR, NR or halogen; $R^3$ is OR, NR or —NHS(O)$_2$R; $R^4$ is H or halogen; $R^5$ is H or lower alkyl; $R^8$ is hydrogen, aliphatic or halogen; W is O; and X and Y together represent —CH=CH—.

In another embodiment of formula II, $R^1$ is OH; $R^2$ is OR, NR or halogen; $R^3$ is OR,NR or —NHS(O)$_2$R; $R^4$ is H or halogen; $R^5$ is H or alkyl; $R^7$ is hydrogen, aliphatic or halogen; and X is O.

In another embodiment of formula II, $R^1$ is OH; $R^2$ is OR, NR or halogen; $R^3$ is OR, NR or —NHS(O)$_2$R; $R^4$ is H or halogen; $R^5$ is H or alkyl; $R^8$ is hydrogen, aliphatic or halogen; and X is O.

In another embodiment of formula II, $R^1$ is OH; $R^2$ is OR, NR or halogen; $R^3$ is OR, NR or —NHS(O)$_2$R; $R^4$ is H or halogen; $R^5$ is H or alkyl; $R^7$ is hydrogen, aliphatic or halogen; and X is —CH$_2$—.

In another embodiment of formula II, $R^1$ is OH; $R^2$ is OR, NR or halogen; $R^3$ is OR, NR or —NHS(O)$_2$R; $R^4$ is H or halogen; $R^5$ is H or alkyl; $R^8$ is hydrogen, aliphatic or halogen; and X is —CH$_2$—.

In another embodiment of formula II, $R^1$ is OH; $R^2$ is OR, NR or halogen; $R^3$ is OR, NR or —NHS(O)$_2$R; $R^4$ is H or halogen; $R^5$ and $R^6$ are independently H or alkyl; $R^7$ is aliphatic or halogen; $R^8$ is hydrogen; $R^9$ and $R^{10}$ are H, OR or NR; and X and Y together represent cis or trans —CH=CH—.

In another embodiment of formula II, $R^1$ is OH; $R^2$ is OR, NR or halogen; $R^3$ is OR, NR or —NHS(O)$_2$R; $R^4$ is H or halogen; $R^5$ and $R^6$ are independently H or alkyl; $R^7$ is hydrogen, aliphatic or halogen; $R^8$ is aliphatic or halogen; $R^9$ and $R^{10}$ are H, OR or NR; and X and Y together represent cis or trans —CH=CH—.

In another embodiment of formula II, $R^1$ is OH; $R^2$ is OR, NR or halogen; $R^3$ is OR, NR or —NHS(O)$_2$R; $R^4$ is H or halogen; $R^5$ and $R^6$ are independently H or alkyl; $R^7$ is aliphatic or halogen; $R^8$ is hydrogen; $R^9$ and $R^{10}$ are H, OR or NR; and X and Y together represent —CH(OH)—CH(OH)—; —CH(halogen)-CH(OH); or —CH(OH)—CH(halogen).

In another embodiment of formula II, $R^1$ is OH; $R^2$ is OR, NR or halogen; $R^3$ is OR, NR or —NHS(O)$_2$R; $R^4$ is H or halogen; $R^5$ and $R^6$ are independently H or alkyl; $R^7$ is hydrogen, aliphatic or halogen; $R^8$ is aliphatic or halogen; $R^9$ and $R^{10}$ are H, OR or NR; and X and Y together represent —CH(OH)—CH(OH)—; —CH(halogen)-CH(OH); or —CH(OH)—CH(halogen).

In another embodiment of formula II, $R^1$ is OH; $R^2$ is OR, NR or halogen; $R^3$ is OR, NR or —NHS(O)$_2$R; $R^4$ is H or halogen; $R^5$ and $R^6$ are independently H or alkyl; $R^7$ is aliphatic or halogen; $R^8$ is hydrogen; $R^9$ and $R^{10}$ are H, OR or NR; and X and Y together represent a 1,2-oxirane group or a 1,2-cyclopropadiyl group.

In another embodiment of formula II, $R^1$ is OH; $R^2$ is OR, NR or halogen; $R^3$ is OR or NR or —NHS(O)$_2$R; $R^4$ is H or halogen; $R^5$ and $R^6$ are independently H or alkyl; $R^7$ is hydrogen, aliphatic or halogen; $R^8$ is aliphatic or halogen; $R^9$ and $R^{10}$ are H, OR or NR; and X and Y together represent a 1,2-oxirane group or a 1,2-cyclopropadiyl group.

In yet another embodiment of formula II, $R^1$ is OH; $R^2$ is OR, NR or halogen; $R^3$ is OR, NR or —NHS(O)$_2$R; $R^4$ is H or halogen; $R^5$ and $R^6$ are independently H or methyl; $R^7$ is lower alkyl or halogen; $R^8$ is hydrogen; $R^9$ and $R^{10}$ are H, OR or NR; and X and Y together represent cis or trans —CH=CH—.

In another embodiment of formula II, $R^1$ is OH; $R^2$ is OR, NR or halogen; $R^3$ is OR, NR or —NHS(O)$_2$R; $R^4$ is H or halogen; $R^5$ and $R^6$ are independently H or methyl; $R^7$ is hydrogen, aliphatic or halogen; $R^8$ is lower alkyl or halogen; $R^9$ and $R^{10}$ are H, OR or NR; and X and Y together represent cis or trans —CH=CH—.

In a third embodiment of the invention, a compound of formula III, a tautomer thereof, or a pharmaceutically acceptable salt, solvate, ester or prodrug thereof, is provided:

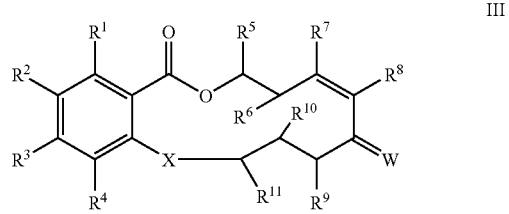

wherein, R, $R^1$, $R^2$, $R^3$, $R^4$, $R^5$, $R^6$, $R^7$, $R^8$, $R^9$, $R^{10}$, $R^{11}$, W and X are as defined for formula I above.

In one embodiment of formula III, W is O and X is S or O.

In another embodiment of formula III, W is O and X is NR or CH$_2$.

In another embodiment of formula III, $R^9$ and $R^{10}$ are OH and W is O.

In one embodiment of the compound of formula III, $R^1$ is OR, $R^3$ is OR or NR and $R^4$ is H or halogen.

In one embodiment of the compound of formula III, $R^2$ is OR, NR or halogen; and $R^4$ is H or halogen.

In another embodiment of the compound of formula III, $R^1$ is OR; $R^2$ is OR, NR or halogen; and $R^4$ is H or halogen.

In another embodiment of formula III, $R^1$ is OH, $R^4$ is OH or halogen, and W is O.

In another embodiment of formula III, $R^5$ is H or aliphatic, $R^9$ and $R^{10}$ are independently OR or NR, and W is O.

In another embodiment of formula III, $R^5$ is H or aliphatic; $R^9$ and $R^{10}$ are independently OR or NR; and W is N—R, N—OR, N—NHS(O)$_2$R, N-acyl or N—NH-acyl.

In another embodiment of formula III, $R^5$ is H or aliphatic; $R^{11}$ is H, OR or NR; and W is O.

In another embodiment of formula III, $R^5$ is H or aliphatic; $R^{11}$ is H, OR or NR, and W is N—R, N—OR, N—NHS(O)$_2$R, N-acyl or N—NH-acyl.

In another embodiment of formula III, $R^1$ is OH, $R^4$ is H or halogen, X is CH$_2$ or O and W is O.

In another embodiment of formula III, $R^1$ is OH; $R^4$ is H or halogen; X is CH$_2$ or O; and W is N—R, N—OR, N—NHS(O)$_2$R, N-acyl or N—NH-acyl.

In another embodiment of formula IR, $R^5$ and $R^6$ are independently H or lower alkyl; $R^7$ is hydrogen, aliphatic or halogen; and $R^8$ is hydrogen or halogen.

In another embodiment of formula III, $R^5$ and $R^6$ are independently H or lower alkyl; $R^7$ is methyl, chloro or fluoro; and $R^8$ is hydrogen.

In another embodiment of formula III, $R^5$ and $R^6$ are independently H or lower alkyl; $R^7$ is hydrogen, aliphatic or halogen; and $R^8$ is hydrogen, aliphatic or halogen.

In another embodiment of formula III, $R^5$ and $R^6$ are independently H or lower alkyl; $R^7$ is hydrogen, aliphatic or halogen; and $R^8$ is methyl, chloro or fluoro.

In another embodiment of formula III, $R^1$ is OH; $R^2$ is H, OR, NR or halogen; $R^3$ is OR, NR or —NHS(O)$_2$R; $R^4$ is H or halogen; $R^5$ is H or lower alkyl; and $R^7$ is hydrogen, aliphatic or halogen.

In another embodiment of formula III, $R^1$ is OH; $R^2$ is OR, NR or halogen; $R^3$ is OR, NR or —NHS(O)$_2$R; $R^4$ is H or halogen; $R^5$ is H or lower alkyl; $R^8$ is hydrogen, aliphatic or halogen; and W is O.

In another embodiment of formula III, $R^1$ is OH; $R^2$ is OR, NR or halogen; $R^3$ is OR, NR or —NHS(O)$_2$R; $R^4$ is H or halogen; $R^5$ is H or lower alkyl; $R^7$ is hydrogen, aliphatic or halogen; W is O; and X is O.

In another embodiment of formula III, $R^1$ is OH; $R^2$ is OR, NR or halogen; $R^3$ is OR, NR or —NHS(O)$_2$R; $R^4$ is H or halogen; $R^5$ is H or lower alkyl; $R^8$ is hydrogen, aliphatic or halogen; W is O; and X is O.

In another embodiment of formula III, $R^1$ is OH; $R^2$ is OR, NR or halogen; $R^3$ is OR, NR or —NHS(O)$_2$R; $R^4$ is H or halogen; $R^5$ is H or alkyl; $R^7$ is hydrogen, aliphatic or halogen; and X is O.

In another embodiment of formula III, $R^1$ is OH; $R^2$ is OR, NR or halogen; $R^3$ is OR, NR or —NHS(O)$_2$R; $R^4$ is H or halogen; $R^5$ is H or alkyl; $R^8$ is hydrogen, aliphatic or halogen; and X is O.

In another embodiment of formula III, $R^1$ is OH; $R^2$ is OR, NR or halogen; $R^3$ is OR or NR or —NHS(O)$_2$R; $R^4$ is H or halogen; $R^5$ is H or alkyl; $R^7$ is hydrogen, aliphatic or halogen; X is —CH$_2$—.

In another embodiment of formula III, $R^1$ is OH; $R^2$ is OR, NR or halogen; $R^3$ is OR, NR or —NHS(O)$_2$R; $R^4$ is H or halogen; $R^5$ is H or alkyl; $R^8$ is hydrogen, aliphatic or halogen; X is —CH$_2$—.

In another embodiment of formula III, $R^1$ is OH; $R^2$ is OR, NR or halogen; $R^3$ is OR, NR or —NHS(O)$_2$R; $R^4$ is H or halogen; $R^5$ and $R^6$ are independently H or alkyl; $R^7$ is aliphatic or halogen; $R^8$ is hydrogen; $R^9$ and $R^{10}$ are H, OR or NR; and X is O.

In another embodiment of formula III, $R^1$ is OH; $R^2$ is OR, NR or halogen; $R^3$ is OR, NR or —NHS(O)$_2$R; $R^4$ is H or halogen; $R^5$ and $R^6$ are independently H or alkyl; $R^7$ is hydrogen, aliphatic or halogen; $R^8$ is aliphatic or halogen; $R^9$ and $R^{10}$ are H, OR or NR; and X is O.

In another embodiment of formula III, $R^1$ is OH; $R^2$ is OR, NR or halogen; $R^3$ is OR, NR or —NHS(O)$_2$R; $R^4$ is H or halogen; $R^5$ and $R^6$ are independently H or methyl; $R^7$ is aliphatic or halogen; $R^8$ is hydrogen; $R^9$ and $R^{10}$ are H, OR or NR; and X is —CH$_2$—.

In another embodiment of formula III, $R^1$ is OH; $R^2$ is OR, NR or halogen; $R^3$ is OR, NR or —NHS(O)$_2$R; $R^4$ is H or halogen; $R^5$ and $R^6$ are independently H or methyl; $R^7$ is hydrogen, aliphatic or halogen; $R^8$ is aliphatic or halogen; $R^9$ and $R^{10}$ are H, OR or NR; and X is —CH$_2$—.

In another embodiment, a compound of formula IIa, a tautomer thereof, or a pharmaceutically acceptable salt, solvate, ester or prodrug thereof, is provided:

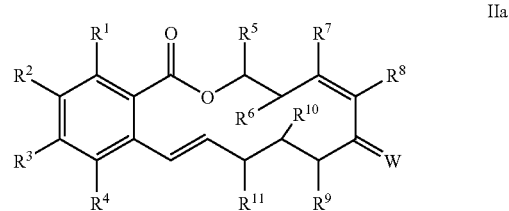

IIa wherein, R, $R^1$, $R^2$, $R^3$, $R^4$, $R^5$, $R^6$, $R^7$, $R^8$, $R^9$, $R^{10}$, $R^{11}$ and W are as defined for formula I above.

In one embodiment of formula IIa, W is O.

In another embodiment of formula IIa, $R^9$ and $R^{10}$ are OH and W is O.

In another embodiment of the compound of formula IIa, $R^1$ is OR, $R^3$ is OR or NR and $R^4$ is H or halogen.

In one embodiment of the compound of formula IIa, $R^2$ is OR, NR or halogen; and $R^4$ is H or halogen.

In another embodiment of the compound of formula IIa, $R^1$ is OR, $R^2$ is OR, NR or halogen and $R^4$ is H or halogen.

In another embodiment of formula IIa, $R^5$ is H or aliphatic, $R^9$ and $R^{10}$ are independently OR or NR, and W is O.

In another embodiment of formula IIa, $R^5$ is H or aliphatic; $R^9$ and $R^{10}$ are independently OR or NR; and W is N—R, N—OR, N—NHS(O)$_2$R, N-acyl or N—NH-acyl.

In another embodiment of formula IIa, $R^5$ is H or aliphatic; $R^{11}$ is H, OR or NR; and W is O.

In another embodiment of formula IIa, $R^5$ is H or aliphatic; $R^{11}$ is H, OR or NR; and W is N—R, N—OR, N—NHS(O)$_2$R, N-acyl or N—NH-acyl.

In another embodiment of formula IIa, $R^1$ is OH, $R^4$ is H or halogen, and W is O.

In another embodiment of formula IIa, $R^1$ is OH; $R^4$ is H or halogen; and W is N—R, N—OR, N—NHS(O)$_2$R, N-acyl or N—NH-acyl.

In another embodiment of formula IIa, $R^5$ and $R^6$ are independently H or lower alkyl, $R^7$ is hydrogen, aliphatic or halogen; and $R^8$ is hydrogen or halogen.

In another embodiment of formula IIa, $R^5$ and $R^6$ are independently H or lower alkyl, $R^7$ is methyl, chloro or fluoro; and $R^8$ is hydrogen.

In another embodiment of formula IIa, $R^5$ and $R^6$ are independently H or lower alkyl, $R^7$ is hydrogen, aliphatic or halogen; and $R^8$ is hydrogen, aliphatic or halogen.

In another embodiment of formula IIa, $R^5$ and $R^6$ are independently H or lower alkyl, $R^7$ is hydrogen, aliphatic or halogen; and $R^8$ is methyl, chloro or fluoro.

In another embodiment of formula IIa, $R^1$ is OH; $R^2$ is H, OR, NR or halogen; $R^3$ is OR, NR or —NHS(O)$_2$R; $R^4$ is H or halogen; $R^5$ is H or lower alkyl; and $R^7$ is hydrogen, aliphatic or halogen.

In another embodiment of formula IIa, $R^1$ is OH; $R^2$ is OR, NR or halogen; $R^3$ is OR, NR or —NHS(O)$_2$R; $R^4$ is H or halogen; $R^5$ is H or lower alkyl; $R^8$ is hydrogen, aliphatic or halogen; and W is O.

In another embodiment of formula IIa, $R^1$ is OH; $R^2$ is OR, NR or halogen; $R^3$ is OR, NR or —NHS(O)$_2$R; $R^4$ is H or halogen; $R^5$ is H or lower alkyl; $R^7$ is hydrogen, aliphatic or halogen; and W is O.

In another embodiment of formula IIa, $R^1$ is OH; $R^2$ is OR, NR or halogen; $R^3$ is OR, NR or —NHS(O)$_2$R; $R^4$ is H or halogen; $R^5$ is H or lower alkyl; $R^8$ is hydrogen, aliphatic or halogen; and W is N—R, N—OR, N—NHS(O)$_2$R, N-acyl or N—NH-acyl.

In another embodiment of formula IIa, $R^1$ is OH; $R^2$ is OR, NR or halogen; $R^3$ is OR, NR or —NHS(O)$_2$R; $R^4$ is H or halogen; $R^5$ is H or alkyl; $R^7$ is hydrogen, aliphatic or halogen; and W is N—R, N—OR, N—NHS(O)$_2$R, N-acyl or N—NH-acyl.

In another embodiment of formula IIa, $R^1$ is OH; $R^2$ is OR, NR or halogen; $R^3$ is OR, NR or —NHS(O)$_2$R; $R^4$ is H or halogen; $R^5$ and $R^6$ are independently H or alkyl; $R^7$ is aliphatic or halogen; $R^8$ is hydrogen; $R^9$ and $R^{10}$ are H, OR or NR; and W is O.

In another embodiment of formula IIa, $R^1$ is OH; $R^2$ is OR, NR or halogen; $R^3$ is OR, NR or —NHS(O)$_2$R; $R^4$ is H or halogen; $R^5$ and $R^6$ are independently H or alkyl; $R^7$ is hydrogen, aliphatic or halogen; $R^8$ is aliphatic or halogen; $R^9$ and $R^{10}$ are H, OR or NR; and W is O.

In another embodiment of formula IIa, $R^1$ is OH; $R^2$ is OR, NR or halogen; $R^3$ is OR, NR or —NHS(O)$_2$R; $R^4$ is H or halogen; $R^5$ and $R^6$ are independently H or alkyl; $R^7$ is aliphatic or halogen; $R^8$ is hydrogen; $R^9$ and $R^{10}$ are H, OR or NR; and W is N—R, N—OR, N—NHS(O)$_2$R, N-acyl or N—NH-acyl.

In another embodiment of formula IIa, $R^1$ is OH; $R^2$ is OR, NR or halogen; $R^3$ is OR, NR or —NHS(O)$_2$R; $R^4$ is H or halogen; $R^5$ and $R^6$ are independently H or alkyl; $R^7$ is hydrogen, aliphatic or halogen; $R^8$ is aliphatic or halogen; $R^9$ and $R^{10}$ are H, OR or NR; and W is N—R, N—OR, N—NHS(O)$_2$R, N-acyl or N—NH-acyl.

In yet another embodiment of formula IIa, $R^1$ is OH; $R^2$ is OR, NR or halogen; $R^3$ is OR or NR or —NHS(O)$_2$R; $R^4$ is H or halogen; $R^5$ and $R^6$ are independently H or methyl; $R^7$ is lower alkyl or halogen; $R^8$ is hydrogen; $R^9$ and $R^{10}$ are H, OR or NR; and W is O.

In another embodiment of formula IIa, $R^1$ is OH; $R^2$ is OR, NR or halogen; $R^3$ is OR or NR or —NHS(O)$_2$R; $R^4$ is H or halogen; $R^5$ and $R^6$ are independently H or methyl; $R^7$ is hydrogen, aliphatic or halogen; $R^8$ is lower alkyl or halogen; $R^9$ and $R^{10}$ are H, OR or NR; and W is O.

In another embodiment of the invention, compound of formula IIb, a tautomer thereof, or a pharmaceutically acceptable salt, solvate, ester or prodrug thereof, is provided:

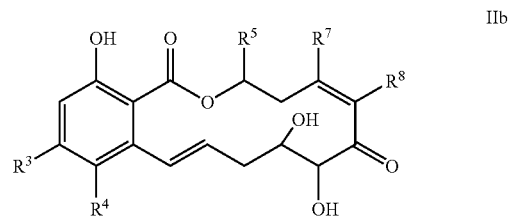

In one embodiment of the compound of formula IIb, $R^3$ is OR or NR and $R^4$ is H or halogen.

In one embodiment of the compound of formula IIb, $R^5$ is H or lower alkyl; and $R^4$ is H or halogen.

In another embodiment of formula IIb, $R^5$ is H or aliphatic, and $R^4$ is halogen.

In another embodiment of formula IIb, $R^5$ is methyl, $R^4$ halogen, and $R^3$ is OR.

In another embodiment of formula IIb, $R^5$ is H or lower alkyl, $R^7$ is hydrogen, aliphatic or halogen; and $R^8$ is hydrogen or halogen.

In another embodiment of formula IIb, $R^5$ is H or lower alkyl, $R^7$ is methyl, chloro or fluoro; and $R^8$ is hydrogen.

In another embodiment of formula IIb, $R^5$ is H or lower alkyl, $R^7$ is hydrogen, aliphatic or halogen; and $R^8$ is hydrogen, aliphatic or halogen.

In another embodiment of formula IIb, $R^5$ is H or lower alkyl, $R^7$ is hydrogen, aliphatic or halogen; and $R^8$ is methyl, chloro or fluoro.

In another embodiment of formula IIb, $R^3$ is OR, NR or —NHS(O)$_2$R; $R^4$ is H or halogen; $R^5$ is H or lower alkyl; and $R^7$ is hydrogen, aliphatic or halogen.

In another embodiment of formula IIb, $R^3$ is OR, NR or —NHS(O)$_2$R; $R^4$ is H or halogen; $R^5$ is H or lower alkyl; and $R^8$ is hydrogen, aliphatic or halogen.

In another embodiment of formula IIb, $R^3$ is OR, NR or —NHS(O)$_2$R; $R^4$ is H or halogen; $R^5$ is H or methyl; $R^7$ is aliphatic or halogen; and $R^8$ is hydrogen.

In another embodiment of formula IIb, $R^3$ is OR, NR or —NHS(O)$_2$R; $R^4$ is H or halogen; $R^5$ is H or alkyl; $R^7$ is hydrogen, aliphatic or halogen; and $R^8$ is aliphatic or halogen.

In yet another embodiment of formula IIb, $R^3$ is OR, NR or —NHS(O)$_2$R; $R^4$ is H or halogen; $R^5$ is H or methyl; $R^7$ is lower alkyl or halogen; and $R^8$ is hydrogen.

In another embodiment of formula IIb, $R^3$ is OR, NR or —NHS(O)$_2$R; $R^4$ is H or halogen; $R^5$ is H or methyl; $R^7$ is hydrogen, aliphatic or halogen; and $R^8$ is lower alkyl or halogen.

In yet another embodiment of formula IIb, $R^3$ is OH; $R^4$ is halogen; $R^5$ is H or methyl; $R^7$ is lower alkyl or halogen; and $R^8$ is hydrogen.

In another embodiment of formula IIb, $R^3$ is OH; $R^4$ is halogen; $R^5$ is H or methyl; $R^7$ is hydrogen, aliphatic or halogen; and $R^8$ is lower alkyl or halogen.

In specific embodiments of the present invention, the compounds presented in Table 1, stereoisomers thereof, tautomers thereof, or pharmaceutically acceptable salts, solvates, esters or prodrugs thereof, are provided:

TABLE 1

| Compound Designation | Structure |
|---|---|
| 31 | 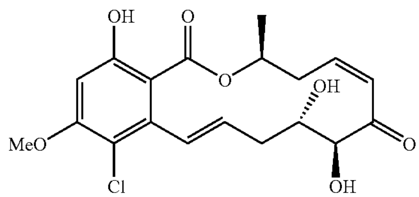 [SMILES: COc1cc(O)c2c(c1Cl)/C=C/C[C@H](O)[C@H](O)C(=O)/C=C\C[C@H](C)OC2=O] |
| 92 | 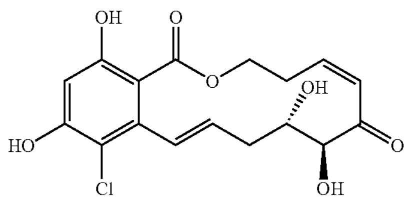 [SMILES: O=C1OCC/C=C\C(=O)[C@@H](O)[C@@H](O)C/C=C/c2c(Cl)c(O)cc(O)c21] |
| 93 | 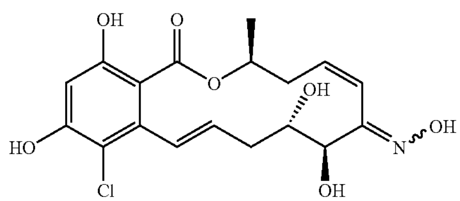 [SMILES: C[C@H]1C/C=C\C(=NO)[C@@H](O)[C@@H](O)C/C=C/c2c(Cl)c(O)cc(O)c2C(=O)O1] |
| 94 | 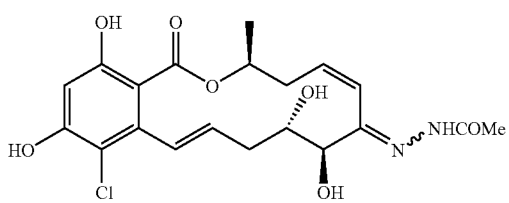 |
| 95 | 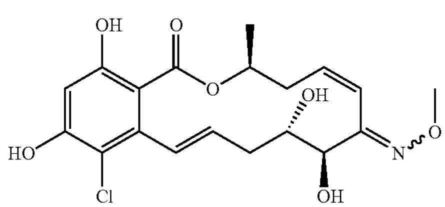 [SMILES: CON=C1/C=C\C[C@H](C)OC(=O)c2c(O)cc(O)c(Cl)c2/C=C/C[C@H](O)[C@@H]1O] |
| 96 | 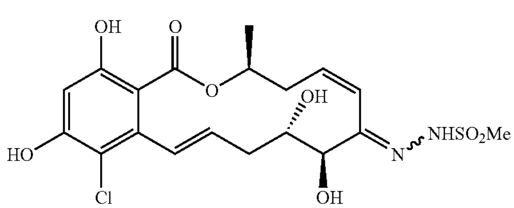 |
| 97 | 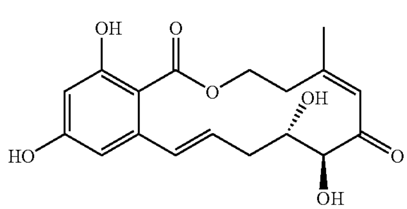 [SMILES: C/C1=C/C(=O)[C@@H](O)[C@@H](O)C/C=C/c2cc(O)cc(O)c2C(=O)OCC1] |

TABLE 1-continued

| Compound Designation | Structure |
|---|---|
| 98 | 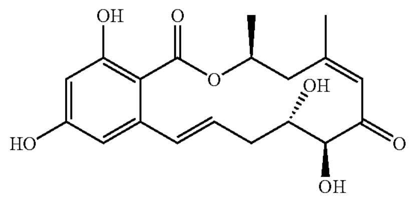 [SMILES: C/C1=C/C(=O)[C@@H](O)[C@@H](O)C/C=C/c2cc(O)cc(O)c2C(=O)O[C@@H](C)C1] |
| 99 | 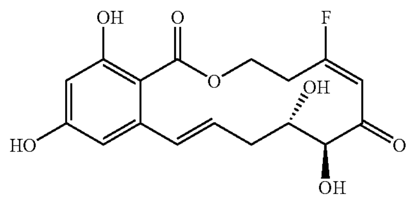 [SMILES: O=C1OCC/C(F)=C\C(=O)[C@@H](O)[C@@H](O)C/C=C/c2cc(O)cc(O)c21] |
| 100 | 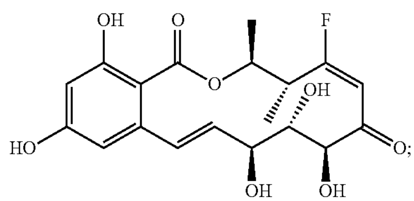 [SMILES: C[C@@H]1OC(=O)c2c(O)cc(O)cc2/C=C/[C@H](O)[C@H](O)[C@H](O)C(=O)/C=C(/F)[C@@H]1C] |
| 101 | 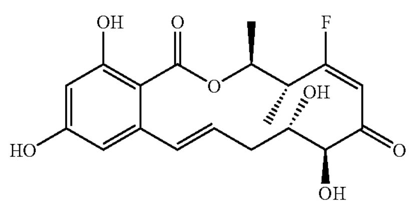 [SMILES: C[C@@H]1OC(=O)c2c(O)cc(O)cc2/C=C/C[C@H](O)[C@H](O)C(=O)/C=C(/F)[C@@H]1C] |
| 102 | 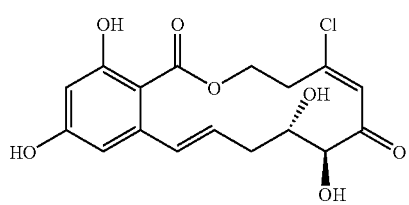 |
| 103 | 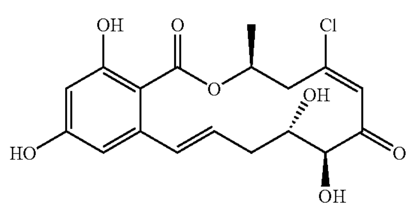 |
| 104 | 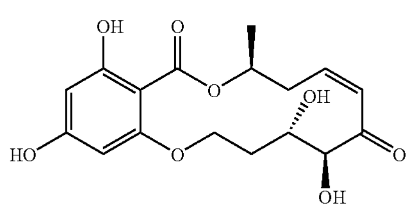 |

TABLE 1-continued

| Compound Designation | Structure |
|---|---|
| 105 | 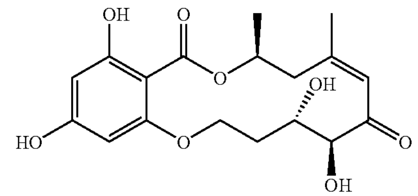 |
| 106 | 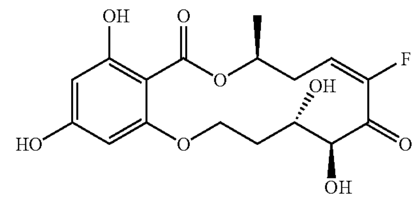 |
| 107 | 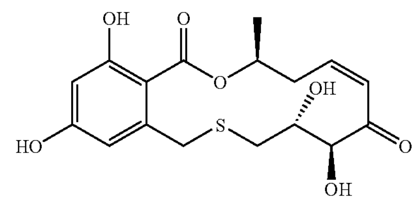 |
| 108 | 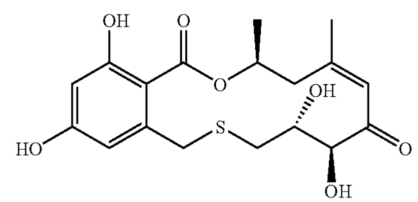 |
| 109 | 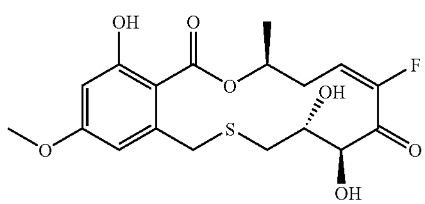 [SMILES: COc1cc(O)c2c(c1)CSC[C@H](O)[C@H](O)C(=O)/C(F)=C\C[C@H](C)OC2=O] |
| 110 | 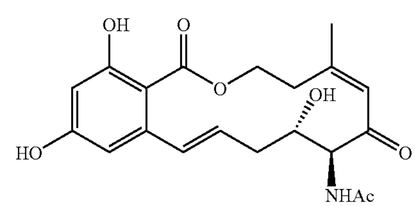 |
| 111 | 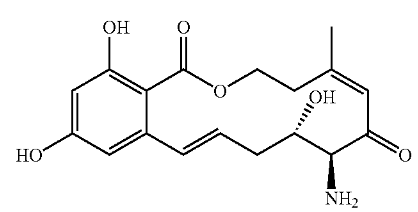 [SMILES: C/C1=C/C(=O)[C@@H](N)[C@@H](O)C/C=C/c2cc(O)cc(O)c2C(=O)OCC1] |

TABLE 1-continued

| Compound Designation | Structure |
| --- | --- |
| 112 | (structure) |
| 113 | (structure) |
| 114 | (structure) |
| 115 | (structure) |
| 116 | (structure) |
| 117 | (structure) |
| 118 | (structure) |

TABLE 1-continued

| Compound Designation | Structure |
|---|---|
| 119 | 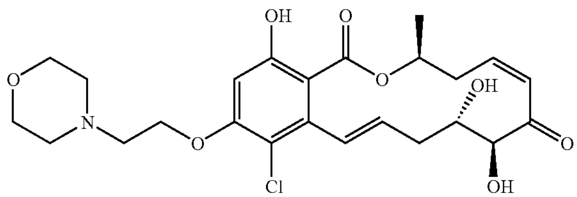 [SMILES: C[C@H]1C/C=C\C(=O)[C@@H](O)[C@@H](O)C/C=C/c2c(Cl)c(OCCN3CCOCC3)cc(O)c2C(=O)O1] |
| 120 | 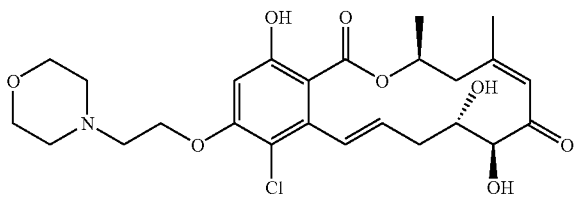 [SMILES: C/C1=C/C(=O)[C@@H](O)[C@@H](O)C/C=C/c2c(Cl)c(OCCN3CCOCC3)cc(O)c2C(=O)O[C@@H](C)C1] |
| 121 | 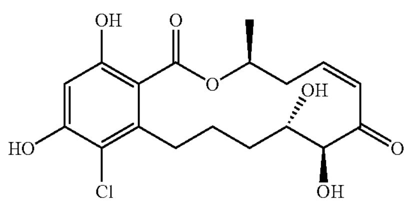 |
| 122 | 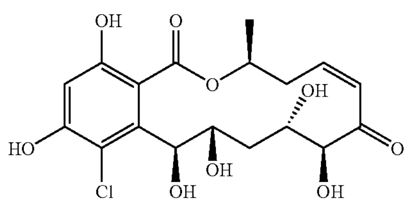 [SMILES: C[C@H]1C/C=C\C(=O)[C@@H](O)[C@@H](O)C[C@H](O)[C@@H](O)c2c(Cl)c(O)cc(O)c2C(=O)O1] |
| 123 | 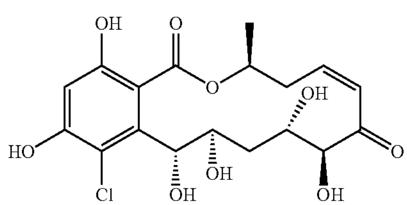 [SMILES: C[C@H]1C/C=C\C(=O)[C@@H](O)[C@@H](O)C[C@@H](O)[C@H](O)c2c(Cl)c(O)cc(O)c2C(=O)O1] |
| 124 | 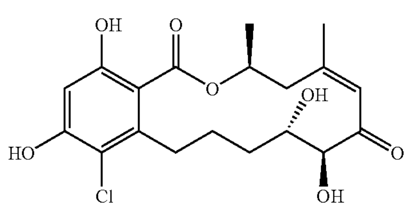 |
| 125 | 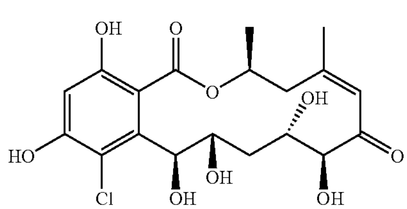 [SMILES: C/C1=C/C(=O)[C@@H](O)[C@@H](O)C[C@H](O)[C@@H](O)c2c(Cl)c(O)cc(O)c2C(=O)O[C@@H](C)C1] |

TABLE 1-continued

| Compound Designation | Structure |
| --- | --- |
| 126 | 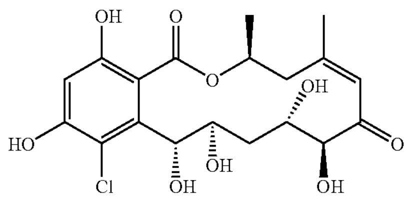 [SMILES: C/C1=C/C(=O)[C@@H](O)[C@@H](O)C[C@@H](O)[C@H](O)c2c(Cl)c(O)cc(O)c2C(=O)O[C@@H](C)C1] |
| 127 | 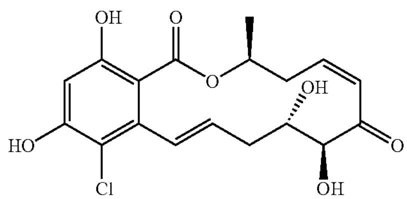 [SMILES: C[C@H]1C/C=C\C(=O)[C@@H](O)[C@@H](O)C/C=C/c2c(Cl)c(O)cc(O)c2C(=O)O1] |
| 128 | 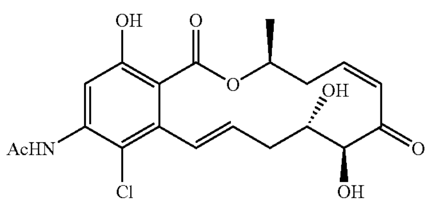 [SMILES: CC(=O)Nc1cc(O)c2c(c1Cl)/C=C/C[C@H](O)[C@H](O)C(=O)/C=C\C[C@H](C)OC2=O] |
| 129 | 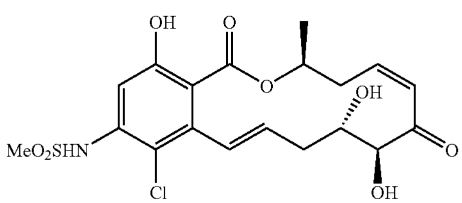 |
| 130 | 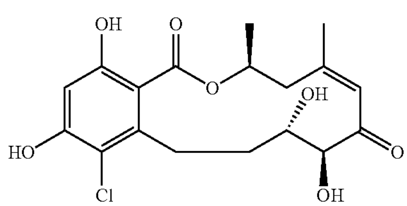 [SMILES: C/C1=C/C(=O)[C@@H](O)[C@@H](O)CCc2c(Cl)c(O)cc(O)c2C(=O)O[C@@H](C)C1] |
| 131 | 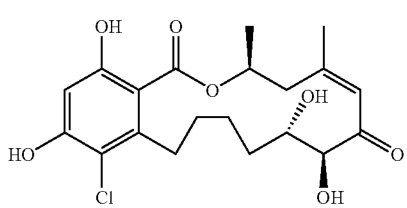 [SMILES: C/C1=C/C(=O)[C@@H](O)[C@@H](O)CCCCc2c(Cl)c(O)cc(O)c2C(=O)O[C@@H](C)C1] |
| 132 | 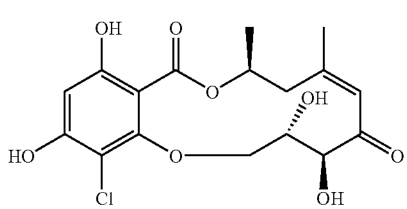 [SMILES: C/C1=C/C(=O)[C@@H](O)[C@@H](O)COc2c(Cl)c(O)cc(O)c2C(=O)O[C@@H](C)C1] |

TABLE 1-continued

| Compound Designation | Structure |
|---|---|
| 133 | 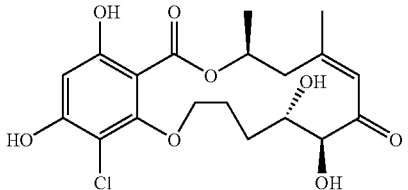 |

In various embodiments, prodrugs of the compounds are provided. Prodrugs of the compounds may be derivatives that may enhance a desired property such as solubility or bioavailability and convert to the parent compound in vivo. In other embodiments, prodrugs may be used to reduce the toxicity of the compounds when administered. Non-limiting examples of suitable prodrugs include esters of the compounds including lower alkyl esters or esters of natural or synthetic amino acid residues.

Pharmaceutically Acceptable Salts and Prodrugs

The terms "pharmaceutically acceptable salt" and "prodrug" are used throughout the specification to describe any pharmaceutically acceptable form (such as a salt, an ester, a phosphate ester, salt of an ester or a related group) of a compound which, upon administration to a patient, provides the compound described in the specification. In cases where compounds are sufficiently basic or acidic to form stable nontoxic acid or base salts, administration of the compounds as salts may be appropriate. The term pharmaceutically acceptable salts or complexes refers to salts or complexes that retain the desired biological activity of the compounds of the present invention and exhibit minimal undesired toxicological effects.

Nonlimiting examples of such salts are (a) acid addition salts formed with inorganic acids such as sulfate, nitrate, bicarbonate, and carbonate salts (for example, hydrochloric acid, hydrobromic acid, sulfuric acid, phosphoric acid, nitric acid, and the like), and salts formed with organic acids including tosylate, methanesulfonate, acetate, citrate, malonate, tartarate, succinate, benzoate, ascorbate, α-ketoglutarate, and α-glycerophosphate salts, such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid; (b) base addition salts formed with metal cations such as zinc, calcium, bismuth, barium, magnesium, aluminum, copper, cobalt, nickel, cadmium, sodium, potassium, lithium and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula $-NR^+A^-$, wherein R is as defined above and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

Pharmaceutically acceptable salts may be obtained using standard procedures well known in the art, for example by reacting a sufficiently basic compound such as an amine with a suitable acid affording a physiologically acceptable anion.

Pharmaceutically acceptable "prodrugs" refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. For example, a suitable prodrug may be an ester, or an amide of a carboxylic acid that is hydrolyzed to form the acid or a phosphoester. Non-limiting examples of prodrugs include, but are not limited to, alkyl or aralkyl esters or amides, including methyl, ethyl, propyl, benzyl and substituted benzyl esters or amides. Prodrugs also comprise phosphate esters of the compounds.

Stereoisomerism and Polymorphism

Compounds of the present invention have chiral centers and may exist in and be isolated in optically active and racemic forms. The present invention encompasses any racemic, optically-active, diastereomeric, polymorphic, or stereoisomeric form, or mixtures thereof, of a compound of the invention, which possesses the useful properties described herein. It is understood that based on the number of asymmetric centers, a total number of $2^\circ$ possible stereochemical isomers is possible. The present invention includes all possible stereochemical configurations of the compounds.

In some embodiments, the stereochemistry of the compounds of the invention will retain the natural stereochemistry of the natural resorcylic acid lactone. For example, the stereochemistry of substituents $R^5$, $R^9$ and $R^{10}$ in the compounds of formulae I, Ia, II, III, IIa or IIb will retain the natural stereochemistry found in radicicol A. In other embodiments, the stereochemical configuration of substituents $R^5$, $R^9$ or $R^{10}$ will be different than that found in radicicol A. It will be understood that the stereochemical configuration of any substitutent at an asymmetric carbon of the compounds can be in the R or S configuration independent of other substitutents at other asymmetric centers in the compound.

The present invention also encompasses all possible stereochemical configurations of asymmetric substituents, such as amino acids. As described above, the naturally occurring a-amino acids in L, D, and D,L configurations are encompassed. Furthermore, all possible stereochemical configurations of non-natural synthetic amino acids are encompassed by the invention.

In one embodiment, the compounds are prepared in optically active form by asymmetric synthesis using the processes described herein or synthetic transformations known to those skilled in the art.

Examples of methods to obtain optically active materials are known in the art, and include at least the following:

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent; or xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

Definitions

Whenever a term in the specification is identified as a range (i.e. $C_{1-4}$ alkyl), the range independently refers to each element of the range. As a non-limiting example, $C_{1-4}$ alkyl means, independently, $C_1$, $C_2$, $C_3$ or $C_4$ alkyl. Similarly, when one or more substituents are referred to as being "independently selected from" a group, this means that each substituent can be any element of that group, and any combination of these groups can be separated from the group. For example, if $R^1$ and $R^2$ can be independently selected from X, Y and Z, this separately includes the groups $R^1$ is X and $R^2$ is X; $R^1$ is X and $R^2$ is Y; $R^1$ is X and $R^2$ is Z; $R^1$ is Y and $R^2$ is X; $R^1$ is Y and $R^2$ is Y; $R^1$ is Y and $R^2$ is Z; $R^1$ is Z and $R^2$ is X; $R^1$ is Z and $R^2$ is Y; and $R^1$ is Z and $R^2$ is Z.

The term "aliphatic" as used herein means straight-chain, branched or cyclic $C_1$-$C_{12}$ hydrocarbons which are completely saturated or which contain one or more units of unsaturation but which are not aromatic. For example, suitable aliphatic groups include substituted or unsubstituted linear, branched or cyclic alkyl, alkenyl, alkynyl groups and hybrids thereof such as (cycloalkyl)alkyl, (cycloalkenyl)alkyl or (cycloalkyl)alkenyl. The terms "alkyl", "alkoxy", "hydroxyalkyl", "alkoxyalkyl", and "alkoxycarbonyl", used alone or as part of a larger moiety, includes both straight and branched chains.

The term "heteroaliphatic" as used herein is intended to have its customary meaning in the art and includes an aliphatic group substituted with one or more atoms other than carbon or hydrogen in the aliphatic chain, nonlimiting examples of which are nitrogen, oxygen, sulfur, phosphorus, silicon or boron.

The term "alkyl" as used herein, is intended to have its customary meaning in the art and includes saturated straight, branched, or cyclic, primary, secondary, or tertiary hydrocarbon including, but not limited to, $C_1$-$C_{12}$ hydrocarbons.

The term "lower alkyl" refers to a saturated straight, branched, or cyclic, primary, secondary, or tertiary hydrocarbon, including groups with $C_1$ to $C_4$, and if appropriate a cyclic alkyl group (for example cyclopropyl).

Illustrative examples of alkyl groups are methyl, ethyl, propyl, isopropyl, cyclopropyl, butyl, secbutyl, isobutyl, tertbutyl, cyclobutyl, 1-methylbutyl, 1,1-dimethylpropyl, pentyl, cyclopentyl, isopentyl, neopentyl, hexyl, isohexyl, and cyclohexyl. Unless otherwise specified, the alkyl group can be unsubstituted or substituted with one or more moieties, including alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, thiol, imine, sulfonic acid, sulfate, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Third Edition, 1999.

The term "halo" or "halogen", as used herein, includes chloro, bromo, iodo, and fluoro.

The term "chiral" as used herein includes a compound that has the property that it is not superimposable on its mirror image.

The term "tautomer" as used herein refers to alternate structures which are recognized in the art to be in equilibrium with the depicted structure. For example, the enol structure below is a tautomer of the ketone structure and recognized to be in equilibrium with the ketone structure.

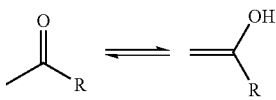

As used herein, the term "solvate" or "pharmaceutically acceptable solvate," is a solvate formed from the association of one or more solvent molecules to one or more molecules of a compound of any one of formulae I, Ia, Ib, II, III, IIa or IIb or the compounds depicted in Table 1. The term solvate includes hydrates (e.g., hemi-hydrate, mono-hydrate, dihydrate, trihydrate, tetrahydrate, and the like).

The term "alkylsulfonyl" means a straight or branched alkylsulfone of the number of carbon atoms specified, as for example, $C_{1-6}$ alkylsulfonyl or methylsulfonyl.

The terms "alkenyl" and "alkynyl" as used herein are intended to have their standard meaning in the art, including both substituted and unsubstituted forms. Thus, $C_{2-6}$ alkenyl may be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl. Similarly, $C_{2-6}$ alkynyl may be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

The term "aryl" as used herein is intended to have its customary meaning in the art, and includes any stable monocyclic, bicyclic, or tricyclic carbon ring, wherein at least one ring is aromatic as defined by the Huckel 4n+2 rule, and especially phenyl, biphenyl, or naphthyl. The term includes both substituted and unsubstituted moieties. The aryl group can be substituted with any described moiety including, but not limited to, one or more moieties selected from the group consisting of halogen (fluoro, chloro, bromo or iodo), hydroxyl, amino, azido, alkylamino, arylamino, alkoxy, aryloxy, nitro, cyano, sulfonic acid, sulfate, phosphonic acid, phosphate, or phosphonate, either protected or unprotected as necessary, as known to those skilled in the art, for example, as taught in Greene et al., *Protective Groups in Organic Synthesis*, John Wiley & Sons, 3rd Ed., 1999.

The term "alkaryl" or "alkylaryl" refers to an alkyl group with an aryl substituent or an alkyl group linked to the molecule through an aryl group as defined herein. The term "aralkyl" or "arylalkyl" refers to an aryl group substituted with an alkyl substituent or linked to the molecule through an alkyl group as defined above.

The term "cycloalkyl" includes a ring of $C_{3-8}$, including, but not limited to, cyclopropyl, cyclobutyl, cyclopentyl, cyclohexyl, cycloheptyl and cyclooctyl.

The term "alkoxy" means a straight or branched chain alkyl group having an attached oxygen radical, the alkyl group having the number of carbons specified or any number within this range. For example, a "—O-alkyl", $C_{1-4}$ alkoxy, methoxy, etc.

The term "acyl" includes a group of the formula C(O)R', wherein R' is a straight, branched, or cyclic alkyl (including lower alkyl), carboxylate residue of an amino acid, aryl including phenyl, heteroaryl, alkaryl, aralkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, alkyl or alkoxy, sulfonate esters such as alkyl or aralkyl sulphonyl including methanesulfonyl, the mono, di or triphosphate ester, trityl or monomethoxytrityl, substituted benzyl, alkaryl, aralkyl including benzyl, alkoxyalkyl including methoxymethyl, aryloxyalkyl such as phenoxymethyl. Aryl groups optimally comprise a phenyl group. In nonlimiting embodiments, acyl groups include acetyl, trifluoroacetyl, methylacetyl, cyclopropylacetyl, cyclopropyl, carboxy, propionyl, butyryl, isobutyryl, hexanoyl, heptanoyloctanoyl, neo-heptanoyl, phenylacetyl, 2-acetoxy-2-phenylacetyl, diphenylacetyl, α-methoxy-α-trifluoromethyl-phenylacetyl, bromoacetyl, 2-nitro-benzeneacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoro-heptanoyl, 7H-dodeca-fluoroheptanoyl, 7-chlorododecafluoro-heptanoyl, 7-chloro-dodecafluoro-heptanoyl, 7H-dodecafluoroheptanoyl, 7H-dodeca-fluoroheptanoyl, nona-fluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6-dichloro-2-methoxy-benzoyl, 4-(1,1,2,2-tetrafluoro-ethoxy)-benzoyl, 2-bromo-propionyl, omega-aminocapryl, decanoyl, n-pentadecanoyl, stearyl, 3-cyclopentyl-propionyl, 1-benzene-carboxyl, O-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidinecarbonyl, 4-phenylbenzoyl.

The term "ester" includes a group of the structure "—C(=O)—O—R'" or "—O—C(=O)—R'", wherein R' is a straight, branched, or cyclic alkyl (including lower alkyl), carboxylate residue of an amino acid, aryl including phenyl, heteroaryl, alkaryl, aralkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxy-trityl, substituted benzyl, alkaryl, aralkyl including benzyl, alkoxyalkyl including methoxymethyl, aryloxyalkyl such as phenoxymethyl. Aryl groups optimally comprise a phenyl group.

The term "heteratom" includes an atom other than carbon or hydrogen in the structure of a group, nonlimiting examples of which are nitrogen, oxygen, sulfur, phosphorus, silicon or boron.

The term "heterocycle", "heterocyclyl", or "heterocyclic" as used herein includes non-aromatic ring systems having four to fourteen members, preferably five to ten, in which one or more ring carbons, preferably one to four, are each replaced by a heteroatom. Examples of heterocyclic rings include 3-1H-benzimidazol-2-one, (1-substituted)-2-oxo-benzimidazol-3-yl, 2-tetrahydro-furanyl, 3-tetrahydrofuranyl, 2-tetrahydropyranyl, 3-tetrahydropyranyl, 4-tetra-hydropyranyl, [1,3]-dioxalanyl, [1,3]-dithiolanyl, [1,3]-dioxanyl, 2-tetrahydro-thiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, 3-furazanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 2-pyrazolyl, 3-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, and benzoisoxazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to rings that are optionally substituted. The term "heteroaryl" may be used interchangeably with the term "heteroaryl ring" or the term "heteroaromatic".

The term "amino" as used herein unless otherwise specified, includes a moiety represented by the structure "—N(R)$_2$", and includes primary, secondary and tertiary amines optionally substituted by alkyl, aryl, heterocyclyl, and/or sulfonyl groups. Thus (R)$_2$ may represent two hydrogen atoms, two alkyl moieties, or one hydrogen and one alkyl moiety.

The term "quaternary amine" as used herein includes quaternary ammonium salts that have a positively charged nitrogen. They are formed by the reaction between a basic nitrogen in the compound of interest and an appropriate quaternizing agent such as, for example, methyliodide or benzyliodide. Appropriate counterions accompanying a quaternary amine include acetate, trifluoroacetate, chloro, bromo and iodo ions.

The term "substituted" includes multiple degrees of substitution by one or more named substituents in various types of groups. Suitable substituents of the above-described aliphatic, aryl, heteroaryl and other moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R; —CO$_2$(R); —CON(R)$_2$; —OC(O)R; —OCO$_2$R; —OCON(R)$_2$; —N(R)$_2$; —S(O)$_2$R; —NR(CO)R wherein each occurrence of R independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein. Where multiple substituent possibilities exist, the compound can be substituted by one or more of the disclosed or claimed substituent groups, independently from one another, and taken singly or in plural.

The term "leaving group" is intended to have its ordinary meaning in the art and includes groups that are easily displaced in a substitution reaction or that stabilize a negative charge. Examples of leaving groups include, but are not limited to, halogen atoms, esters, alkyl or aryl sulfonyl, activated esters and the like.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term "protecting group" as used herein refers to a group that may be attached to a reactive group, including heteroatoms such as oxygen or nitrogen, to prevent the reactive group from participating in a reaction. Any protecting groups taught in Greene, et al., *Protective Groups in Organic Synthesis*, John Wiley and Sons, Third Edition, 1999, may be used. Examples of suitable protecting groups include, but are not limited to, alkoxyalkyl groups such as ethoxymethyl and methoxymethyl; silyl protecting groups, such tert-butyldimethyl silyl (TBS), phenyldimethylsilyl, trimethylsilyl (TMS), 2-trimethylsilyl-ethoxymethyl (SEM) and 2-trimethylsilylethyl; and benzyl and substituted benzyl.

It should be understood that the various possible stereoisomers of the groups mentioned above and herein are within the meaning of the individual terms and examples, unless otherwise specified. As an illustrative example, "1-methyl-butyl" exists in both (R) and the (S) form, thus, both (R)-1-methyl-butyl and (S)-1-methyl-butyl is covered by the term "1-methyl-butyl", unless otherwise specified.

The term "patient" includes human and veterinary subjects.

An "effective amount" is the quantity of compound in which a beneficial outcome is achieved when the compound is administered to a patient or alternatively, the quantity of compound that possesses a desired activity in vivo or in vitro. In the case of proliferative disorders, a beneficial clinical outcome includes reduction in the extent or severity of the symptoms associated with the disease or disorder and/or an increase in the longevity and/or quality of life of the patient compared with the absence of the treatment. For example, for a subject with cancer, a "beneficial clinical outcome" includes a reduction in tumor mass, a reduction in the rate of tumor growth, a reduction in metastasis, a reduction in the severity of the symptoms associated with the cancer and/or an increase in the longevity of the subject compared with the absence of the treatment. The precise amount of compound administered to a subject will depend on the type and severity of the disease or condition and on the characteristics of the patient, such as general health, age, sex, body weight and tolerance to drugs. It will also depend on the degree, severity and type of proliferative disorder. The skilled artisan will be able to determine appropriate dosages depending on these and other factors.

The term "kinase-inhibiting amount" as used herein, refers to an amount of the compound that inhibits a kinase enzyme compared to a control as tested by the methods described herein.

The term "cancer" includes, but is not limited to, solid tumors and blood borne tumors and include, but is not limited to, the following cancers: breast, ovary, cervix, prostate, testis, genitourinary tract, esophagus, larynx, glioblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia. The term "cancer" includes primary cancer, cancers secondary to treatment, and metastatic cancers.

The term "pharmaceutically acceptable carrier" refers to a non-toxic carrier, adjuvant, or vehicle that may be administered to a patient, together with a compound of this invention, and which does not destroy the pharmacological activity thereof.

The terms "GSK-3-mediated disease, or "GSK-3-mediated condition", as used herein, mean any disease or other deleterious condition or state in which GSK-3 is known to play a role. Such diseases or conditions include, without limitation, diabetes, Alzheimer's disease, Huntington's Disease, Parkinson's Disease, AIDS-associated dementia, amyotrophic lateral sclerosis (AML), multiple sclerosis (MS), schizophrenia, cardiomycete hypertrophy, reperfusion/ischemia, and baldness.

The terms "CDK-2-mediated disease" or CDK-2-mediated condition", as used herein, mean any disease or other deleterious condition in which CDK-2 is known to play a role. The terms "CDK-2-mediated disease" or "CDK-2-mediated condition" also mean those diseases or conditions that are alleviated by treatment with a CDK-2 inhibitor. Such conditions include, without limitation, cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis, such as are described for example in Fischer, P. M. and Lane, D. P., Current Medicinal Chemistry, 7, 1213-1245 (2000); Mani, S., Wang, C., Wu, K., Francis, R. and Pestell, R., Exp. Opin. Invest. Drugs, 9, 1849 (2000); Fry, D. W. and Garrett, M. D., Current Opinion in Oncologic, Endocrine & Metabolic Investigational Drugs, 2, 40-59 (2000).

The terms "ERK-mediated disease" or "ERK-mediated condition", as used herein mean any disease or other deleterious condition in which ERK may play a role. The terms "ERK-2-mediated disease" or "ERK-2-mediated condition" also mean those diseases or conditions that are alleviated by treatment with a ERK-2 inhibitor. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases. ERK-2 protein kinase and its implication in various diseases has been described for example in Bokemeyer et al. 1996, Kidney Int. 49, 1187; Anderson et al., 1990, Nature 343, 651; Crews et al., 1992, Science 258, 478; Bjorbaek et al., 1995, J. Biol. Chem. 270, 18848; Rouse et al., 1994, Cell 78, 1027; Raingeaud et al., 1996, Mol. Cell. Biol. 16, 1247; Raingeaud et al. 1996; Chen et al., 1993 Proc. Natl. Acad. Sci. USA 90, 10952; Oliver et al., 1995, Proc. Soc. Exp. Biol. Med. 210, 162; Moodie et al., 1993, Science 260, 1658; Frey and Mulder, 1997, Cancer Res. 57, 628; Sivaraman et al., 1997, J. Clin. Invest. 99, 1478; Whelchel et al., 1997, Am. J. Respir. Cell Mol. Biol. 16, 589.

The terms "AKT-mediated disease" or "AKT-mediated condition", as used herein, mean any disease or other deleterious condition in which AKT is known to play a role. The terms "AKT-mediated disease" or "AKT-mediated condition" also mean those diseases or conditions that are alleviated by treatment with an AKT inhibitor. AKT-mediated diseases or conditions include, but are not limited to, proliferative disorders, cancer, and neurodegenerative disorders. The association of AKT, also known as protein kinase B, with various diseases has been described for example in Khwaja, A., Nature, pp. 33-34, 1990; Zang, Q. Y., et al, Oncogene, 19 2000; Kazuhiko, N., et al, The Journal of Neuroscience, 20 2000.

The terms "Src-mediated disease" or "Src-mediated condition", as used herein mean any disease or other deleterious condition in which Src is known to play a role. The terms "Src-mediated disease" or "Src-mediated condition" also mean those diseases or conditions that are alleviated by treatment with a Src inhibitor. Such conditions include, without limitation, hypercalcemia, osteoporosis, osteoarthritis, cancer, symptomatic treatment of bone metastasis, and Paget's disease. Src protein kinase and its implication in various diseases has been described for example in Soriano, Cell, 69, 551 (1992); Soriano et al., Cell, 64, 693 (1991); Takayanagi, J. Clin. Invest., 104, 137 (1999); Boschelli, Drugs of the Future 2000, 25(7), 717, (2000); Talamonti, J. Clin. Invest., 91, 53 (1993); Lutz, Biochem. Biophys. Res. 243, 503 (1998); Rosen, J. Biol. Chem., 261, 13754 (1986); Bolen, Proc. Natl. Acad. Sci. USA, 84, 2251 (1987); Masaki, Hepatology, 27, 1257 (1998); Biscardi, Adv. Cancer Res., 76, 61 (1999); Lynch, Leukemia, 7, 1416 (1993); Wiener, Clin. Cancer Res., 5, 2164 (1999); Staley, Cell Growth Diff., 8, 269 (1997).

The terms "Lck-mediated disease" or "Lck-mediated condition", as used herein, mean any disease state or other deleterious condition in which Lck is known to play a role. The terms "Lck-mediated disease" or "Lck-mediated condition" also mean those diseases or conditions that are alleviated by treatment with an Lck inhibitor. Lck-mediated diseases or conditions include, but are not limited to, autoimmune diseases such as transplant rejection, allergies, rheumatoid arthritis, and leukemia. The association of Lck with various diseases has been described for example in Molina et al., Nature, 357, 161 (1992).

The terms "Abl-mediated disease" or "Abl-mediated condition", as used herein, mean any disease state or other deleterious condition in which Abl is known to play a role. The terms "Abl-mediated disease" or "Abl-mediated condition" also mean those diseases or conditions that are alleviated by treatment with an Abl inhibitor. Abl-mediated diseases or conditions include, but are not limited to, leukemias, particularly chronic myeloid leukemia. The association of Abl with various diseases has been described for example in Druker, et al., *N. Engl. J. Med.* 2001, 344, 1038-1042.

The terms "cKit-mediated disease" or "cKit-mediated condition", as used herein, mean any disease state or other deleterious condition in which cKit is known to play a role. The terms "cKit-mediated disease" or "cKit-mediated condition" also mean those diseases or conditions that are alleviated by treatment with an cKit inhibitor. cKit-mediated diseases or conditions include, but are not limited to, mastocytosis/mast cell leukemia, gastrointestinal stromal tumor, sinonasal natural killer/T-cell lymphoma, seminoma/dysgerminoma, thyroid carcinoma, small-cell lung carcinoma, malignant melanoma, adenoid cystic carcinoma, ovarian carcinoma, acute myelogenious leukemia, anaplastic large-cell lymphoma, angiosarcoma, endometrial carcinoma, pediatric T-cell ALLllymphoma, breast carcinoma and prostate carcinoma. The association of cKit with various diseases has been described for example in Heinrich, et al., *J. Clinical Oncology* 2002, 20, 1692-1703.

The terms "Flt3-mediated disease" or "Flt3-mediated condition", as used herein, mean any disease state or other deleterious condition in which Flt3 is known to play a role. The terms "Flt3-mediated disease" or "Flt3-mediated condition" also mean those diseases or conditions that are alleviated by treatment with an Flt3 inhibitor. Flt3-mediated diseases or conditions include, but are not limited to, acute myelogenous leukemia, mixed lineage leukemia and acute lymphocytic leukemia. The association of Flt3 with various diseases has been described for example in Sternberg and Licht, *Curr. Opin Hematol.* 2004, 12, 7-13.

The terms "KDR-mediated disease" or "KDR-mediated condition", as used herein, mean any disease state or other deleterious condition in which KDR is known to play a role. The terms "KDR-mediated disease" or "KDR-mediated condition" also mean those diseases or conditions that are alleviated by treatment with an KDR inhibitor. KDR-mediated diseases or conditions include, but are not limited to, carcinoma of the lung, breast, gastrointestinal tract, kidney, bladder, ovary and endometrium, intracranial tumors including glioblastoma multiforme, sporadic capillary hemangioblastoma, hematological malignancies, including T cell lymphoma, acute lymphoblastic leukemia, Burkitt's lymphoma and promyelocytic leukemia, age-related macular degeneration, herpetic ocular disease, rheumatoid arthritis, cerebral ischemia and endometriosis. The association of KDR with various diseases has been described for example in Ferrara, *Endocrine Reviews* 2004, 25, 581-611.

Method of Treatment

The compounds described herein, are particularly useful for the treatment or prevention of a disorder mediated by kinases or mediated by phosphatases, including ATPases. Accordingly, the present invention provides methods for the treatment of diseases mediated by kinases or phosphatases, comprising administering to a patient with a kinase-mediated or phosphatase-mediated disease an effective amount of a radicicol A analogue, optionally in combination with a pharmaceutically acceptable carrier. In one embodiment, the compounds described herein are useful for the treatment or prevention of a proliferative disorder, including cancer metastasis. In another embodiment, the compounds described herein, are useful for the treatment or prevention of an inflammatory disorder associated by kinases or phosphatases. In still other embodiments, the compounds of the invention are useful for the treatment or prevention of a disorder associated with angiogenesis. In still other embodiments, the inventive compounds are useful for the treatment of autoimmune disorders or neurodegenerative disorders.

Macrocycles related to radicicol A have been shown to be potent inhibitors of NF-κβ activation, AP-1 activation and protein kinases (for example, MEKK, MEK1, PDGFr, VEGFr and the like). Based on these mechanisms of action, the compounds inhibit the production of various pro-inflammatory and/or immunologic cytokines such as TNF-α, IL-1, IL-6, IL-8, IL-2 etc, and also inhibit the production of various pro-inflammatory molecules under the regulation of NF-κβ pathway such as prostaglandins produced from COX-2, ICAM-1 and MMP-1 and 3 etc. In addition, macrocycles related to radicicol A have ability to inhibit cell proliferation under the regulation of AP-1 pathway through the inhibition of MEK1. The compounds of the invention have the ability to inhibit angiogenesis based on the inhibitory activities on VEGFr and PDGFr kinases. Thus, the compounds of the invention, and pharmaceutical compositions thereof, are useful as anti-inflammatory and/or immunosuppressive agents for the treatment of various inflammatory diseases, and abnormal cell proliferation or as antiangiogenesis agents for the treatment of cancer. In certain embodiments, the compounds of the present invention can be used for the treatment of diseases and disorders including, but not limited to, sepsis, rheumatoid arthritis, psoriatic arthritis, osteoarthritis, inflammatory bowel disease (Crohn's disease and ulcerative colitis), multiple sclerosis, atopic dermatitis, psoriasis, asthma, osteoporosis, allergic rhinitis, ocular inflammation, hepatitis, autoimmune disorders, systemic lupus erthematosus, allograft rejection/graft versus host disease, diabetes, AIDS, solid tumor cancers, leukemia, lymphomas, non-Hodgkin's B-cell lymphomas, chronical lymphocytic leukemia (CLL), multiple myeloma, eczema, urticaria, myasthenia gravis, idiopathic thrombocytopenia purpura, cardiovascular disease (e.g., myocardial infarction, atherosclerosis), hepatitis, glomerulonephropathy, productive nephritis, adenovirus, diseases/disorders of the central nervous system (e.g., stroke, Alzheimer's disease, epilepsy) and for the treatment of the symptoms of malaria, to name a few. The inventive compounds also find use in the prevention of restenosis of blood vessels subject to traumas such as angioplasty and stenting.

An aspect of the invention relates to compounds and compositions that are useful for treating cancer.

Another aspect of the invention relates to the treatment of the following cancers: breast, ovary, cervix, prostate, testis, genitourinary tract, esophagus, larynx, glioblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

Another aspect of the invention is a method for treating cancer comprising administering an effective amount of a compound of formulae I, Ia, Ib, II, IIa, IIb or III described herein to a patient with cancer.

Angiogenesis is characterized by the proliferation of endothelial cells to form new blood vessels (often called neovascularization). Inhibition of mitosis of endothelial cells results in inhibition of angiogenesis. Another aspect of this invention relates to inhibition of undesirable mitosis, including undesirable angiogenesis. A mammalian disease characterized by undesirable cell mitosis as defined herein includes, but is not limited to, excessive or abnormal stimulation of endothelial cells (e.g., atherosclerosis), solid tumors and tumor metastasis, benign tumors, for example, hemangiomas, trachomas, and pyogenic granulomas, vascular malfunctions, abnormal wound healing, inflammatory and immune disorders, Bechet's disease, gout or gouty arthritis, abnormal angiogenesis accompanying rheumatoid arthritis, skin diseases, such as psoriasis, diabetic retinopathy and other ocular angiogenic diseases such as retinopathy of prematurity (retrolental fibroplasic), macular degeneration, corneal graft rejection, neovascular glaucoma and Osler Weber syndrome (Osler-Weber-Rendu disease).

Other undesired angiogenesis involves normal processes including ovulation and implantation of a blastula. The compositions described above can be used as a birth control agent by reducing or preventing uterine vascularization required for embryo implantation. Accordingly, the compositions described above can be used to block ovulation and implantation of a blastula or to block menstruation (induce amenorrhea).

Diseases associated with undesirable mitosis including neovascularization can be treated according to the present invention. Such diseases include, but are not limited to, ocular neovascular disease, diabetic retinopathy, retinopathy of prematurity, corneal graft rejection, neovascular glaucoma and retrolental fibroplasias, epidemic keratoconjunctivitis, Vitamin A deficiency, contact lens overwear, atopic keratitis, superior limbic keratitis, pterygium keratitis sicca, Sjögren's syndrome, acne rosacea, phylectenulosis, syphilis, *Mycobacteria* infections, lipid degeneration, chemical burns, bacterial ulcers, fungal ulcers, *Herpes simplex* infections, *Herpes zoster* infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, Scleritis, Steven-Johnson disease, pemphigoid, radial keratotomy, and corneal graph rejection.

Other diseases associated with undesirable mitosis including neovascularization can be treated according to the present invention. Such diseases include, but are not limited to, sickle cell anemia, sarcoid, pseudoxanthoma elasticum, Paget's disease, vein occlusion, artery occlusion, carotid obstructive disease, chronic uveitis/vitritis, Lyme's disease, systemic lupus erythematosis, Eales' disease, Bechet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, and post-laser complications. Other diseases include, but are not limited to, diseases associated with rubeosis (neovascularization of the iris and the angle) and diseases caused by the abnormal proliferation of fibrovascular or fibrous tissue including all forms of proliferative vitreoretinopathy, whether or not associated with diabetes.

Another aspect of the invention relates to the treatment of inflammatory diseases including, but not limited to, excessive or abnormal stimulation of endothelial cells (e.g., atherosclerosis), solid tumors and tumor metastasis, benign tumors, for example, hemangiomas, acoustic neuromas, trachomas, and pyogenic granulomas, vascular malfunctions, abnormal wound healing, inflammatory and immune disorders, Bechet's disease, gout or gouty arthritis, abnormal angiogenesis accompanying rheumatoid arthritis, skin diseases, such as psoriasis, diabetic retinopathy and other ocular angiogenic diseases such as retinopathy of prematurity (retrolental fibroplasic), macular degeneration, corneal graft rejection, neovascular glaucoma and Osler Weber syndrome (Osler-Weber-Rendu disease). Other undesired angiogenesis involves normal processes including ovulation and implantation of a blastula. Accordingly, the compositions described above can be used to block ovulation and implantation of a blastula or to block menstruation (induce amenorrhea).

In general, the present invention provides compounds useful for the treatment of inflammatory or autoimmune disorders. Published International Patent Application WO 03/076424, which is hereby incorporated by reference in its entirety, discloses that radicicol A analogues inhibit NF-κB activity. Without wishing to be bound by any particular theory, more generally, the inhibition of NF-κB activity and the identification of NF-κB as a key player in the pathogenesis of inflammation suggest that NF-κB targeted therapeutics may be effective in inflammatory and immune disorders (see, generally, NF-κB in Defense and Disease, J. Clin. Investig. 2001, 107, 7).

As discussed above, analogues of radicicol A and related resorcylic acid lactones exhibit immunomodulatory activity and exhibit activity for the inhibition of angiogenesis through inhibition of receptor tyrosine kinases. As such, the inventive compounds as useful for the treatment of a variety of disorders, including, but not limited to, sepsis, glomerulonephropathy, rheumatoid arthritis (including ankylosing spondylitis), psoriatic arthritis, osteoarthritis, osteoporosis, allergic rhinitis, ocular inflammation, inflammatory bowel disease, atopic dermatitis, psoriasis, asthma, Crohn's disease, ulcerative colitis, inflammatory pulmonary disease, hepatitis, autoimmune disorders, diabetes, AIDS, solid tumor cancers, Leukemia, lymphomas, non-hodgkin's B-cell lymphomas, chronical lymphocytic leukemia (CLL), multiple myeloma, systemic lupus erythematosus, allograft rejection/graft versus host disease, eczema, uticaria, myasthenia gravis, idiopathic thrombocytopenia purpura, cardiovascular disease (e.g., myocardial infarction, atherosclerosis), hepatitis, productive nephritis, adenovirus, diseases/disorders of the central nervous system (stroke, Alzheimer's disease, epilepsy) and for the treatment of the symptoms of malaria, to name a few. In certain embodiments, compounds of the invention are particularly useful for the treatment of rheumatoid arthritis, psoriasis, multiple sclerosis, asthma and cancer.

Rheumatoid arthritis is a chronic syndrome characterized by nonspecific, usually symmetric inflammation of the peripheral joints, potentially resulting in progressive destruction of articular and periarticular structures, with or without generalized manifestations (See, generally, The Merck Manual, 1999, Seventeenth Ed. Merck & Co., the entire contents of which are hereby incorporated by reference). Studies in the past established that presence of inflammatory cells and pro-inflammatory cytokines, such as TNFα, IL-1β are abundant in the diseased synovium. Increased macrophage-derived lining cells are prominent along with some lymphocytes and vascular changes in early disease. Although there is not a cure, reduction of circulatory pro-inflammatory cytokines (e.g. TNFα, IL-1β) through intervention of biological agents, such as Enbrel, Remicade or Anakinra, demonstrated efficacy in reduction of symptoms and retarding the disease progression in clinical trials. Thus, developing of an agent such as described herein in modulation of pro-inflammatory cytokines through NF-κB inhibition could bring great benefit to RA patients.

Psoriasis is a disorder for which there is no curative therapy, although in most cases acute attacks can be controlled. Psoriasis is a chronic, recurrent disease characterized by dry, well-circumscribed, silvery, scaling papules and plaques of various sizes, and has traditionally been attributed to increased epidermal cell proliferation and concomitant dermal inflammation. The response of psoriasis to the immunosuppressive drug cyclosporine suggests that the primary pathogenic factor may be immunologic. Proliferation of epidermal cells has been also linked to AP-1 activation via stimulation from injury, radiation or stress to the skin (see, P. Angel et al., "Function and regulation of AP-1 subunits in skin physiology and pathology", Oncogene, 2001, 20:2413-2423; and A. Grandjean-Laquerriere et al., "Relative contribution of NF-κB and AP-1 in the modulation by Curcumin and pyrrolidine dithiocarbamate of the UVB-induced cytokine expression by keratinocytes", Cytokine, 2002, 18(3): 168-177, each of which is hereby incorporated by reference in its entirety). Currently available treatment regimens for psoriasis include the use of lubricants, keratolytics, topical cortisosteroids, sunlight, topical vitamin D derivatives, anthralin, and systemic antimetabolites (e.g., methotrexate), immunosuppressive drugs (e.g., cyclosporine, tacrolimus, mycophenolate, and mofetil). However, immunosuppressive drugs are not yet approved for the treatment of psoriasis and other drugs, including corticosteroids, have severe side effects, including exacerbations or pustular lesions (see, generally, The Merck Manual, 1999, Seventeenth Ed. Merck & Co., the entire contents of which are hereby incorporated by reference). This invention is certainly applicable to this disease as well as a host of other related diseases, such as, psoriatic arthritis, ankylosing spondylitis, just to name a few.

In one embodiment of the invention, methods for the treatment or prevention of infectious disease, including diseases caused by bacterial and parasitic agents, is provided comprising administering an effective amount of the inventive radicicol A analogues. In another embodiment, methods for the treatment and prevention of malaria and mycobacterial diseases comprising administering to a patient with the disease an effective amount of a radicicol A analogue of the invention are provided. In one embodiment, the mycobacterial disease is tuberculosis.

Parasitic protozoa infecting humans have a significant impact on public health, especially in developing countries. Furthermore, several protozoan species are major pathogens of domestic animals. Moreover, in many cases, the parasites have developed resistance to available chemotherapeutic agents. It has been found that protein kinases of parasitic microbes diverge significantly from their counterparts in higher eukaryotes. Given that many protein kinases are essential for the survival of parasites, inhibition of parasitic protein kinases may lead to methods of treatment against infectious disease, including parasitic diseases such as malaria (Doerig et al., Cell. Mol. Biol. Lett., vol. 8(2A), 2003). In this light, inhibition of parasitic protein kinases is being pursued to develop anti-parasitic drugs.

Kinase inhibitors also show promise against bacterial infections. For example, mycobacterium tuberculosis PknB is an essential protein kinase involved in cell growth control of tuberculosis mycobacterium. It has been demonstrated that motoxantrone, an anthraquinone derivative used in cancer therapy, is a PknB inhibitor capable of preventing mycobacterial growth (Wehenkel et al., FEBS Letters, vol. 580, issue 13, 3018-3022). Kinase inhibitors have also been shown to affect the ability of some pathogenic bacteria to invade mammalian cells (Rosenshine et al., Infect. Immun. 1992, 60(6), 2211-2217).

In another embodiment, methods for the treatment or prevention of neurodegenerative disorders comprising administering an effective amount of the radicicol a analogues of the invention are provided. neurodegenerative diseases treatable with the inventive compounds include, but are not limited to, Huntington's disease, polyglutamine disease, Parkinson's disease, Alzheimer's disease, seizures, striatonigral degeneration, progressive supranuclear palsy, torsion dystonia, spasmodic torticollis and dyskinesis, familial tremor, Gilles de la Tourette syndrome, diffuse Lewy body disease, progressive supranuclear palsy, Pick's disease, intracerebral hemorrhage, primary lateral sclerosis, spinal muscular atrophy, amyotrophic lateral sclerosis, hypertrophic interstitial polyneuropathy, retinitis pigmentosa, hereditary optic atrophy, hereditary spastic paraplegia, progressive ataxia and Shy-Drager syndrome; degenerative diseases of the eye, including glaucoma, age-related macular degeneration or rubeotic glaucoma.

Another aspect of this invention relates to a method of inhibiting Aurora A activity in a patient, comprising administering to a patient an effective amount of a compound of formulae I, Ia, Ib, II, IIa, IIb or III, or a pharmaceutically acceptable salt or prodrug thereof.

Another aspect of this invention relates to a method of treating or preventing a GSK-3-mediated disease with a GSK-3 inhibitor, comprising administering to a patient an effective amount of a compound of formulae I, Ia, Ib, II, IIa, IIb or III, or a pharmaceutically acceptable salt or prodrug thereof.

One aspect of this invention relates to a method of enhancing glycogen synthesis and/or lowering blood levels of glucose in a patient in need thereof, which method comprises administering to the patient a therapeutically effective amount of a compound of formulae I, Ia, Ib, II, IIa, IIb or III, or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of the invention relates to inhibiting GSK-3 activity in a biological sample, which method comprises contacting the biological sample with a GSK-3 inhibitor of formulae I, Ia, Ib, II, IIa, IIb or III.

Another aspect of this invention relates to a method of inhibiting GSK-3 activity in a patient comprising administering to the patient a compound of formulae I, Ia, Ib, II, IIa, IIb or or a composition comprising said compound.

Another aspect of this invention relates to a method of treating or preventing a CDK-2-mediated disease comprising administering to a patient in need of such a treatment a therapeutically effective amount of a compound of formulae I, Ia, Ib, II, IIa, IIb or III, or a pharmaceutical composition thereof.

Another aspect of the invention relates to inhibiting CDK-2 activity in a biological sample or a patient, which method comprises administering to the patient a compound of formulae I, Ia, Ib, II, IIa, IIb or III, or a composition comprising said compound.

Another aspect of this invention relates to a method of treating or preventing an ERK-2-mediated disease comprising administering to a patient in need of such a treatment a therapeutically effective amount of a compound of formulae I, Ia, Ib, II, IIa, IIb or III, or a pharmaceutical composition thereof.

Another aspect of the invention relates to inhibiting ERK-2 activity in a biological sample or a patient, which method comprises administering to the patient a compound of formulae I, Ia, Ib, II, IIa, IIb or III, or a composition comprising said compound.

Another aspect of this invention relates to a method of treating or preventing an AKT-mediated disease comprising administering to a patient in need of such a treatment a therapeutically effective amount of a compound of formulae I, Ia, Ib, II, IIa, IIb or III, or a pharmaceutical composition thereof.

Another aspect of the invention relates to inhibiting AKT activity in a biological sample or a patient, which method comprises administering to the patient a compound of formulae I, Ia, Ib, II, IIa, IIb or III, or a composition comprising said compound.

Another aspect of this invention relates to a method of treating or preventing a Src-mediated disease comprising administering to a patient in need of such a treatment a therapeutically effective amount of a compound of formulae I, Ia, Ib, II, IIa, IIb or III, or a pharmaceutical composition thereof.

Another aspect of the invention relates to inhibiting Src activity in a biological sample or a patient, which method comprises administering to the patient a compound of formulae I, Ia, Ib, II, IIa, IIb or III, or a composition comprising said compound.

Another aspect of this invention relates to a method of treating or preventing an Lck-mediated disease with an Lck inhibitor, which method comprises administering to a patient in need of such a treatment a therapeutically effective amount of a compound of formulae I, Ia, Ib, II, IIa, IIb or III, or a pharmaceutical composition thereof.

Another aspect of the invention relates to inhibiting Lck activity in a biological sample or a patient, which method comprises administering to the patient a compound of formulae I, Ia, Ib, II, IIa, IIb or III, or a composition comprising said compound.

Another aspect of this invention relates to a method of treating or preventing an Abl-mediated disease with an Abl inhibitor, which method comprises administering to a patient in need of such a treatment a therapeutically effective amount of a compound of formulae I, Ia, Ib, II, IIa, IIb or III, or a pharmaceutical composition thereof.

Another aspect of the invention relates to inhibiting Abl activity in a biological sample or a patient, which method comprises administering to the patient a compound of formulae I, Ia, Ib, II, IIa, IIb or III, or a composition comprising said compound.

Another aspect of this invention relates to a method of treating or preventing a cKit-mediated disease comprising administering to a patient in need of such a treatment a therapeutically effective amount of a compound of formulae I, Ia, Ib, II, IIa, IIb or III, or a pharmaceutical composition thereof.

Another aspect of the invention relates to inhibiting cKit activity in a biological sample or a patient, which method comprises administering to the patient a compound of formulae I, Ia, Ib, II, IIa, IIb or III, or a composition comprising said compound.

Another aspect of this invention relates to a method of treating or preventing a Flt3-mediated disease comprising administering to a patient in need of such a treatment a therapeutically effective amount of a compound of formulae I, Ia, Ib, II, IIa, IIb or III, or a pharmaceutical composition thereof.

Another aspect of the invention relates to inhibiting Flt3 activity in a biological sample or a patient, which method comprises administering to the patient a compound of formulae I, Ia, Ib, II, IIa, IIb or III, or a composition comprising said compound.

Another aspect of this invention relates to a method of treating or preventing a KDR-mediated disease comprising administering to a patient in need of such a treatment a therapeutically effective amount of a compound of formulae I, Ia, Ib, II, IIa, IIb or III, or a pharmaceutical composition thereof.

Another aspect of the invention relates to inhibiting KDR activity in a biological sample or a patient, which method comprises administering to the patient a compound of formulae I, Ia, Ib, II, IIa, IIb or III, or a composition comprising said compound.

An amount effective to inhibit protein kinase is an amount that causes measurable inhibition of the kinase activity when compared to the activity of the enzyme in the absence of an inhibitor. Any method may be used to determine inhibition, such as, for example, the Biological Testing Examples described below.

In certain exemplary embodiments, the inventive compounds may be used as coating for stents. A stent is typically an open tubular structure that has a pattern (or patterns) of apertures extending from the outer surface of the stent to the lumen. It is commonplace to make stents of biocompatible metallic materials, with the patterns cut on the surface with a laser machine. The stent can be electro-polished to minimize surface irregularities since these irregularities can trigger an adverse biological response. However, stents may still stimulate foreign body reactions that result in thrombosis or restenosis. To avoid these complications, a variety of stent coatings and compositions have been proposed in the prior art literature both to reduce the incidence of these complications or other complications and restore tissue function by itself or by delivering therapeutic compound to the lumen. For example, drugs having antiproliferative and anti-inflammatory activities have been evaluated as stent coatings, and have shown promise in preventing retenosis (see, for example, Presbitero P., et al., "Drug eluting stents: do they make the difference?", Minerva Cardioangiol, 2002, 50(5):431-442; Ruygrok P. N. et al., "Rapamycin in cardiovascular medicine", Intern. Med. J., 2003, 33(3):103-109; and Marx S. O., et al., "Bench to bedside: the development of rapamycin and its application to stent restenosis", Circulation, 2001, 104(8): 852-855, each of these references is incorporated herein by reference in its entirety). Accordingly, without wishing to be bound to any particular theory, the inventive compounds having anti-inflammatory and/or antiproliferative effects can be used as stent coatings and/or in stent drug delivery devices, inter alia for the prevention of restenosis or reduction of restenosis rate. A variety of compositions and methods related to stent coating and/or local stent drug delivery for preventing restenosis are known in the art (see, for example, U.S. Pat. Nos. 6,517,889; 6,273,913; 6,258,121; 6,251,136; 6,248,127; 6,231,600; 6,203,551; 6,153,252; 6,071,305; 5,891,507; 5,837,313; and U.S. Patent Publication No. US 2001/0027340; each of which is incorporated herein by reference in its entirety). For example, stents may be coated with polymer-drug conjugates by dipping the stent in polymer-drug solution or spraying the stent with such a solution. In certain embodiments, suitable materials for the implantable device include biocompatible and nontoxic materials, and may be chosen from the metals such as nickel-titanium alloys, steel, or biocompatible polymers, hydrogels, polyurethanes, polyethylenes, ethylenevinyl acetate copolymers, etc. In certain embodiments, the inventive compound is coated onto a stent for insertion into an artery or vein following balloon angioplasty.

The invention may be described, therefore, in certain broad aspects as a method of inhibiting arterial restenosis or arterial occlusion following vascular trauma comprising, administering to a subject in need thereof, a composition comprising an inventive compound conjugated to a suitable polymer or polymeric material. In the practice of the method, the subject may be a coronary bypass, vascular surgery, organ transplant or coronary or any other arterial angioplasty patient, for example, and the composition may be administered directly, intravenously, or even coated on a stent to be implanted at the sight of vascular trauma.

In another aspect, the invention encompasses implants and surgical or medical devices, including stents and grafts, coated with or otherwise constructed to contain and/or release any of the inventive compounds disclosed herein. In certain embodiments, the compounds have anti-inflammatory and/or antiproliferative activities. In certain other embodiments, the compounds inhibit smooth muscle cell proliferation. Representative examples of the inventive implants and surgical or medical devices include cardiovascular devices (e.g., implantable venous catheters, venous ports, tunneled venous catheters, chronic infusion lines or ports, including hepatic artery infusion catheters, pacemaker wires, implantable defibrillators); neurologic/neurosurgical devices (e.g., ventricular peritoneal shunts, ventricular atrial shunts, nerve stimulator devices, dural patches and implants to prevent epidural fibrosis post-laminectomy, devices for continuous subarachnoid infusions); gastrointestinal devices (e.g, chronic indwelling catheters, feeding tubes, portosystemic shunts, shunts for ascites, peritoneal implants for drug delivery, peritoneal dialysis catheters, implantable meshes for hernias, suspensions or solid implants to prevent surgical adhesions, including meshes); genitourinary devices (e.g., uterine implants, including intrauterine devices (IUDs) and devices to prevent endometrial hyperplasia, fallopian tubal implants, including reversible sterilization devices, fallopian tubal stents, artificial sphincters and periurethral implants for incontinence, ureteric stents, chronic indwelling catheters, bladder augmentations, or wraps or splints for vasovasostomy); phthalmologic implants (e.g., multino implants and other implants for neovascular glaucoma, drug eluting contact lenses for pterygiums, splints for failed dacrocystalrhinostomy, drug eluting contact lenses for corneal neovascularity, implants for diabetic retinopathy, drug eluting contact lenses for high risk corneal transplants); otolaryngology devices (e.g., ossicular implants, Eustachian tube splints or stents for glue ear or chronic otitis as an alternative to tranestempanic drains); plastic surgery implants (e.g., prevention of fibrous contracture in response to gel- or saline-containing breast implants in the subpectoral or subglandular approaches or post-mastectomy, or chin implants), and orthopedic implants (e.g., cemented orthopedic prostheses).

Implants and other surgical or medical devices may be coated with (or otherwise adapted to release) compositions of the present invention in a variety of manners, including for example: (a) by directly affixing to the implant or device an inventive compound or composition (e.g., by either spraying the implant or device with a polymer/drug film, or by dipping the implant or device into a polymer/drug solution, or by other covalent or noncovalent means); (b) by coating the implant or device with a substance such as a hydrogel which will in turn absorb the inventive compound or composition; (c) by interweaving inventive compound- or composition-coated thread (or the polymer itself formed into a thread) into the implant or device; (d) by inserting the implant or device into a sleeve or mesh which is comprised of or coated with an inventive compound or composition; (e) constructing the implant or device itself with an inventive compound or composition; or (f) by otherwise adapting the implant or device to release the inventive compound. In certain embodiments, the composition should firmly adhere to the implant or device during storage and at the time of insertion. The inventive compound or composition should also preferably not degrade during storage, prior to insertion, or when warmed to body temperature after insertion inside the body (if this is required). In addition, it should preferably coat the implant or device smoothly and evenly, with a uniform distribution of inventive compound, while not changing the stent contour. Within preferred embodiments of the invention, the inventive implant or device should provide a uniform, predictable, prolonged release of the inventive compound or composition into the tissue surrounding the implant or device once it has been deployed. For vascular stents, in addition to the above properties, the composition should not render the stent thrombogenic (causing blood clots to form), or cause significant turbulence in blood flow (more than the stent itself would be expected to cause if it was uncoated).

In the case of stents, a wide variety of stents may be developed to contain and/or release the inventive compounds or compositions provided herein, including esophageal stents, gastrointestinal stents, vascular stents, biliary stents, colonic stents, pancreatic stents, ureteric and urethral stents, lacrimal stents, Eustachian tube stents, fallopian tube stents and tracheal/bronchial stents (see, for example, U.S. Pat. No. 6,515,016, the entire contents of which are incorporated herein by reference). Stents may be readily obtained from commercial sources, or constructed in accordance with well-known techniques. Representative examples of stents include those described in U.S. Pat. No. 4,768,523, entitled "Hydrogel Adhesive"; U.S. Pat. No. 4,776,337, entitled "Expandable Intraluminal Graft, and Method and Apparatus for Implanting and Expandable Intraluminal Graft"; U.S. Pat. No. 5,041,126 entitled "Endovascular Stent and Delivery System"; U.S. Pat. No. 5,052,998 entitled "Indwelling Stent and Method of Use"; U.S. Pat. No. 5,064,435 entitled "Self-Expanding Prosthesis Having Stable Axial Length"; U.S. Pat. No. 5,089,606, entitled "Water-insoluble Polysaccharide Hydrogel Foam for Medical Applications"; U.S. Pat. No. 5,147,370, entitled "Nitinol Stent for Hollow Body Conduits"; U.S. Pat. No. 5,176,626, entitled "Indwelling Stent"; U.S. Pat. No. 5,213,580, entitled "Biodegradable Polymeric Endoluminal Sealing Process"; and U.S. Pat. No. 5,328,471, entitled "Method and Apparatus for Treatment of Focal Disease in Hollow Tubular Organs and Other Tissue Lumens."

As discussed above, the stent coated with (or otherwise adapted to release) compositions of the present invention may be used to eliminate a vascular obstruction and prevent restenosis or reduce the rate of restenosis. Within other aspects of the present invention, stents coated with (or otherwise adapted to release) compositions of the present invention are provided for expanding the lumen of a body passageway. Specifically, a stent having a generally tubular structure, and a surface coated with (or otherwise adapted to release) an inventive compound or composition may be inserted into the passageway, such that the passageway is expanded. In certain embodiments, the stent coated with (or otherwise adapted to release) compositions of the present invention may be used to eliminate a biliary, gastrointestinal, esophageal, tracheali-bronchial, urethral or vascular obstruction.

In another aspect of the invention, the radicicol analogues described herein are used as diagnostic agents for kinase-mediated disorders. The inventive compounds have a high affinity for kinases and may be used to detect and/or diagnose disorders associated with over expression of kinases. For example, cell cycle regulatory proteins are overexpressed in many proliferative disorders and the compounds of the invention may be used to detect and diagnose these disorders. In one embodiment, the inventive radicicol A compounds of the invention may be used with in vitro methods as diagnostic agents for kinase-mediated disorders. In another embodiment, the radicicol A analogues of the invention may be conjugated to clinically used diagnostic compounds. In one embodiment, the radicicol A analogues may be conjugated to MRI contrast agents or other clinically used diagnostic agents to provide a diagnostic tool for disorders related to over expression of kinases, such as cancer.

Pharmaceutical Compositions

Mammals, and specifically humans, suffering from a respiratory disorder can be treated by the inhalation, systemic, oral, topical, or transdermal administration of a composition comprising an effective amount of the compounds described herein or a pharmaceutically acceptable salt, ester or prodrug thereof, optionally in a pharmaceutically acceptable carrier or diluent.

The compounds or compositions are typically administered by oral or inhalation administration. Alternatively, compounds can be administered subcutaneously, intravenously, intraperitoneally, intramuscularly, parenterally, orally, submucosally, by inhalation, transdermally via a slow release patch, or topically, in an effective dosage range to treat the target condition.

An effective dose can be readily determined by the use of conventional techniques and by observing results obtained under analogous circumstances. In determining the effective dose, a number of factors are considered including, but not limited to: the species of patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication.

In a separate embodiment, the compounds of the invention are in the form of an inhaled dosage. In this embodiment, the compounds may be in the form of an aerosol suspension, a dry powder or liquid particle form. The compounds may be prepared for delivery as a nasal spray or in an inhaler, such as a metered dose inhaler. Pressurized metered-dose inhalers ("MDI") generally deliver aerosolized particles suspended in chlorofluorocarbon propellants such as CFC-11, CFC-12, or the non-chlorofluorocarbons or alternate propellants such as the fluorocarbons, HFC-134A or HFC-227 with or without surfactants and suitable bridging agents. Dry-powder inhalers can also be used, either breath activated or delivered by air or gas pressure such as the dry-powder inhaler disclosed in the Schering Corporation International Patent Application No. PCT/US92/05225, published 7 Jan. 1993 as well as the Turbuhaler™ (available from Astra Pharmaceutical Products, Inc.) or the Rotahaler™ (available from Allen & Hanburys) which may be used to deliver the aerosolized particles as a finely milled powder in large aggregates either alone or in combination with some pharmaceutically acceptable carrier e.g. lactose; and nebulizers.

The compounds of the invention may be also administered in specific, measured amounts in the form of an aqueous suspension by use of a pump spray bottle. The aqueous suspension compositions of the present invention may be prepared by admixing the compounds with water and other pharmaceutically acceptable excipients. The aqueous suspension compositions according to the present invention may contain, inter alia, water, auxiliaries and/or one or more of the excipients, such as: suspending agents, e.g., microcrystalline cellulose, sodium carboxymethylcellulose, hydroxypropyl-methyl cellulose; humectants, e.g. glycerin and propylene glycol; acids, bases or buffer substances for adjusting the pH, e.g., citric acid, sodium citrate, phosphoric acid, sodium phospate as well as mixtures of citrate and phosphate buffers; surfactants, e.g. Polysorbate 80; and antimicrobial preservatives, e.g., benzalkonium chloride, phenylethyl alcohol and potassium sorbate.

Typical systemic dosages for all of the herein described conditions are those ranging from 0.01 mg/kg to 1500 mg/kg of body weight per day as a single daily dose or divided daily doses. Preferred dosages for the described conditions range from 0.5-1500 mg per day. A more particularly preferred dosage for the desired conditions ranges from 5-750 mg per day. Typical dosages can also range from 0.01 to 1500, 0.02 to 1000, 0.2 to 500, 0.02 to 200, 0.05 to 100, 0.05 to 50, 0.075 to 50, 0.1 to 50, 0.5 to 50, 1 to 50, 2 to 50, 5 to 50, 10 to 50, 25 to 50, 25 to 75, 25 to 100, 100 to 150, or 150 or more mg/kg/day, as a single daily dose or divided daily doses. In one embodiment, the compounds are given in doses of between about 1 to about 5, about 5 to about 10, about 10 to about 25 or about 25 to about 50 mg/kg. Typical dosages for topical application are those ranging from 0.001 to 100% by weight of the active compound.

The compounds are conveniently administered in units of any suitable dosage form, including but not limited to one containing from about 7 to 3000 mg, from about 70 to 1400 mg, or from about 25 to 1000 mg of active ingredient per unit dosage form. For example, an oral dosage of from about 50 to 1000 mg is usually convenient, including in one or multiple dosage forms of 50, 100, 200, 250, 300, 400, 500, 600, 700, 800, 900 or 1000 mgs. Lower dosages may be preferable, for example, from about 10-100 or 1-50 mgs. Also contemplated are doses of 0.1-50 mg, 0.1-20 mgs., or 0.1-10 mgs. Furthermore, lower doses may be utilized in the case of administration by a non-oral route, as for example, by injection or inhalation.

The compound is administered for a sufficient time period to alleviate the undesired symptoms and the clinical signs associated with the condition being treated.

The active compound is included in the pharmaceutically acceptable carrier or diluent in an amount sufficient to deliver to a patient a therapeutic amount of compound in vivo in the absence of serious toxic effects. Pharmaceutically acceptable carriers that may be used in these pharmaceutical compositions are generally known in the art. They include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, solvents, salts or electrolytes, such as protamine sulfate, disodium hydrogen phosphate, potassium hydrogen phosphate, sodium chloride, zinc salts, silicates, colloidal silica, magnesium trisilicate, polyvinyl pyrrolidone, cellulose-based substances, polyethylene glycol, sodium carboxymethylcellulose, polyacrylates, waxes, oils, polyethylene-polyoxypropylene-block polymers, polyethylene glycol and wool fat. Pharmaceutically accepted vehicles can contain mixtures of more than one excipient in which the components and the ratios can be selected to optimize desired characteristics of the formulation including but not limited to shelf-life, stability, drug load, site of delivery, dissolution rate, self-emulsification, control of release rate and site of release, and metabolism.

Formulations can be prepared by a variety of techniques known in the art. Examples of formulation techniques can be found in literature publications and in texts such as "Water-insoluble drug formulation", edited by Rong Liu, 2000, Interpharm Press.

If administered intravenously, carriers can be physiological saline, bacteriostatic water, Cremophor EL™ (BASF, Parsippany, N.J.) or phosphate buffered saline (PBS). Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other surface-active emulsifying agents or bioavailability enhancers which are commonly used in the manufacture of pharmaceutically acceptable solid, liquid, or other dosage forms may also be used for the purposes of formulation.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

One mode of administration of the active compound for systemic delivery is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound or its salts can be administered as a component of an elixir, suspension, syrup, wafer, chewing gum or the like. A syrup may contain, in addition to the active compounds, sucrose as a sweetening agent and certain preservatives, dyes and colorings and flavors.

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the compound is then introduced into the container. The container is then swirled by hand to free lipid material from the sides of the container and to disperse lipid aggregates, thereby forming the liposomal suspension.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening agents, emollients, and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene.

Combination Treatment

The compound can also be mixed with other active materials which do not impair the desired action, or with materials that supplement the desired action. The active compounds can be administered in conjunction, i.e. combination or alternation, with other medications used in the treatment of disorders that are mediated by kinases or phosphatases. In one embodiment, the other active agents will have a different mode of action than the compounds of the present invention. In another embodiment, the inventive compound may be administered with another compound approved for the treatment of cancer, preferably a second anti-cancer agent that acts by a distinct mechanism than the compounds of the present invention. For example, the compounds of the invention may be used in combination with other anticancer drugs such as vincristine, cisplatin, ara-C, taxanes, edatrexate, L-buthionine sulfoxide, tiazofurin, gallium nitrate, doxorubicin, etoposide, podophyllotoxins, cyclophosphamide, camptothecins, dolastatin, and auristatin-PE. The compound of the invention may also be used in combination with radiation therapy.

The compounds can be administered in combination or alternation with drugs typically useful for treatment or prevention of asthma, such as certain anti-inflammatory drugs and bronchodilators. Corticosteroids (inhaled and oral), mast cell stabilizers, and the leukotriene modifier drugs are typically a useful anti-inflammatory medication for people suffering from asthma. These drugs reduce swelling and mucus production in the airways. Bronchodilators typically relieve the symptoms of asthma by relaxing the muscle bands that tighten around the airways. This action rapidly opens the airways, letting more air come in and out of the lungs. Bronchodilators also help clear mucus from the lungs.

Typically used compounds include Inhaled corticosteroids, which prevent rather than relieve symptoms. Inhaled corticosteroids include: Advair (a combination medication that includes a corticosteroid (fluticasone) plus a long acting bronchodilator drug (in this case a β-2 adrenergic receptor agonist, salmeterol)), aerobid (flunisolide), azmacort (triamcinolone), flovent (fluticasone), methylprednisolone, prednisone, pulmicort or serevent diskus (salmeterol powder), theophylline, qvar, and xopenex (levalbuterol), Inhaled corticosteroids come in three forms: the metered dose inhaler (MDI), dry powder inhaler (DPI) and nebulizer solutions. Systemic steroids include: methylprednisolone (Medrol, Methylpred, Solu-Medrol), prednisone (Deltasone) and prednisolone (Prelone, Pediapred, Orapred). Mast Cell Stabilizers include Intal and Tilade, which work by preventing the release of irritating and inflammatory substances from mast cells. Leukotriene modifiers include accolate and singular and accolate (zafirlukast), singulair (montelukast) and zyflo (zileuton).

The compounds can be administered in combination with nonsteroidal anti-inflammatories such as ibuprofen, indomethacin, fenoprofen, mefenamic acid, flufenamic acid, and sulindac. The compound can also be administered with corticosteroids. Any of the compounds described herein for combination or alternation therapy can be administered as any prodrug that upon administration to the recipient, is capable of providing directly or indirectly, the parent compound. Nonlimiting examples are the pharmaceutically acceptable salts (alternatively referred to as "physiologically acceptable salts"), and a compound which has been alkylated or acylated at an appropriate position. The modifications can affect the biological activity of the compound, in some cases increasing the activity over the parent compound.

Processes for the Preparation of the Compounds

Modular synthetic processes directed to the synthesis of radicicol A and analogues of radicicol A are provided herein. It is understood that the synthetic processes described herein are exemplary and are not limited to a specific compound or analogue. These processes may be adapted to prepare any of the compounds of the invention by methods known in the art. The syntheses described herein are particularly useful because they are compatible with high throughput synthesis.

The following abbreviations are used herein.
Ac Acetyl (CH3C=O)
All Allyl
9-BBN 9-borabicyclo[3.3.1]nonane
Bn Benzyl
Bz Benzoyl
BuLi n-butyllithium
BuSnH tributyltin hydride
CAN Ceric ammonium nitrate
δ Chemical shift (NMR)
dba Dibenzylideneacetone
DBU 1,8-Diazabicyclo[5.4.0]undec-7-ene
DDQ 2,3-Dichloro-5,6-dicyano-1,4-benzoquinone
DEAD Diethyl azodicarboxylate
DIAD Diisopropyl azodicarboxylate
d.e. Diastereoisomeric excess
DIBAL or Dibal-H Diisobutylaluminum hydride
DMAP 4-Dimethylaminopyridine
DMF Dimethylformamide
DMPI Dess-Martin periodinane
DMSO Dimethylsulfoxide
$EC_{50}$ Plasma concentration required for obtaining 50% of maximum effect in vivo
EDC 1-Ethyl-3-[3-dimethylaminopropyl]carbodiimide hydrochloride
e.e. Enantiomeric excess
EOM Ethoxymethyl ($CH_3CH_2OCH_2$—)

Grubbs' II Grubbs' second generation catalyst: (ruthenium [1,3-bis(2,4,6-trimethylphenyl)-2-imidazolinylidene) dichloro(phenylmethylene) (tricyclohexylphosphane)

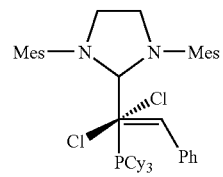

Grubbs' II

HMDS Hexamethyldisilazide
HMPA Hexamethylphosphotictriamide
HPLC High performance chromatography
HRMS High resolution mass spectrometry
IBX 2-Iodoxybenzoic acid
Hunig's Base Diisopropylethylamine
$IC_{50}$ Concentration of a drug that is required for 50% inhibition in vitro
J Coupling constant
L.C. Liquid chromatography
LDA Lithium diisopropylamide
LiAlH Lithium aluminum hydride
LiHMDS Lithium hexamethyldisilazide ($LiN(SiMe_3)_2$)
μM Micromolar concentration ($\mu mol.l^{-1}$)
mCPBA meta-Chloroperoxybenzoic acid
M.S. Mass spectrum
NaHMDS Sodium hexamethyldisilazide
NMR Nuclear magnetic resonance
OEM ethoxymethylene
NOE(SY) Nuclear overhauser effect
PG Protecting Group
PMB para-Methoxybenzyl
PMB-Cl para-Methoxybenzyl chloride
Piv Pivaloyl
PS—Polymer supported
Pyr or Py Pyridine
rac Racemic
RAL Resorcylic acid lactone
RCM Ring-closing metathesis
RedAl Sodium bis(methoxyethoxy) aluminum hydride
$R_f$ Retention factor
RT Room temperature
SAE Sharpless asymmetric epoxidation
SAR Structure-activity relationship
SEM 2-Trimethylsilylethoxymethoxy
TBAF Tetra-n-butylammonium fluoride
TBAI Tetra-n-butylammonium iodide
TBDPS t-Butyldiphenylsilyl
TBHP t-Butylhydroperoxide
TBS t-Butyldimethylsilyl
Tf Triflate ($CF_3SO_3$)
THF Tetrahydrofuran
THP Tetrahydropyran
TLC Thin layer chromatography
Tol toluene
TMS Trimethylsilyl
Ts Tosyl (p-$CH_3C_6H_4SO_2$)
p-TSOH para-Toluenesulfonic acid Synthetic Strategy In another aspect of the invention, processes for the preparation of analogues and derivatives of radicicol A are provided. An important aspect of the processes described herein is that they are amenable to the use of fluorous isolation technology (see D. P. Curran, *Handbook of Fluorous Chemistry* 2004, 101; W. Zhang, D. P. Curran, *Tetrahedron* 2006, 62, 11837) until isolation of the penultimate cyclization to the macrocycles. It is known in the art that multiple synthetic components conjugated to fluorinated moieties of different chain length can be carried though multistep syntheses as a mixture and ultimately resolved using fluorous chromatography (S. Dandapani, M. Jeske, D. P. Curran, *Proceedings of the National Academy of Sciences of the United States of America* 2004, 101, 12008; Z. Luo, Q. Zhang, Y. Oderaotoshi, D. P. Curran, *Science (Washington, D.C., United States)* 2001, 291, 1766). This technology has been automated and can be adapted for high throughput synthesis (W. Zhang, Y. Lu, *Journal of Combinatorial Chemistry* 2006, 8, 890).

In one embodiment, a synthetic strategy for the synthesis of the radicicol A analogues of the invention shown in the figure below is provided. A significant challenge is to control the cis-geometry of the enone as it can isomerizes to the thermodynamically more favorable trans-isomer as in compound 4, which is known to be significantly less active. In this embodiment, the enone functionality is revealed only at a late stage of the synthesis by using a selective allylic oxidation and that the cis-alkene would originate from a vinyl anion equivalent addition onto an aldehyde. As shown below, the molecule could thus be disconnected into three fragments of even complexity: intermediates 7, 8 and 9 where the aldehyde or leaving group of fragment 8 may be masked depending on the order of assembly. Fragment 8 may vary in chain length to prepare compounds with 13, 14 or 15-membered macrocyclic rings. While the order of coupling of these three fragments is possible in all permutations, the sequence with the coupling of compounds 8+9 allow the use of a fluorinated protecting group (PG) for the alcohol 9, allowing for the use of fluorous isolation technology as described above. The synthetic strategy outlined below allows for multiple components tagged with different length of fluorinated tags, which allow intermediates to be carried through the synthesis as a mixture until they are purified using fluorous technology at an appropriate stage.

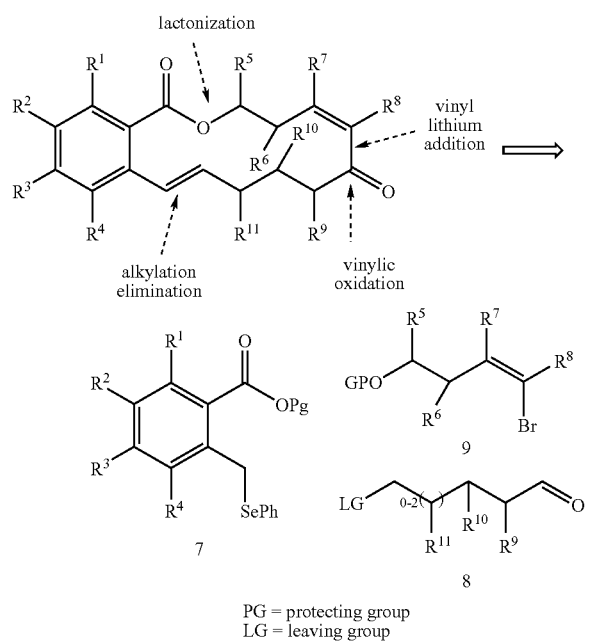

Retrosynthetic Disconnection of Radicicol A Analogues.

As the dotted lines at the benzylic position of the macrocycle and the aromatic intermediate 7 indicate, preparation of an analogue with a carbon-carbon double bond may be achieved by introduction of a benzylic selenide which is eliminated under oxidative conditions to provide the double bond.

It will be appreciated that alternate reagents known in the art may be used to accomplish the transformations described in the synthesis of the inventive compounds. For example the use of the protecting groups described in the various schemes is not limited to the specific reagents or protecting groups. Many suitable protecting groups suitable for various functional groups are known and described in the literature, for example as taught in Greene, et al., *Protective Groups in Organic Synthesis*, John Wiley and Sons, Third Edition, 1999. In addition, alternate reagents known in the art to carry out the transformations described herein may be used. For example although oxalyl chloride is used to prepare the acid chloride of benzylic acids 10, 11 and 12 in scheme 1 below, alternate reagents such as thionyl chloride and the like which are known to transform carboxylic acids to the corresponding acid halides may be used.

In one embodiment, the macrocyclization is accomplished by forming the cyclic ester bond between the benzylic acid component and the alcohol. Various methods of forming a cyclic ester may be used. For example, in one embodiment a Mitsunobu macrocyclization may be used to form the cyclic ester. Alternate methods to form the cyclic ester are also provided, as described in more detail below. In other embodiments, other methods of forming the macrocycle known in the art may be used.

As a non-limiting example of the synthetic strategy described above, the synthesis of radicicol A and radicicol A analogues 3 and 31 is described in schemes 1-3 below. As discussed above, it is understood that the synthetic sequence is not limited by the specific reagents and conditions and alternate reagents and protecting groups known in the art to carry out the transformations shown in the schemes. Synthesis of Aromatic Intermediate Using the synthetic methodology described above, radicicol A and the two analogues, compounds 3 and 31 were prepared. Scheme 1 depicts the synthesis of aromatic intermediate 13, 14 and 15, corresponding to aromatic compound 7 above. In this example, the aromatic fragment was prepared with a silyl based protecting group (TMSE) for the carboxylic acid. As shown in scheme 1, synthesis of compounds 13, 14 and 15 was achieved in two steps from the differently substituted acids 10-12 by esterification with 2(trimethylsilyl)ethanol followed by formation of the selenide via deprotonation of the benzylic position with a bulky base, such as LDA and reaction with diphenydiselenide. The procedure was found to be effective for the trimethoxysubstituted aryl ring corresponding to radicicol A (10) as well as for the dimethoxy aryl ring (11) and the chloro-dimethoxy substitution present in radicicol (12). This methodology may be used for aromatic intermediates with varying substitution about the aromatic ring.

Scheme 1. Synthesis of aromatic moieties 13-15.

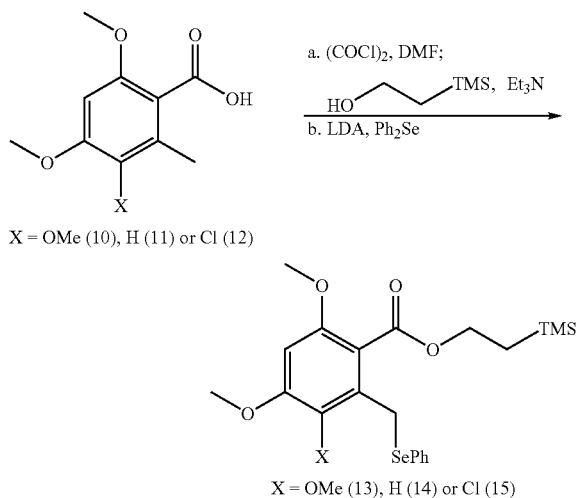

X = OMe (10), H (11) or Cl (12)

X = OMe (13), H (14) or Cl (15)

a) (COCl)$_2$, (1.0 equiv), DMF (cat), CH$_2$Cl$_2$, 0° C., 1 h,; then 2(trimethylsilyl)ethanol (1.0 equiv), Et$_3$N (2.6 equiv), 4-DMAP (cat), 23° C., 1 h, 96-98%; b) LDA (2.0 equiv), (PhSe)$_2$ (1.0 equiv), THF, -78° C., 1 h, 89-91%, 4-DMAP = 4-dimehtylamino pyridine, DMF = dimethylformamide, LDA = lithium diisopropylamide, THF = tetrahydrofuran.

Preparation of Macrocycle

Schemes 2 and 3 below describe the preparation of a key aldehyde intermediate 17 and the synthesis of radicicol A (1) and radicicol A analogues 3 and 31. Aldehyde 17, which corresponds to one embodiment of fragment 8 shown above, is used to prepare an aldehyde intermediate containing a leaving group, such as the alkyl iodide 24 shown in scheme 3. As scheme 2 shows, hemiacetal 17 is reduced with lithium aluminum hydride to the diol intermediate and the more accessible alcohol is selectively protected as the tert-butyldiphenylsilyl ether (TBDPS). Oxidation of the remaining hydroxy group to the aldehyde is achieved with the polymer bound IBX reagent.

Scheme 2. Synthesis of intermediate 17.

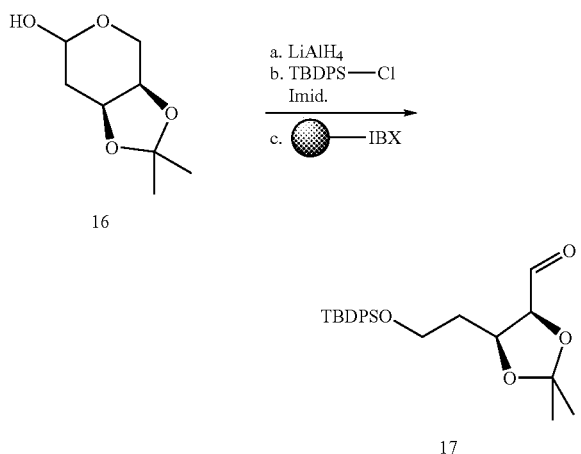

a) LiAlH$_4$ (1.4 equiv), THF, from 0° C. to 23° C., 2 h, 95%; b) TBDPS—Cl (1.0 equiv), Imid. (1.5 equiv), DMF, 23° C., 2 h, 66%; c) PS—IBX (3.0 equiv), CH$_2$Cl$_2$, 23° C., 2 h, 100%, DMF = dimethylformamide, Imid = imidazole, LiAlH$_4$ = Lithium aluminum hydride, PS—IBX = IBX-polystyrene, TBDPS = t-butyldiphenylsilyl, THF = tetrahydrofuran.

Scheme 3 below shows the preparation of radicicol A (1) and analogues 3 and 31. Compound 9 is derived from (R)-2-hydroxybutene, compound 18. In the example illustrated in scheme 3, compound 18 is protected with a fluorous version of paramethoxy benzyl (PMB) trichloroactimidate 19 (see S. Dandapani, M. Jeske, D. P. Curran, *Proceedings of the National Academy of Sciences of the United States of America* 2004, 101, 12008 and Q. Zhang, H. Lu, C. Richard, D. P. Curran, *Journal of the American Chemical Society* 2004, 126, 36). Cross metathesis with the vinyl boronate 20 afforded the trans-vinyl boronate (C. Morrill, R. H. Grubbs, *Journal of Organic Chemistry* 2003, 68, 6031) 21 in excellent yield and stereoselectivity (>20:1 E:Z) using the second generation Grubbs' catalyst or even faster and with equally good stereoselectivity using the Grela modified catalyst (see A. Michrowska, R. Bujok, S. Harutyunyan, V. Sashuk, G. Dolgonos, K. Grela, *Journal of the American Chemical Society* 2004, 126, 9318). The trans-vinylboronate 21 was stereospecifically converted to the cis-vinyl bromide 22 in excellent yield using Brown's protocol (H. C. Brown, C. Subrahmanyam, T. Hamaoka, N. Ravindran, D. H. Bowman, S. Misumi, M. K. Unni, V. Somayaji, N. G. Bhat, *Journal of Organic Chemistry* 1989, 54, 606).

Transmetalation of 22 with tBuLi and addition onto the crude aldehyde 17 afforded, after EOM protection, product 23 as a mixture of diastereoisomers (3:1). The lack of selectivity in this later reaction is inconsequential as this center will ultimately be oxidized to the ketone. Conversion of silyl protected hydroxyl group to the iodide (TBAF; Ph$_3$P, I$_2$) afforded compound 21 which was alkylated in excellent yield with the three different aromatic fragments 13-15 previously deprototonated by LDA. The selenide was then oxidized and eliminated affording and compounds 25-27. It is noteworthy that this reaction sequence did not require a single traditional work up. The crude reaction mixtures were simply loaded on fluorous-silica columns and first eluted with 75% MeOH in water to remove all non-fluorous tagged components and then washed with MeOH to recover the desired compounds. All the compounds (21-27) came at the solvent front with the MeOH wash and could be recovered in excellent yields. Reactions that were performed under basic conditions (22 to 23 and alkylation of 24) were quenched with benzoic acid resin prior to loading on the column.

The PMB group was removed by treating the compounds with DDQ. The byproducts of these reactions were easily sequestered using fluorous solid phase extraction while the 2-(trimethylsily)ethyl ester was remove with TBAF. The hydroxyacids thus obtained were engaged in Mitsunobu macrocyclizations using fluorous-tagged triphenyl phosphine and diazo dicarboxylate yielding the macrocyles 28-30 after a fluorous solid phase extraction. The EOM and acetonide groups were quantitatively deprotected using sulfonic acid resin in MeOH while the ortho phenol could be selectively cleaved in the presence of the other methyl ethers using BCl$_3$ or more conveniently, all operations could be achieved in one step with BCl$_3$. The allylic alcohols were then selectively oxidized with the polymer-bound version of IBX affording radicicol A ((1), 5-Z-7-oxozeaenol (3), and radicicol analogue 31 in nearly quantitative yield following a simple filtration.

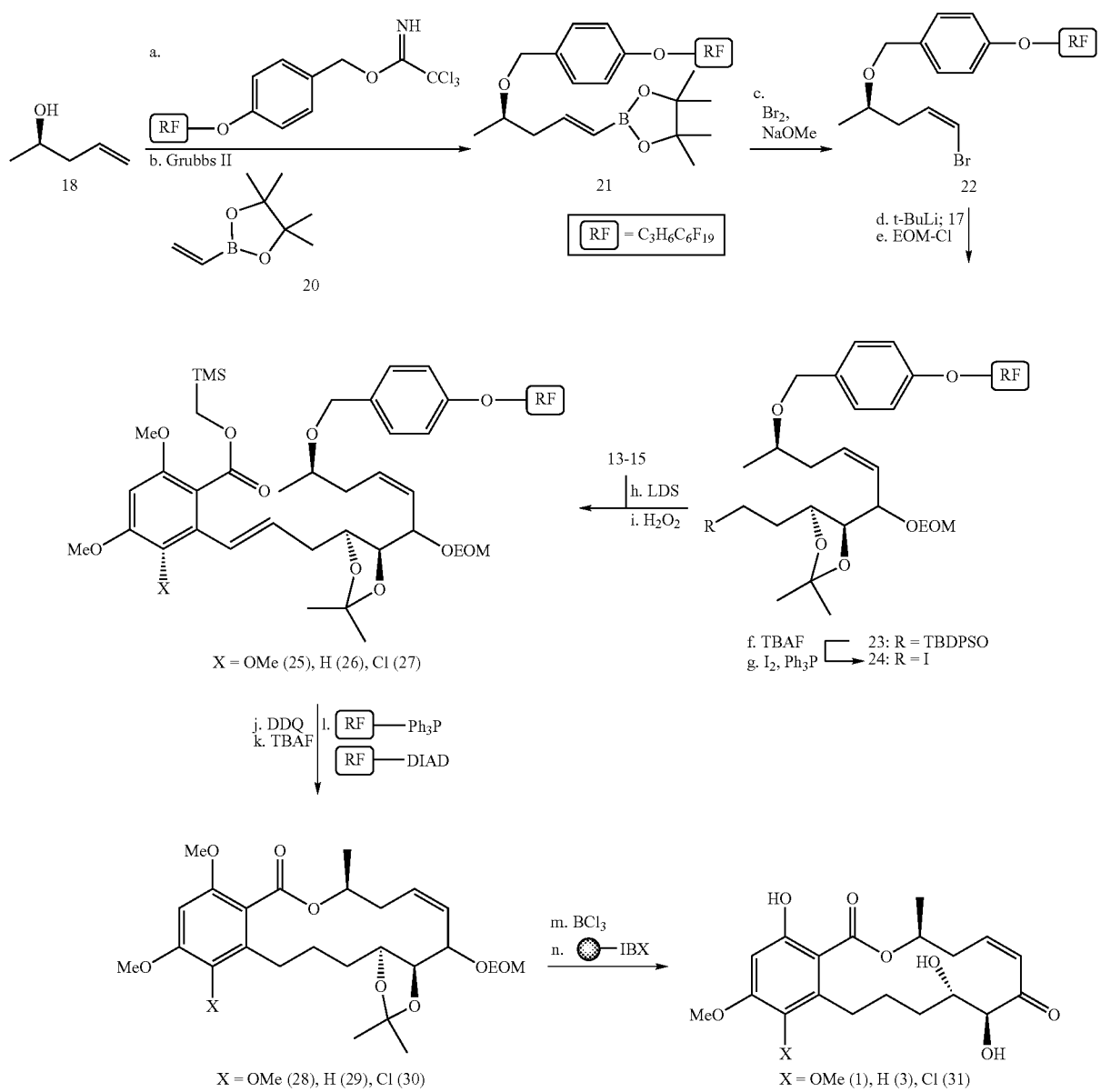

Synthesis of radicicol A (1), 5-z-7-oxozeaenol (3) and radicicol A analogue 31 a) 19 (1.0 equiv), CSA (cat), CH$_2$Cl$_2$, 23° C., 12 h, 92%; b) 20 (2.0 equiv), Grubbs' II (2.5 mol%); toluene, 80° C., 12 h, 92%; c) Br$_2$ (1.0 equiv, 1M in CH$_2$Cl$_2$), Et$_2$O, -20° C., 10 min; and then NaOME (2.2 equiv, 1M in CH$_2$Cl$_2$), Et$_2$O, -20° C., 10 min; and then NaOMe (2.2 equiv, 1M in MeOH), -20° C., 30 min, 89%; d) tBuLi (2.0 equiv), THF/Et$_2$o, -100° C., 15 min; and then 17 (1.0 equiv) -100°C., 15 min, 88%; e) EOM-Cl (8.0 equiv), iPr$_2$EtN (8.0 equiv), TBAI (cat), DMF, 23° C., 12 h, 96%; f) TBAF (2.5 equiv), THF, 23° C., 12 h, 92%; g) PPh$_3$ (1.5 equiv), I$_2$ (1.5 equiv), Imid (2.5 equiv), THF, 0° C., 1 h, 91%; h) 13-15 (1.0 equiv), LDA (2.0 equiv), THF/HMPA 10/1, -78° C., 20 min, 88-91%, i) H$_2$O$_2$ (2.0 equiv), THF, 23 °C., 2 h, 79-82%, j) DDQ (1.2 equiv), CH$_2$Cl$_2$/H$_2$O 2/1, 23° C., 2 h, 70-80%; k) TBAF (3.0 equiv), THF, 23 °C., 2 h, 87%; l) RF-Ph$_3$P (2.0 equiv), RF-DEAD (2.0 equiv), toluene (10 mM), 23° C., 2 h, 81%; m) BCl$_3$ (3.0 equiv), CH$_2$Cl$_2$, 0° C., 15 min, 86%; PS-IBX (3.0 equiv), CH$_2$Cl$_2$, 23° C., 1 h, >90%. CSA = camphor-10-sulfonic acid, DEAD = ethoxycarbonylazocarboxymethyl, DDQ = dichlorodicyanoquinone, EOM = ethoxymethylene, Grubbs'II = ruthenium[1,3-bis{2,4,6-trimethylphenyl}-2-imidazolidinylidene]dichlroro (phenylmethylene)(trcyclohexyphosphine), TBAF = tetrabutylammonium fluoride, TBAI = tetrabutylammonium iodide, TBDPS = t-butyldiphenylsilane, RF = C$_3$H$_6$C$_6$F$_{19}$.

Scheme 4 below illustrates the preparation of radicicol analogues containing a 13, 14 or 15-membered lactone ring that do not contain a double bond at the benzylic position. In this embodiment, the protected aromatic component 50 is treated with a bulky base, such as LDA, and the resulting lithiated benzylic position is alkylated with a protected alcohol component bearing a leaving group, such as alkyl iodide 51. It will be apparent that alternate leaving groups such as alkyl bromides, tosylates, triflates, etc. may be used for this transformation. Following the alkylation of the benzylic position, the protecting groups on the alcohol and carboxylic acid are removed and the macrocycle is formed using a Mitsunobu cyclization reaction. Removal of the EOM alcohol protecting groups followed by oxidation of the allylic alcohol as described above produces the desired 13-15 membered ring macrocycles.

scheme 4. Preparation of 13-15-membered macrocycle bearing a saturated benzylic position.

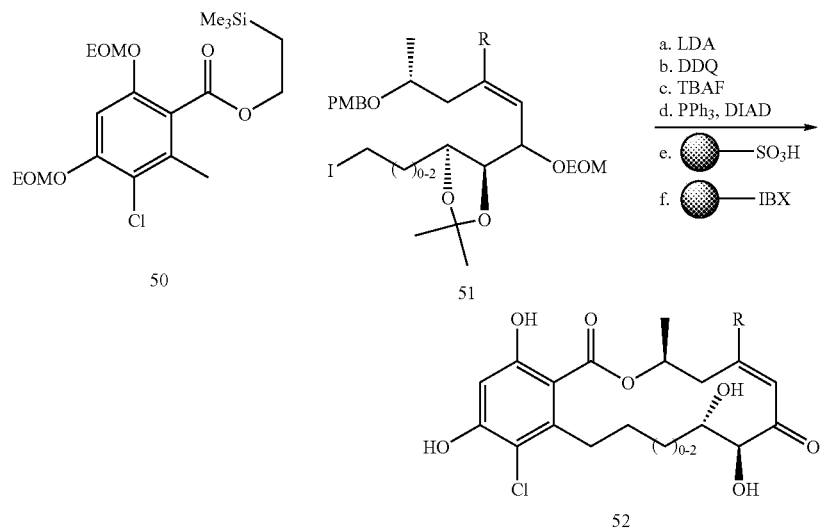

Scheme 5 below illustrates another embodiment of the invention for the preparation of radicicol A analogues. In this non-limiting example, the macrocyclic ring system is formed by alkylation of a benzylic sulfoxide followed by elimination of the sulfoxide to produce the benzylic double bond.

Scheme 5. Alternate synthesis of macrocycles.

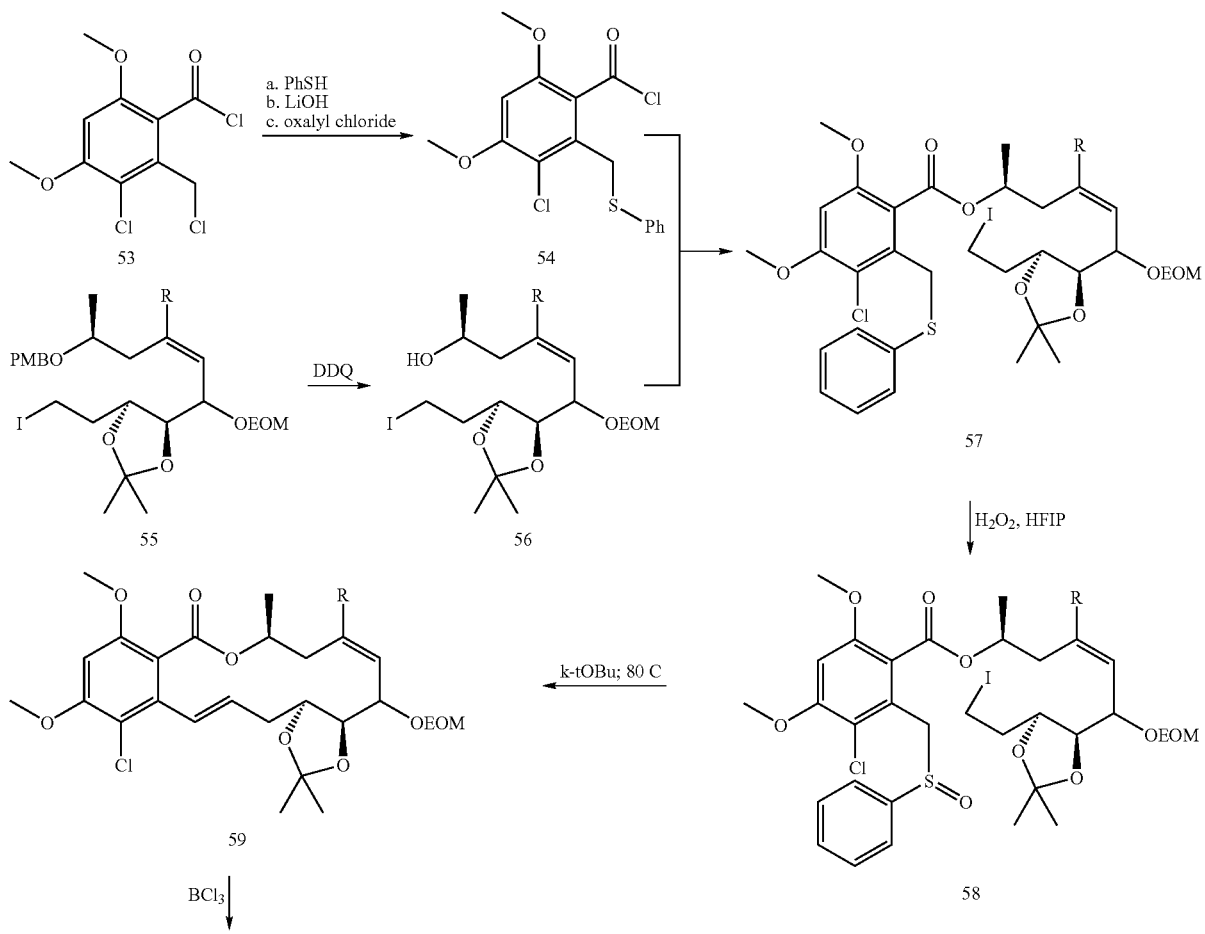

69

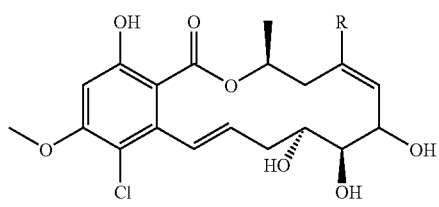

60

R = for example, H, alkyl or halogen

70

-continued

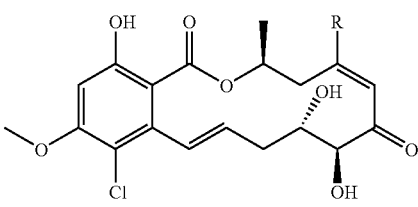   IBX

61

Starting from benzyl chloride 53, treatment with thiophenol followed by hydrolysis of the resulting thio ester provides the thiophenyl-substituted benzylic acid. Treatment with a suitable chlorination reagent, such as oxalyl chloride, forms the desired acid chloride 54, which is then reacted with the alcohol component 56, bearing the protected benzylic alcohol, to produce masked enone intermediate 57. Oxidation of the sulfide to the sulfoxide provides the cyclization precursor 58. This intermediate is treated with a bulky base, such as potassium t-butoxide to produce the macrocycles bearing a benzylic double bond via displacement of the alkyl iodide leaving group by the α-sulfoxide stabilized benzylic anion. It will be apparent to persons skilled in the art that macrocycles without the benzylic double bond may be prepared by intramolecular alkylation of a benzylic anion not bearing a sulfoxide. In addition, the synthetic sequence may prepare compounds with varying substitution patterns based on the substitution of components 7, 8 and 9 shown above.

Schemes 6-11 below outline the preparation of intermediates corresponding to the enone-containing intermediate 24 shown in scheme 3 above with varying substitution patterns used for the synthesis of other radicicol A analogues. Scheme 6 below shows the synthesis of a masked enone-containing intermediate 64 with a methyl group on the enone double bond.

Scheme 6. Preparation of methyl-substituted enone fragment

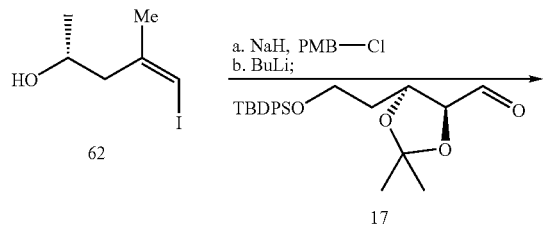

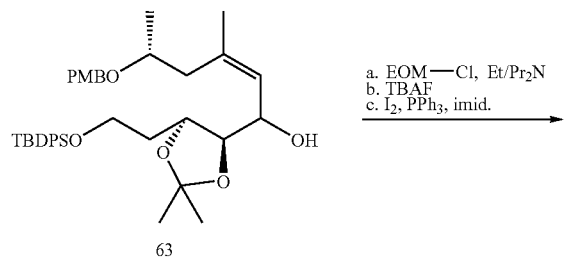

-continued

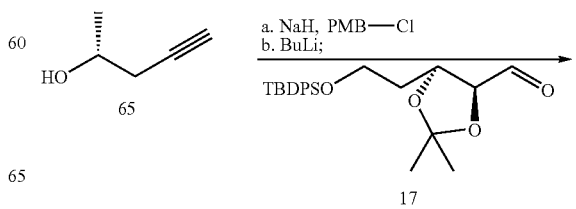

64

Vinyl iodide intermediate 62 shown in Scheme 6 is described by Negishi and co-workers in the *Journal of Organic Chemistry*, 1997, 62(4), 784-785. This intermediate is protected as the PMB ether and then treated with n-butyllithium to form the corresponding vinyl lithium species, which is reacted with aldehyde 17 to form the masked enone-containing intermediate 64. This intermediate is reacted with an appropriate aromatic intermediate 7 having a desired substitution pattern to produce the macrocycle ring precursor. Macrocyclization followed by oxidation to the enone stage and final deprotection, as described above in scheme 3, provides the desired radicicol A analogues substituted with a methyl group at the enone double bond.

Scheme 7 illustrates the synthesis of a masked enone-containing intermediate substituted with a halogen atom at the enone double bond. Butynol 65 is suitably protected as the PMB ether followed by treatment with n-butyllithium to produce the alkynyl lithium intermediate. Reaction of this intermediate with aldehyde 17 provides intermediate 66, which contains the masked enone. Treatment with tributyltin hydride in the presence of the palladium catalyst followed by addition of a diatomic halide, such as iodine, bromine or chlorine, results in formation of vinyl halide 67. In the case of the fluorine substituted compound, the vinyl tin intermediate is treated with the fluorinating agent xenon difluoride in the presence of silver triflate.

Scheme 7. Preparation of halogen-substituted enone intermediate

Scheme 8. Preparation of masked enone-containing intermediate for 15-membered ring analogues

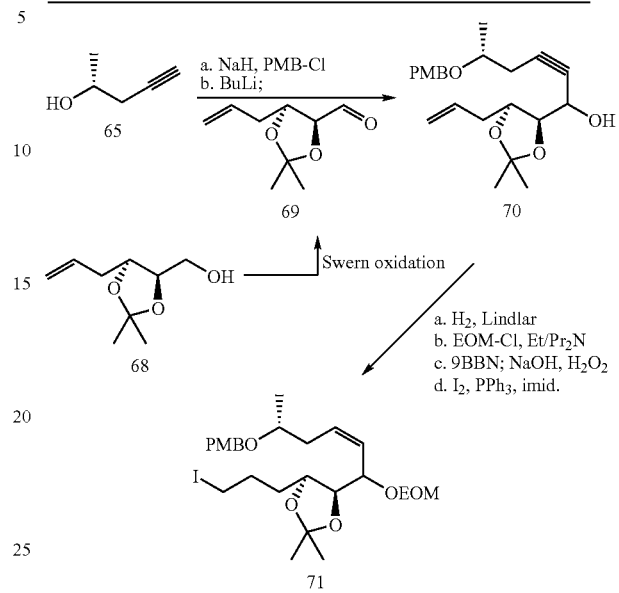

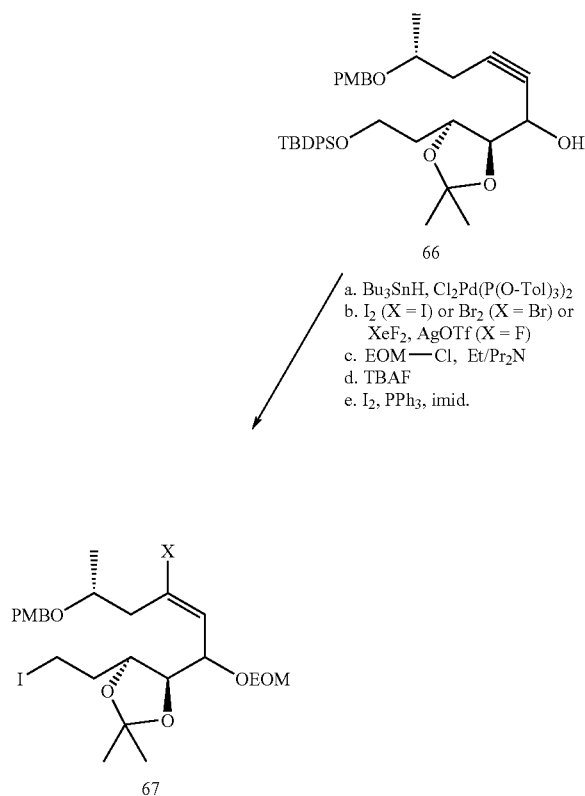

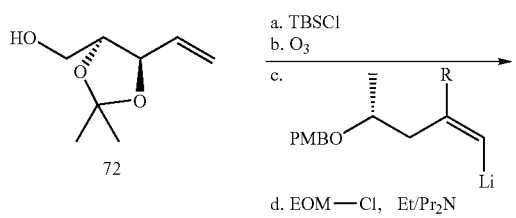

Scheme 8 below shows the synthesis of a masked enone-containing intermediate which may be used for preparing radicicol A analogues containing a 15-membered ring lactone ring. Alcohol 68, which is used to prepare the corresponding aldehyde is described by Danishefsky and co-workers in the *Journal of the American Chemical Society*, 2004, 126, 7881-7889. Homopropargyl alcohols 65 are known (see for example, J. Org. Chem., 1997, 62, 784-785) and can be easily prepared by known methods.

Alcohol 68 is oxidized to aldehyde 69 using, for example, a Swern oxidation or similarly mild oxidation protocols. The homopropargyl alcohol 65 is suitably protected as the PMB ether, treated with n-butyllithium and the resulting alkynyl-lithium intermediate is reacted with aldehyde 69 to produce alcohol 70. Reduction of the triple bond to the corresponding alkene is followed by protection of the allylic alcohol. The leaving group is introduced by preparing the alcohol using a hydroboration reaction and converting resulting the alcohol to the iodide leaving group using triphenylphosphine and iodine, as described for the corresponding intermediate in scheme 3 above.

Scheme 9 describes the preparation of an enone-containing intermediates 74 and 75. Intermediate 74 may be used to prepare radicicol A analogues containing a 13-membered ring lactone and intermediate 75 used to prepare an analogue with a thioether in the macrocycle.

Scheme 9.
Preparation of enone-containing intermediates for 13-membered lactone ring and thioether containing macrocycle

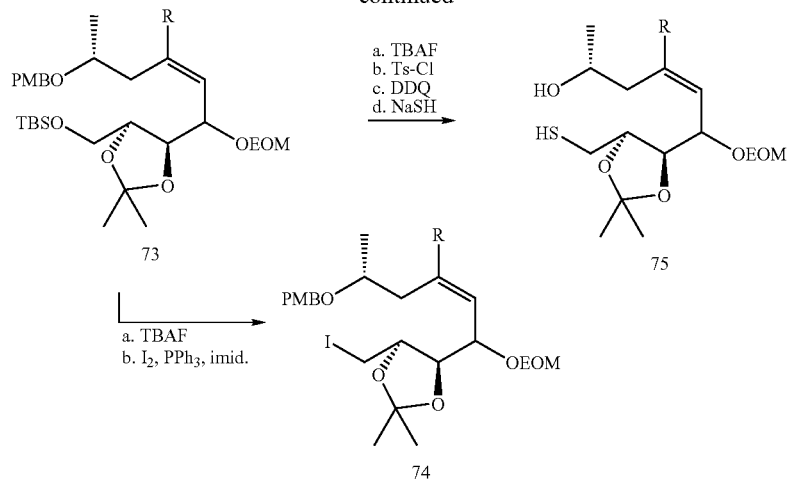

R = H, alkyl or halogen

Alcohol 72 is described by Proteau and co-workers in *Bioorganic & Medicinal Chemistry Letters* 14 (2004), 5309-5312. The alcohol is first protected as the silyl ether and the resulting olefin is subjected to ozonolysis to produce the corresponding aldehyde. The aldehyde is reacted with the vinyl lithium reagent described previously and the resulting alcohol is protected as the EOM ether. For preparation of intermediate 74, the silyl protecting group is removed and the alcohol is converted to the alkyl iodide as described previously. For preparation of intermediate 75, the silyl protecting group is removed and the alcohol is converted to a good leaving group, such as a tosylate, and displaced with NaSH to produce the thiol-substituted intermediate 75.

Scheme 10 below describes the preparation of a masked-enone intermediate with a 3-methyl-2-fluoro enone double moiety. Starting from 2-fluoro-3-methyl lactone 76, reduction of the lactone with diisobutyl aluminum hydride opens the lactone ring to produce the aldehyde. Treatment of the aldehyde with sodium hydride and the vinyllithium reagent produces the allylic alcohol, which is protected as the PMB ether 77. Sharpless asymmetric dihydroxylation (Jacobsen et al., *J. Am. Chem. Soc.*, 1988, 110, 1968), which is selective for the disubstituted olefin, produces the desired diol. Protection of the two hydroxy groups as EOM ethers is followed by deprotection of the silyl ether and conversion of the alcohol to alkyl iodide 78, as described above. Preparation of the corresponding intermediate without the 3-methyl substituent may be realized starting from a suitable fluoro lactone not containing the 3-methyl group or with a different substituent. It will be apparent to skilled persons that the double bond may be functionalized in a different manner by other suitable protocols. For example, using the Sharpless aminohydroxylation protocol (Sharpless et al., *J. Am. Chem. Soc.*, 1975, 97, 2305) rather than the dihydroxylation reaction will provide an intermediate with a 1,2-amino alcohol substitution pattern.

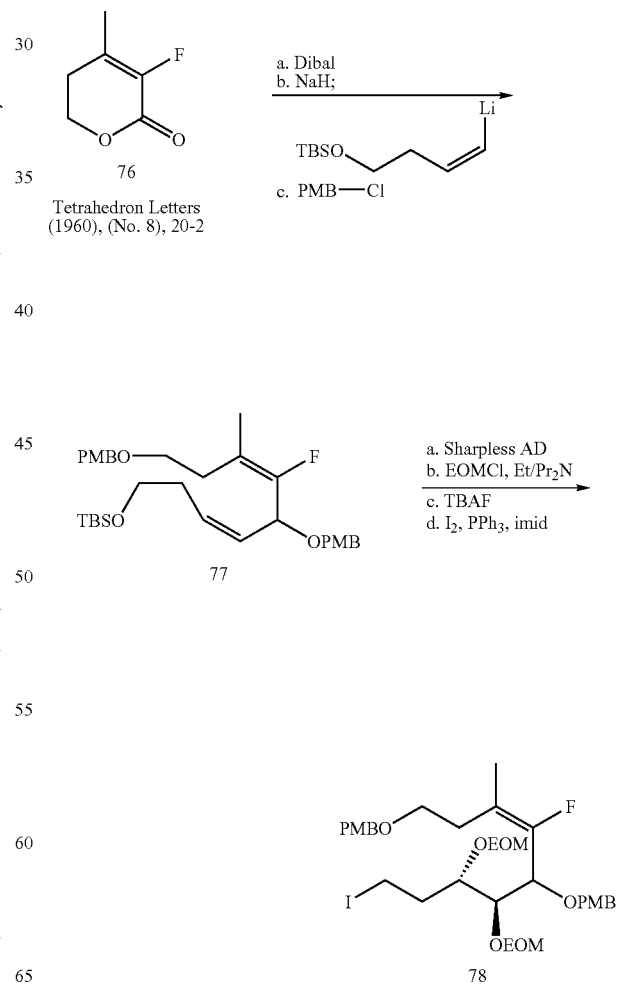

Scheme 11 describes the synthesis of intermediate with a azide substituent, which may be utilized to prepare macrocycles with an azide or amino substituent. Starting from the known epoxide 79, treatment with trimethylsilyl azide under acidic conditions results in ring-opening to form the amino alcohol. Protection of the alcohol as the EOM ether is followed by removal of the TBS protecting group and oxidation to produce the aldehyde 80. The aldehyde is reacted with the vinyllithium reagent described earlier to form the protected allylic alcohol, which is protected as the EOM ether. The terminal olefin is converted to the alcohol and then to the alkyl iodide, as described above for similar intermediates. The azide substituted intermediate may be used to prepare macrocycles with an azide group which may be reduced to the corresponding amino group. Additionally, the amino group may be further functionalized by known methods to prepare derivatives with N-alkyl, N-acyl, N-sulfonyl groups, and the like.

Scheme 11.
Preparation of enone intermediate with amino substituent

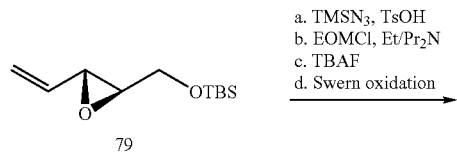

a. TMSN$_3$, TsOH
b. EOMCl, Et/Pr$_2$N
c. TBAF
d. Swern oxidation

79

Organic Letters (2003), 5(15), 2751-2754.

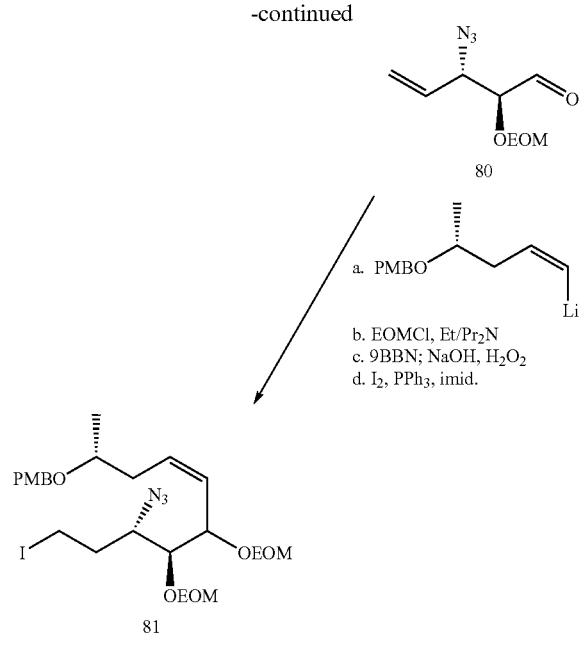

a. PMBO
b. EOMCl, Et/Pr$_2$N
c. 9BBN; NaOH, H$_2$O$_2$
d. I$_2$, PPh$_3$, imid.

Any of the schemes shown above for the construction of the macrocycle may be modified to use different orthogonal protecting groups. For example, in one embodiment, the allylic alcohol may be orthogonally protected and deprotected and oxidized prior to globally deprotecting the other functional groups of the product. Alternatively, the macrocycle may be formed without protecting certain functional groups. For example, it has been found that the macrocyclization reaction may be conducted with an unprotected allylic alcohol 82 as shown in scheme 12 below. The allylic alcohol may then be oxidized to the enone 61 by a suitable oxidation protocol such as the Dess-Martin oxidation (Dess, D. B.; Martin J. C., *J. Org. Chem.*, 1983, 48, 4155)

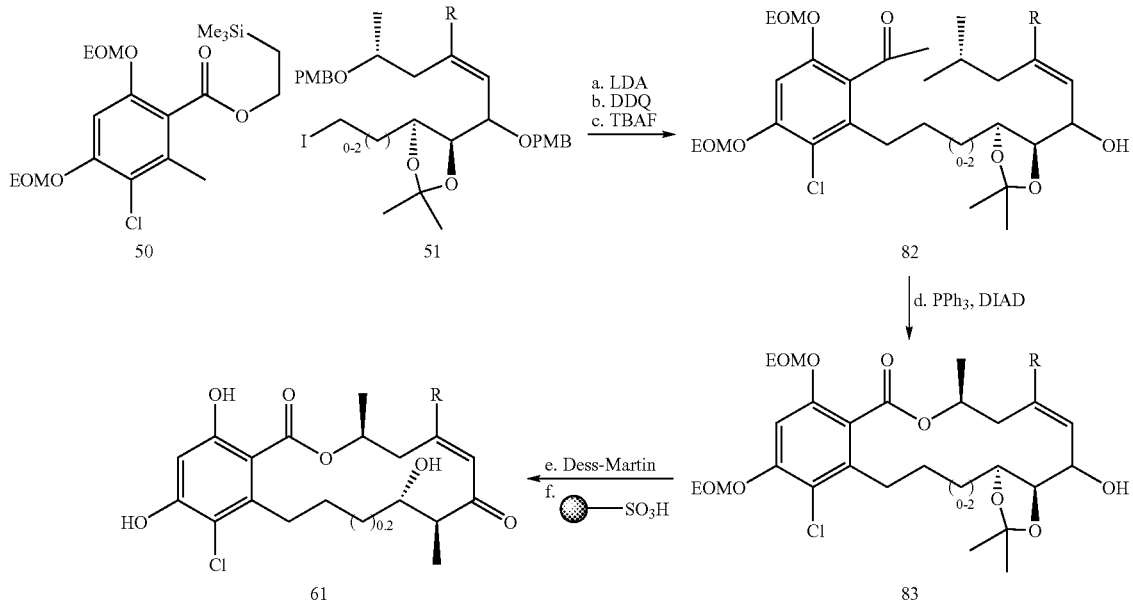

Scheme 13 describes the synthesis of a radicicol A analogue that contains a thioether in the macrocycle. Starting from the benzylchloride 84, which is described in the literature, oxidation to the benzoic acid followed by protection of the resulting acid as the acetonide together with the ortho hydroxy group and subsequent protection of the remaining hydroxy group as the TBS ether provides intermediate 85. Intermediate 85 is reacted with thiol intermediate 86 described earlier to produce the cyclization precursor 87. Treatment of 87 with a bulky base, such as lithium hexamethydisilazane, induces cyclization to the macrocycle with concomitant deprotection of the ortho hydroxy group. Deprotection and oxidation of the allylic alcohol provides the desired radicicol A analogue.

Scheme 14, shown below shows the preparation of a radicicol A analogue containing an ether bond in the macrocycle. The para hydroxy group of known acetonide 89 is selectively protected as the EOM ether and the protected intermediate is reacted with alkyl iodide 56 in the presence of a base, such as potassium carbonate to form the cyclization precursor 90. Treatment of intermediate 90 with a bulky base induces ring closure to the lactone 91 with simultaneous deprotection of the ortho hydroxy group. Deprotection of the EOM protected hydroxy groups and allylic oxidation to the enone provides the desired radicicol A analogue.

Scheme 13. Synthesis of macrocycle with thioether group

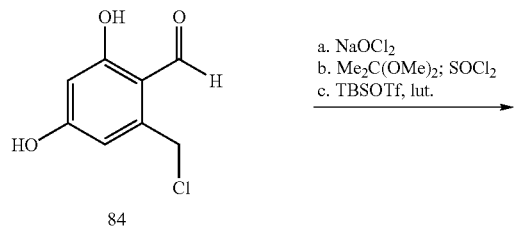

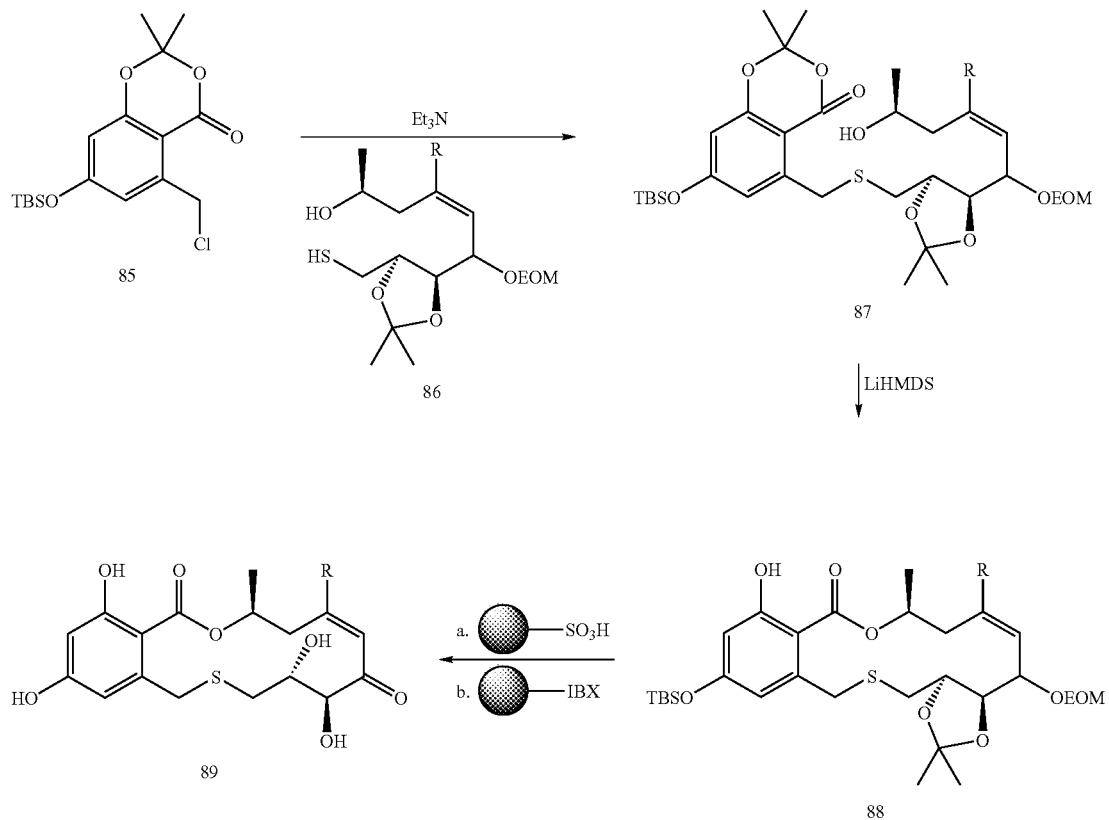

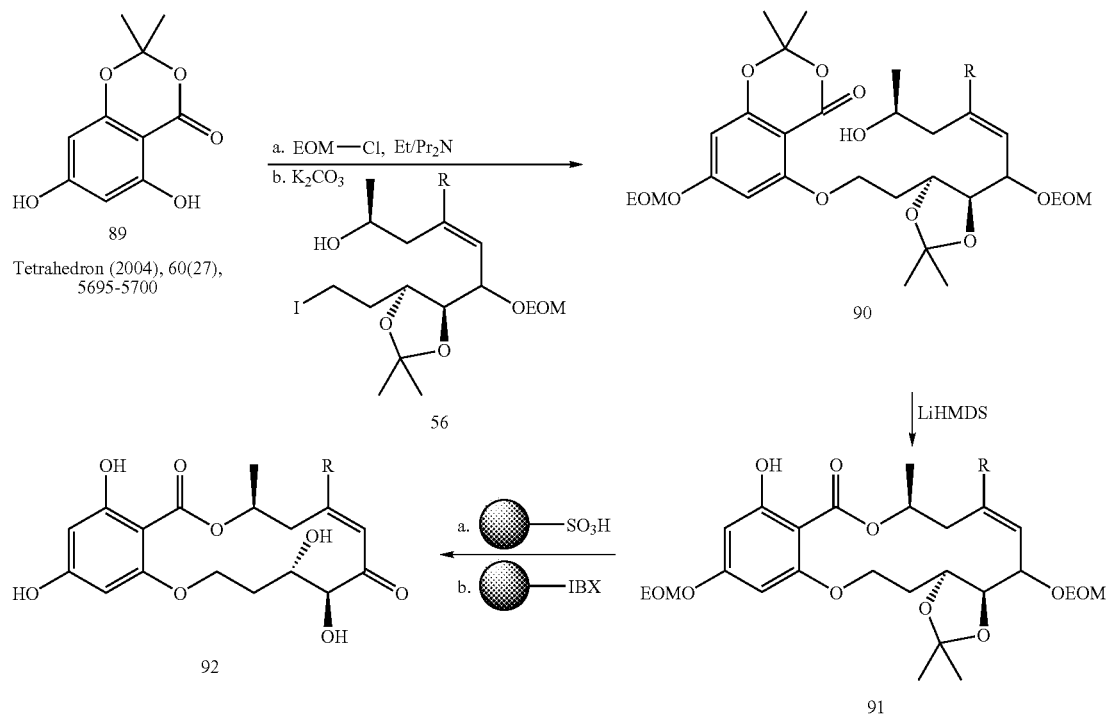

Scheme 14. Synthesis of macrocycles containing an ether group

It will be apparent to one of ordinary skill in the art that any of the schemes shown above describing the formation of certain macrocycles may be modified to prepare alternate radicicol A analogues with different substitution patterns by incorporating different masked enone and aromatic intermediates. For example, the synthetic sequence in scheme 14 above may be modified to alkylate the aromatic intermediate 89 with an alkyl iodide comprising a longer or shorter chain, as described in schemes 8 and 9, to prepare a 15- or 13-membered macrocycle. Similarly, suitably substituted masked enone intermediates such as those described in schemes 6, 7, 10 and 11 may be used.

Biological Activity

Radicicol A and analogues of radicicol A as well as the corresponding allylic alcohol intermediates were tested for its inhibition in a panel of 24 kinase (AKT1, ARK5, Aurora-A, Aurora-B, B-RAF-VE, CDK2/CycA, CDK4/CycD1, CK2-α1, FAK, EPHB4, ERB2, EGF-R, IGF1-R, SRC, VEGF-R2, VEGF-R3, FLT3, INS-R, MET, PDGFR-β, PLK1, SAK, TIE2, COT) at 10 μM. A description of the assay method and the testing results are presented in Example 9.

Significantly, it was found that radicicol A and analogues 3 and 31 exhibited potent inhibitory activity against VEGF-R2, VEGF-R3, FLT3 and PDGFR-β (Table 3). Compounds lacking the cis-enone moiety (allylic alcohols) were not found to have significant activity.

The activity of compound 31 was further evaluated in a panel of 127 kinases using the same method. The results of the assessment in this second panel is shown in FIG. 1. Compound 31 was found to inhibit the activity of VEGF-R2, VEGF-R3, PDGFR-α, PDGFR-β and MEK1 at nanomolar concentrations. It is significant that these enzymes all include a cysteine residue in the active site. Compound 31 inhibited the kinases FLT3, KIT and VEGF-R1 at low mM concentrations. These kinases also include a cysteine at the active site.

Figure 2:
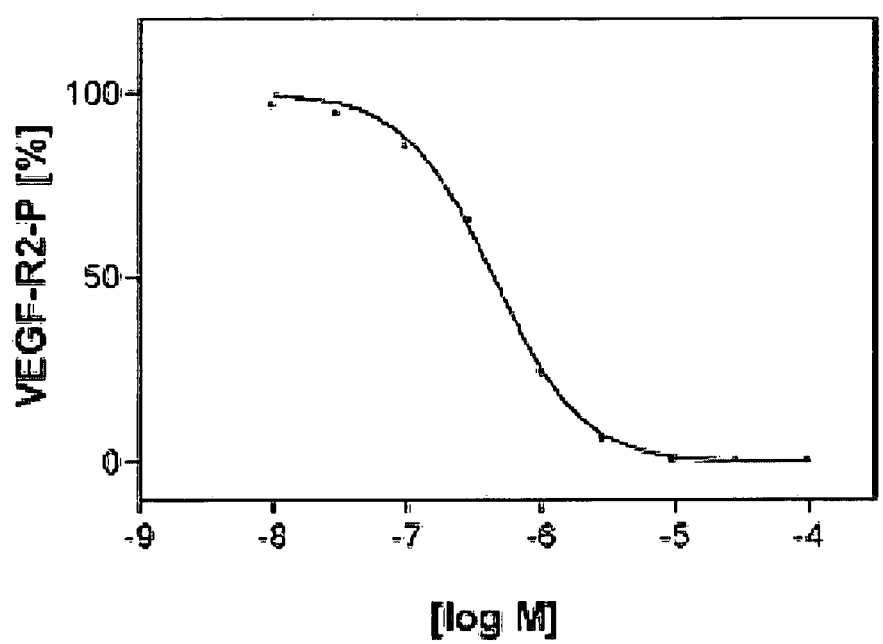
FIG. 2 shows VEGF-R2 autophosphorylation in the presence of compound 31.

The potential efficacy of Compound 31 in vivo was assessed by measuring the level of VEGF-R2 autophosphorylation in the presence of its ligand (VEGF$_{165}$). Thus immortalized HUVECs known to express high levels of VEGF-R2 were incubated with inhibitor 31 for 90 min. and then stimulated with VEGF$_{165}$ for 7 min. The level of autophosphorylation was measured by ELISA using antiVEGF-R2 as capture antibody and anti-phosphotyrosine as detection antibody. Results are expressed as percentage of maximal autophosphorylation in the absence of inhibitor (FIGS. 1 and 2). Compound 31 was found to have a cellular IC$_{50}$ of 440 nM which is consistent with its inhibition at the enzymatic level (90 nM). Consistently, PDGFR-β autophosphorylation was mildly inhibited by 31 (IC$_{50}$=13 μM) whereas autophosphorylation of TIE2 was unaffected.

EXAMPLES

General Techniques. All reactions were carried out under a nitrogen atmosphere with dry solvents under anhydrous conditions, unless otherwise noted. Anhydrous solvents were obtained by passing them through commercially available alumina columns (Innovative technology, Inc., MA). Polymer supported IBX resin was purchased from Novabi°Chem. All fluorous tags, reagents and silica gel were purchased from Fluorous Technologies Inc., PA (www.fluorous.com). Reactions were monitored by thin layer chromatography (TLC) carried out on 0.25 mm E. Merck silica gel plates (60E-254) using UV light as visualizing agent and 10% ethanolic phosphomolybdic acid or vanillin solution and heat as developing agents. E. Merck silica gel (60, particle size 0.040-0.063 mm) was used for flash column chromatography. PTLC (preparative thin layer chromatography) were carried out on 0.25 mm E. Merck silica gel plates. NMR spectra were recorded on Bruker Advance-400 instrument at 400 ($^1$H) and 100 ($^{13}$C)

Example 1

Preparation of Aromatic Intermediates 13, 14 and 15

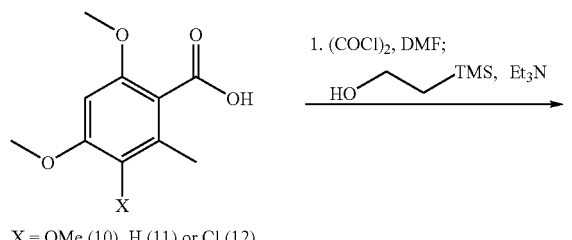

X = OMe (10), H (11) or Cl (12)

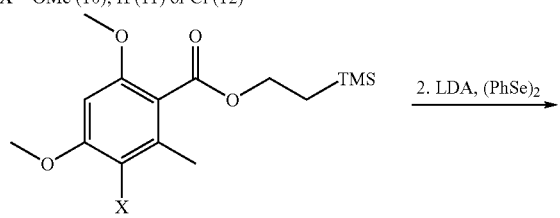

X = OMe (33), H (34) or Cl (35)

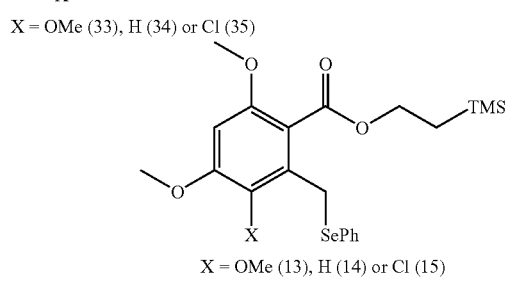

X = OMe (13), H (14) or Cl (15)

Step 1: Preparation of esters 33, 34 and 35. To a solution of acid 10, 11 or 12 (1.0 equiv, 10: 434 mg, 1.92 mmol, 11: 377 mg, 1.92 mmol, or 12: 433 mg, 1.92 mmol), in anhydrous CH$_2$Cl$_2$ (0.23 M, 10 mL) and DMF (cat) at 0° C. was added oxalyl chloride (1.0 equiv, 165 µL, 1.92 mmol) and the reaction was stirred for 1 hour at 23° C. turning progressively golden. Then the reaction was re-cooled to 0° C., and treated sequentially with Et$_3$N (2.6 equiv, 700 µL, 5 mmol), 2-trimethylsilyl ethanol (1.0 equiv, 276 µL, 1.92 mmol) and 4-DMAP (cat). The mixture was allowed to stir for 1 h at 23° C., after which it was diluted with CH$_2$Cl$_2$, washed with sat. NH$_4$Cl$_{aq}$ and dried over MgSO$_4$. Evaporation of the solvents under reduced pressure followed by flash chromatography (SiO$_2$, Hexane to Hexane/EtOAc 4/1 gradient) yielded esters 33 (615 mg, 98%), 34 (551 mg, 97%), and 35 (608 mg, 96%) as colorless solids.

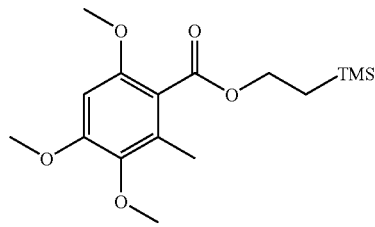

Ester 33: Rf=0.68 (Hexane/EtOAc 2/1); $^1$H NMR (CDCl$_3$, 400 MHz, 25° C.) δ 6.37 (s, 1H), 4.40-4.36 (m, 2H), 3.86 (s, 3H), 3.79 (s, 3H), 3.72 (s, 3H), 2.21 (s, 3H), 1.13-1.09 (m, 2H), 0.06 (s, 9H); $^{13}$C NMR (CDCl$_3$, 100 MHz, 25° C.) δ 168.2, 154.1, 153.2, 141.3, 130.4, 117.2, 95.3, 63.5, 60.54, 56.5, 56.0, 17.6, 12.9, −1.40 (×3); HRMS (MALDI-TOF) m/z 327.1622 ([M+H$^+$], C$_{16}$H$_{26}$O$_5$SiH requires 327.1628).

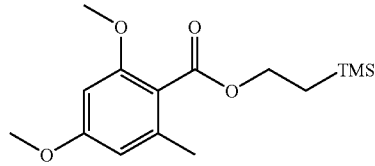

Ester 34: Rf=0.78 (Hexane/EtOAc 2/1); $^1$H NMR (CDCl$_3$, 400 MHz, 25° C.) δ 6.30 (s×2, 2H), 4.40-4.36 (m, 2H), 3.79 (s, 3H), 3.78 (s, 3H), 2.29 (s, 3H), 1.13-1.08 (m, 2H), 0.06 (s, 9H); $^{13}$C NMR (CDCl$_3$, 100 MHz, 25° C.) δ 168.6, 161.3, 158.3, 138.1, 117.2, 106.7, 96.4, 63.3, 55.9, 55.5, 19.9, 17.6, −1.38 (×3); HRMS (MALDI-TOF) m/z 297.1518 ([M+H$^+$], C$_{15}$H$_{24}$O$_4$SiH requires 297.1522).

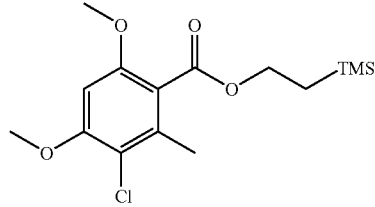

Ester 35: Rf=0.75 (Hexane/EtOAc 2/1); $^1$H NMR (CDCl$_3$, 400 MHz, 25° C.) δ 6.38 (s, 1H), 4.41-4.36 (m, 2H), 3.89 (s, 3H), 3.81 (s, 3H), 2.30 (s, 3H), 1.12-1.10 (m, 2H), 0.06 (s, 9H); $^{13}$C NMR (CDCl$_3$, 100 MHz, 25° C.) δ 167.9, 156.5, 155.8, 135.4, 118.3, 115.0, 94.5, 63.8, 56.4, 56.3, 17.5, 17.4, −1.42 (×3); HRMS (MALDI-TOF) m/z 331.1108 ([M+H$^+$], C$_{15}$H$_{23}$ClO$_4$SiH requires 331.1132).

Step 1: Preparation of selenoethers 13, 14 and 15. A solution of compound 33, 34 or 35 (1.0 equiv, 33: 587 mg, 1.80 mmol, 34: 532 mg, 1.80 mmol, or 35: 595 mg, 1.80 mmol), in anhydrous THF (0.2 M) was treated at −78° C. with freshly made LDA (2.0 equiv, 0.56 M, 6.4 mL, 3.6 mmol). Immediately after, diphenyldiselenide was added (1.0 equiv, 562 mg, 1.80 mmol) and the reaction was stirred at this temperature for 1 hour and quenched by addition of Amberlite resin (20 equiv, ~4.0 mmoUg, 4.5 g, 18 mmol). Upon warming up to room temperature, the reaction was filtered. Evaporation of the solvents under reduced pressure followed by flash chromatography (SiO$_2$, Hexane to Hexane/EtOAc 4/1 gradient)

yielded esters 13 (780 mg, 90%), 14 (778 mg, 91%) and 15 (776 mg, 89%) as colorless solids.

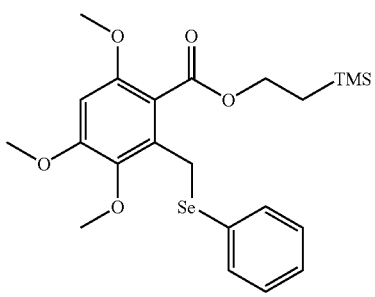

13

Seleno-ether 13: Rf=0.40 (Hexane/EtOAc 3/1); $^1$H NMR (CDCl$_3$, 400 MHz, 25° C.) δ 7.56-7.54 (m, 2H), 7.28-7.25 (m, 3H), 6.44 (s, 1H), 4.35-4.31 (m, 2H), 4.30 (s, 2H), 3.89 (s, 3H), 3.84 (s, 3H), 3.74 (s, 3H), 1.11-1.07 (m, 2H), 0.07 (s, 9H); $^{13}$C NMR (CDCl$_3$, 100 MHz, 25° C.) δ 167.7, 154.6, 154.1, 141.4, 133.5 (×2), 132.2, 132.0, 129.2 (×2), 127.3, 116.4, 97.1, 63.9, 61.0, 56.9, 56.3, 23.7, 17.7, −1.20 (×3); HRMS (MALDI-TOF) m/z 483.1047 ([M+H$^+$], C$_{22}$H$_{30}$O$_5$SeSiH requires 483.1106).

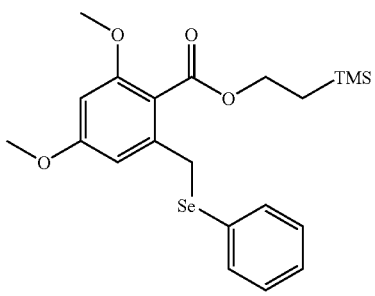

14

Seleno-ether 14: Rf=0.56 (Hexane/EtOAc 3/1); $^1$H NMR (CDCl$_3$, 400 MHz, 25° C.) δ 7.54-7.51 (m, 2H), 7.29-7.26 (m, 3H), 6.36 (d, J=2.4 Hz, 1H), 6.17 (d, J=2.4 Hz, 1H), 4.42-4.38 (m, 2H), 4.14 (s, 2H), 3.82 (s, 3H), 3.69 (s, 3H), 1.17-1.12 (m, 2H), 0.09 (s, 9H); $^{13}$C NMR (CDCl$_3$, 100 MHz, 25° C.) δ 167.8, 161.3, 158.8, 139.8, 134.2 (×2), 130.7, 129.1 (×2), 127.6, 116.1, 106.2, 97.9, 63.6, 56.1, 55.4, 30.4, 17.7, −1.40 (×3); HRMS (MALDI-TOF) m/z 475.0808 ([M+Na$^+$], C$_{21}$H$_{28}$O$_4$SeSiNa requires 475.0820).

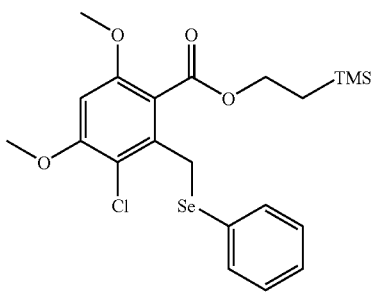

15

Seleno-ether 15: Rf=0.45 (Hexane/EtOAc 3/1); $^1$H NMR (CDCl$_3$, 400 MHz, 25° C.) δ 7.60-7.58 (m, 2H), 7.29-7.27 (m, 3H), 6.44 (s, 1H), 4.35 (s, 2H), 4.30-4.26 (m, 2H), 3.93 (s, 3H), 3.86 (s, 3H), 1.09-1.05 (m, 2H), 0.08 (s, 9H); $^{13}$C NMR (CDCl$_3$, 100 MHz, 25° C.) δ 167.1, 156.9, 156.5, 137.1, 134.2 (×2), 131.0, 129.0 (×2), 127.6, 117.5, 114.9, 95.6, 63.9, 56.5, 56.4, 27.3, 17.5, −1.40 (×3); HRMS (MALDI-TOF) m/z 487.0518 ([M+H$^+$], C$_{21}$H$_{27}$ClO$_4$SeSiH requires 487.0610).

Example 2

Preparation of Aldehyde 17

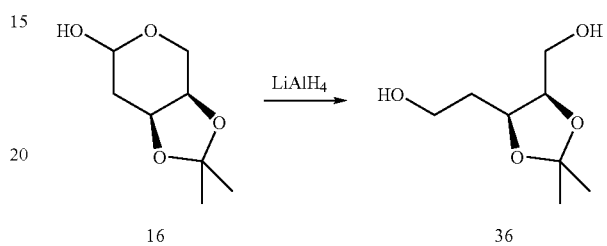

Step 1: Synthesis of diol 36. To a suspension of LiAlH$_4$ (1.4 equiv, 1.20 g, 31.4 mmol) in THF (100 mL) at 0° C. was added drop-wise the protected sugar 16 (1.0 equiv, 3.90 g, 22.4 mmol) in THF (50 mL) and the mixture was stirred for 2 h at 23° C. Then the reaction was quenched by careful addition of H$_2$O (1.2 mL), 15% aqueous NaOH (1.2 mL) and H$_2$O (3.6 mL) and stirred again for 15 minutes. The reaction was diluted with Et$_2$O (100 mL) and the precipitated was filtered through Celite and the solvents were evaporated under reduce pressure. Diol 36 was obtained as a colorless oil (3.75 g, 95%) and was used directly in the next step without further purification. Rf=0.1 (Hexane/EtOAc 1/2); $^1$H NMR (CDCl$_3$, 400 MHz, 25° C.) δ 4.26 (dt, J=7.9, 6.1 Hz, 1H), 4.12 (dt, J=6.1, 6.1 Hz, 1H), 3.75 (dt, J=10.4, 6.1 Hz, 1H), 3.66 (ddt, J=10.9, 5.5, 1.8 Hz, 1H), 3.59 (dd, J=11.6, 5.5 Hz, 1H), 3.53 (dd, J=11.6, 6.7 Hz, 1H), 3.14 (bs, 2H), 1.77-1.73 (m, 2H), 1.38 (s, 3H), 1.29 (s, 3H); $^{13}$C NMR (CDCl$_3$, 100 MHz, 25° C.) δ 108.1, 77.9, 75.5, 61.2, 60.3, 31.5, 28.1, 25.5; HRMS (MALDI-TOF) m/z 177.1139 ([M+H$^+$], C$_8$H$_{16}$O$_4$H requires 177.1127).

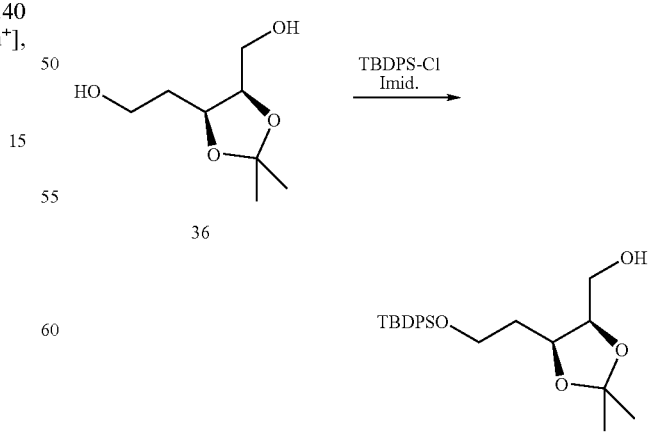

Step 2: TBDPS mono-protected diol 37. To a solution of diol 36 (1.0 equiv, 3.75 g, 21.3 mmol) in DMF (21.3 mL) at 23° C. was added imidazole (1.5 equiv, 2.18 g, 32.0 mmol), the mixture was stirred for 15 minutes, and then TBDPS-Cl (1.0 equiv, 5.54 mL, 21.3 mmol) and the reaction stirred for 2 hours. Then the reaction was diluted with $Et_2O$, washed with 10% $K_2CO_3$, brine, and dried over $Na_2SO_4$. Evaporation of the solvents under reduced pressure followed by flash chromatography ($SiO_2$, Hexane to Hexane/EtOAc 3/1 gradient) afforded TBDPS monoprotected diol 37 (5.82 g, 66%). In the crude NMR the selectivity of the reaction was calculated to be >15:1. Rf=0.25 (Hexane/EtOAc 3/1); $^1$H NMR ($CDCl_3$, 400 MHz, 25° C.) δ 7.68-7.65 (m, 4H), 7.45-7.36 (m, 6H), 4.41 (dt, J=7.3, 5.5 Hz, 1H), 4.16 (dt, J=6.1, 5.0 Hz, 1H), 3.81 (dd, J=7.3, 5.5 Hz, 2H), 3.60 (dd, J=6.7, 5.0 Hz, 2H), 1.84-1.78 (m, 2H), 1.45 (s, 3H), 1.37 (s, 3H), 1.06 (s, 9H), OH signal no visible; $^{13}$C NMR ($CDCl_3$, 100 MHz, 25° C.) δ 135.6 (×2), 135.5 (×2), 133.6, 133.5, 129.6 (×2), 127.7 (×2), 127.6 (×2), 107.9, 77.8, 73.8, 61.8, 61.0, 31.7, 28.2, 26.8 (×3), 25.4, 19.1; HRMS (MALDI-TOF) m/z 437.2113 ([M+Na$^+$], $C_{24}H_{34}O_4SiNa$ requires 437.2124).

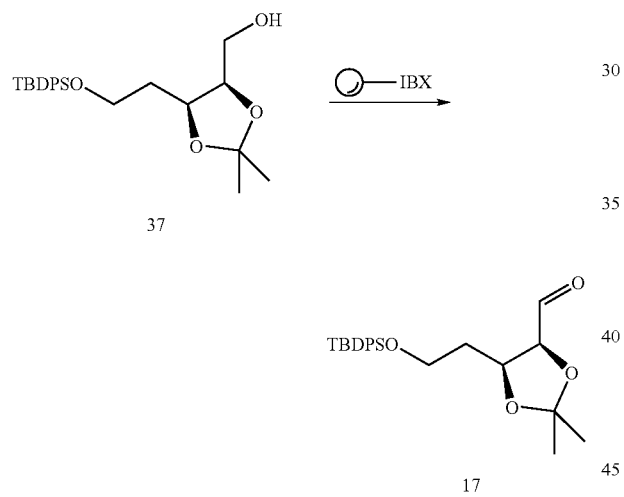

Step 3: Preparation of Aldehyde 17. To a solution of alcohol 37 (1.0 equiv, 1.0 g, 2.4 mmol) in $CH_2Cl_2$ (21.3 mL) at 23° C. was added polymer-bound-IBX (3.0 equiv, 6 g, 1.2 mmoUg, 7.2 mmol) and the suspension was shaken for 2 hours. Then the reaction was filtered and after removal of the solvents under vacuum aldehyde 17 was isolated in quantitative yield (990 mg). Rf=0.45 (Hexane/EtOAc 3/1); $^1$H NMR ($CDCl_3$, 400 MHz, 25° C.) δ 9.68 (d, J=3.0 Hz, 1H), 7.72-7.68 (m, 4H), 7.50-7.40 (m, 6H), 4.69-4.64 (m, 1H), 4.30 (dd, J=7.3, 3.0 Hz, 1H), 3.87-3.84 (m, 2H), 1.99-1.91 (m, 1H), 1.72 (dddd, J=7.5, 5.6, 3.9, 1.9 Hz, 1H), 1.60 (s, 3H), 1.45 (s, 3H), 1.09 (s, 9H); $^{13}$C NMR ($CDCl_3$, 100 MHz, 25° C.) δ 202.1, 135.5 (×2), 135.4 (×2), 133.6, 133.5, 129.7, 129.6, 127.7 (×2), 127.6 (×2), 110.4, 81.8, 75.1, 60.4, 32.3, 27.6, 26.8 (×3), 25.3, 19.2; HRMS (MALDI-TOF) m/z 413.2094 ([M+H$^+$], $C_{24}H_{32}O_4SiH$ requires 413.2148).

Example 3

Preparation of Trans Vinyl Bromide 22

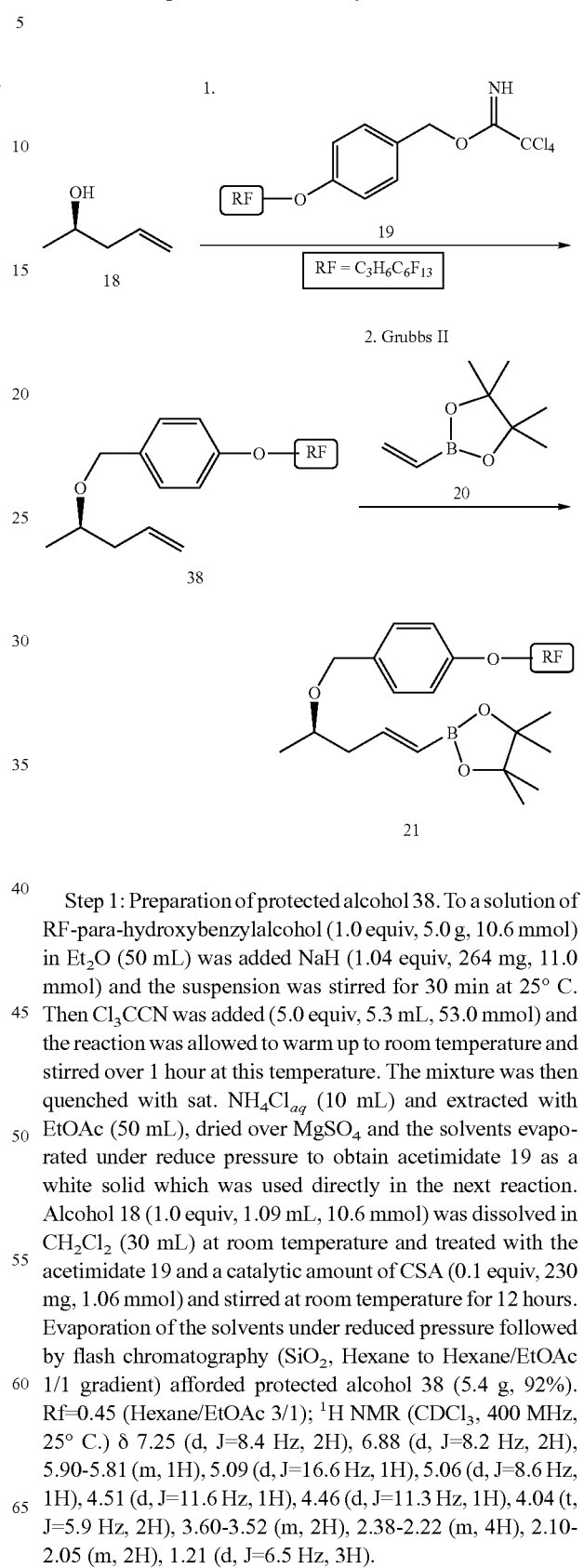

Step 1: Preparation of protected alcohol 38. To a solution of RF-para-hydroxybenzylalcohol (1.0 equiv, 5.0 g, 10.6 mmol) in $Et_2O$ (50 mL) was added NaH (1.04 equiv, 264 mg, 11.0 mmol) and the suspension was stirred for 30 min at 25° C. Then $Cl_3CCN$ was added (5.0 equiv, 5.3 mL, 53.0 mmol) and the reaction was allowed to warm up to room temperature and stirred over 1 hour at this temperature. The mixture was then quenched with sat. $NH_4Cl_{aq}$ (10 mL) and extracted with EtOAc (50 mL), dried over $MgSO_4$ and the solvents evaporated under reduce pressure to obtain acetimidate 19 as a white solid which was used directly in the next reaction. Alcohol 18 (1.0 equiv, 1.09 mL, 10.6 mmol) was dissolved in $CH_2Cl_2$ (30 mL) at room temperature and treated with the acetimidate 19 and a catalytic amount of CSA (0.1 equiv, 230 mg, 1.06 mmol) and stirred at room temperature for 12 hours. Evaporation of the solvents under reduced pressure followed by flash chromatography ($SiO_2$, Hexane to Hexane/EtOAc 1/1 gradient) afforded protected alcohol 38 (5.4 g, 92%). Rf=0.45 (Hexane/EtOAc 3/1); $^1$H NMR ($CDCl_3$, 400 MHz, 25° C.) δ 7.25 (d, J=8.4 Hz, 2H), 6.88 (d, J=8.2 Hz, 2H), 5.90-5.81 (m, 1H), 5.09 (d, J=16.6 Hz, 1H), 5.06 (d, J=8.6 Hz, 1H), 4.51 (d, J=11.6 Hz, 1H), 4.46 (d, J=11.3 Hz, 1H), 4.04 (t, J=5.9 Hz, 2H), 3.60-3.52 (m, 2H), 2.38-2.22 (m, 4H), 2.10-2.05 (m, 2H), 1.21 (d, J=6.5 Hz, 3H).

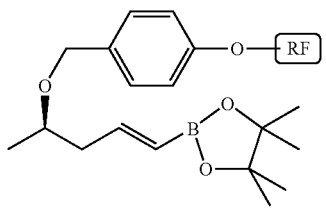

Step 2: Preparation of trans-Borolane 21. To a solution of the terminal alkene 38 (1.0 equiv, 1.5 g, 2.7 mmol) and 4,4,5,5-tetramethyl-2-vinyl-1,2,3-dioxaborolane (1.0 equiv, 460 µL, 2.7 mmol) in degassed toluene (50 mL) warmed up to 80° C. was added Grubbs' II catalyst (2.5 mol %, 57 mg, 0.07 mmol) and the mixture was stirred at this temperature for 12 h. Evaporation of the solvents under reduced pressure followed by fluorous chromatography using 100 g of silica, loading the compound in DMF (1 mL) and eluting with 50% MeOH in H$_2$O (150 mL), then 80% MeOH in H$_2$O (150 mL) and finally 100% MeOH (50 mL) afforded protected borolane 21 (1.7 g, 92%) which eluted at the solvent front in the 100% MeOH. Rf=0.24 (Hexane/EtOAc 3/1); $^1$H NMR (CDCl$_3$, 400 MHz, 25° C.) δ 7.25 (d, J=8.6 Hz, 2H), 6.86 (d, J=8.6 Hz, 2H), 6.61 (dt, J=18.2, 7.0 Hz, 1H), 5.49 (d, J=18.2 Hz, 1H), 4.46 (d, J=11.8 Hz, 1H), 4.42 (d, J=11.3 Hz, 1H), 4.02 (t, J=5.4 Hz, 2H). 3.60 (dq, J=12.4, 5.9 Hz, 1H), 2.50-2.45 (m, 1H), 2.37-2.24 (m, 3H), 2.17-2.05 (m, 2H), 1.26 (s, 12H), 1.19 (d, J=6.4 Hz, 3H); $^{13}$C NMR (CDCl$_3$, 100 MHz, 25° C.) δ 158.3, 150.7, 132.4, 131.8, 129.5 (×2), 120.3, 120-105 (m, C$_6$F$_{13}$) 114.7 (×2), 83.4 (×2), 74.1, 70.2, 66.9, 43.3, 27.8 (t, J$_{CF}$=22.1 Hz), 25.1, 20.0 (×4); HRMS (MALDI-TOF) m/z 701.2203 ([M+Na]$^+$, C$_{27}$H$_{32}$BF$_{13}$O$_4$Na requires 701.2084).

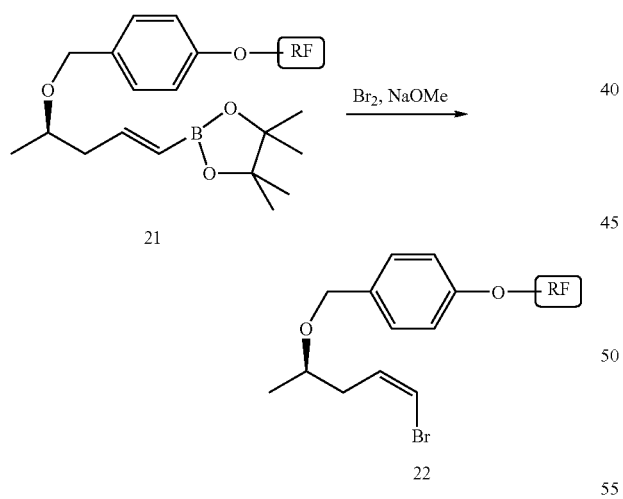

Step 3: Preparation of cis-Bromide 22. A solution of borolane 21 (1.0 equiv, 1.1 g, 1.6 mmol) in Et$_2$O (40 mL) was cooled to −20° C. Then a 1 M bromine solution in CH$_2$Cl$_2$ (1.0 equiv, 1.6 mL, 1.6 mmol) was added over 10 min. After stirring for 15 min, a 3.0 M solution of sodium methoxide in methanol (2.2 equiv, 1.2 mL, 3.52 mmol) was added. The mixture was then stirred 30 min at −20° C. and then brought up to room temperature. The reaction was quenched with benzoic acid resin (20 equiv, 74 mml, 12.4 g), diluted with CH$_2$Cl$_2$ (50 mL), stirred for 2 hours, filtered and washed with CH$_2$Cl$_2$. Evaporation of the solvents under reduced pressure followed by fluorous chromatography using the same conditions as for 21 afforded cis-bromide 22 (898 mg, 89%). Rf=0.76 (Hexane/EtOAc 4/1); $^1$H NMR (CDCl$_3$, 400 MHz, 25° C.) δ 7.27 (d, J=8.6 Hz, 2H), 6.86 (d, J=8.6 Hz, 2H), 6.25-6.19 (m, 2H), 4.50 (d, J=11.6 Hz, 1H), 4.44 (d, J=11.6 Hz, 1H), 4.02 (t, J=5.9 Hz, 2H), 3.67-3.62 (m, 1H), 2.45 (t, J=6.4 Hz, 2H), 2.37-2.24 (m, 2H), 2.12-2.05 (m, 2H), 1.22 (d, J=6.4 Hz, 3H); $^{13}$C NMR (CDCl$_3$, 100 MHz, 25° C.) δ 158.1, 131.3, 131.2, 129.2 (×2), 122-105 (m, C$_6$F$_{13}$), 114.3 (×2), 109.3, 73.2, 66.9, 66.3, 36.5, 27.9 (t, J$_{CF}$=22.1 Hz), 20.5, 19.6; HRMS (MALDI-TOF) m/z 653.0301 ([M+Na$^+$], C$_{21}$H$_{20}$BrF$_{13}$O$_2$Na requires 653.0336).

Example 4

Preparation of Compound 23

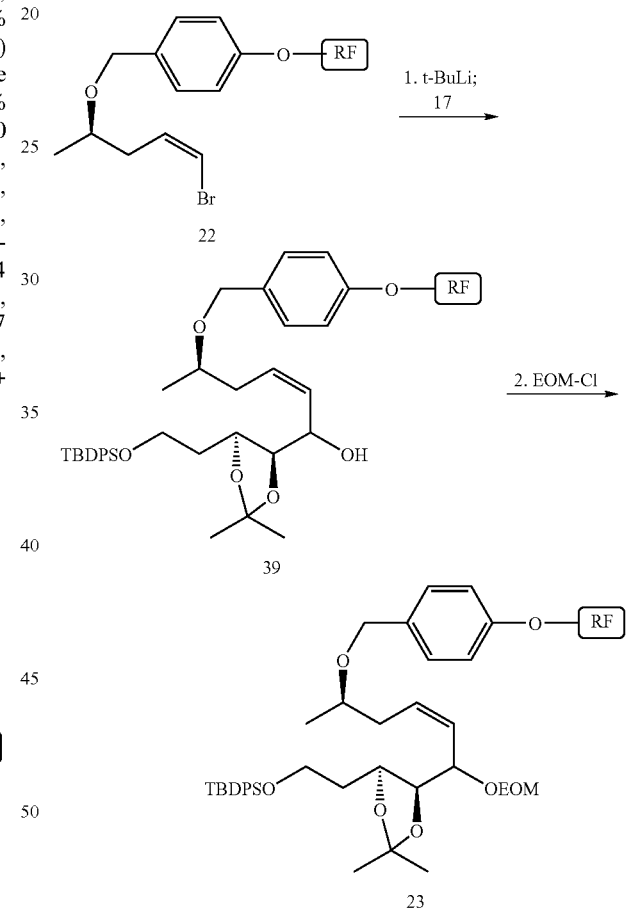

Step 1: Preparation of Alcohol 39. To a solution of cis-bromide 22 (1.0 equiv, 1.5 g, 2.38 mmol) in THF/Et$_2$O 1/1 (15 ml) at −100° C. was carefully added tert-butyllithium (1.0 equiv, 1.4 mL, 1.7 M in pentane). The resulting mixture was stirred for 15 min. Then, a solution of aldehyde 17 (1.0 equiv, 980 mg, 2.38 mmol) in THF/Et$_2$O (5 mL) pre-cooled to −78° C. was added. The resulting mixture was stirred, at −100° C. for 15 min. The reaction was then quenched with benzoic acid resin (10 equiv, 23.8 mmol, 4.0 g), diluted with CH$_2$Cl$_2$ (50 mL), stirred for 1 hr then filtered, washed with brine, and dried over Na$_2$SO$_4$. Evaporation of the solvents under reduced pressure followed by fluorous chromatography using the same conditions as for 21 afforded secondary alcohol 39 as a mixture of diasteroisomers in a ration 3:1 as a colorless oil (2.0 g, 88%): Rf=0.35 (Hexane/EtOAc 4/1); $^1$H NMR (CDCl$_3$, 400 MHz, 25° C.) δ 7.77-7.71 (m, 8H), 7.49-7.41 (m, 12H), 7.30 (d, J=8.0 Hz, 2H), 7.29 (d, J=8.0 Hz, 2H), 6.89 (d, J=8.0 Hz, 4H), 5.82 (dd, J=11.2, 8.0 Hz, 1H), 5.80-5.68 (m, 2H), 5.62 (dd, J=11.3, 8.0 Hz, 1H), 4.60-4.40 (m, 8H), 4.10-3.97 (m, 6H), 3.92-3.87 (m, 4H), 3.74-3.67 (m, 1H), 3.64-3.59 (m, 1H), 2.60-2.52 (m, 2H), 2.41-2.22 (m, 6H), 2.06-2.15 (m, 4H), 1.85-1.81 (m, 4H), 1.50 (s, 3H), 1.49 (s, 3H), 1.42 (s×2, 6H), 1.27 (d, J=5.9 Hz, 3H), 1.26 (d, J=5.9 Hz, 3H), 1.07 (s, 18H), 2 OH signals no visible; $^{13}$C NMR (CDCl$_3$, 100 MHz, 25° C.) δ 158.3, 158.2, 135.7 (×4), 135.6 (×4), 134.1, 134.0, 133.9, 133.8, 131.0, 130.9, 130.9, 130.6, 129.7, 129.7, 129.6, 129.6, 129.5 (×4), 128.7, 128.6, 127.7 (×4), 127.7 (×4), 121-102 (m×2, C$_6$F$_{13}$), 114.5 (×2), 114.4 (×4), 108.3, 107.8, 80.5, 79.8, 74.5, 74.1, 73.8, 73.7, 73.6, 73.3, 70.3, 70.2, 66.4, 66.3, 61.5, 61.0, 35.5, 34.4, 32.8, 32.6, 28.0 (×2), 28.0 (t×2, J$_{CF}$=21.4 Hz), 25.6, 25.5, 26.9 (×6), 20.6 (×2), 19.5, 19.2 (×2), 18.5; HRMS (MALDI-TOF) m/z 987.3646 ([M+Na$^+$], C$_{45}$H$_{53}$F$_{13}$O$_6$SiNa requires 987.3301).

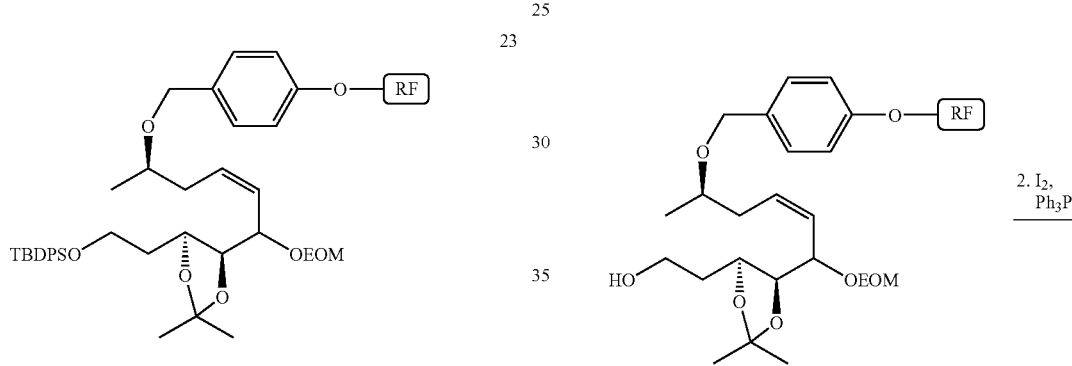

23

Step 2: Preparation of EOM-protected alcohol 23. To a solution of secondary alcohol 39 (1.0 equiv, 2.0 g, 1.93 mmol) in DMF (4 mL) at room temperature were added sequencially tetrabutylammonium iodide (cat), iPr$_2$NEt (8.0 equiv, 2.55 mL, 15.44 mmol) and EOMCI (8.0 equiv, 1.50 mL, 15.44 mmol). The resulting mixture was stirred overnight at 23° C. Then, the reaction was diluted with H$_2$O (2 mL) and loaded directly on the fluorous silica. The column was eluted under the same conditions as for compound 21 to afforded protected alcohol 23 as a mixture of diasteroisomers in a ration 3:1 as a colorless oil (1.96 g, 96%): Rf=0.77 (Hexane/EtOAc 2/1); $^1$H NMR (CDCl$_3$, 400 MHz, 25° C.) δ 7.70-7.68 (m, 8H), 7.41-7.39 (m, 12H), 7.28-7.22 (m, 4H), 6.87 (d, J=8.1 Hz, 4H), 5.85-5.82 (m, 2H), 5.46-5.36 (m, 2H), 4.72-4.64 (m, 3H), 4.53-4.39 (m, 9H), 4.16-4.10 (m, 1H), 4.07-3.99 (m, 1H), 4.01 (t, J=5.4 Hz, 4H), 3.85-3.78 (m, 4H), 3.75-3.67 (m, 2H), 3.61-3.46 (m, 4H), 2.55-2.49 (m, 1H), 2.40-2.28 (m, 7H), 2.11-2.06 (m, 4H), 1.83-1.73 (m, 4H), 1.39 (s, 3H). 1.34 (s, 3H), 1.31 (s, 3H), 1.26 (s, 3H), 1.20-1.17 (m, 12H), 1.04 (s, 9H), 1.03 (s, 9H); $^{13}$C NMR (CDCl$_3$, 100 MHz, 25° C.) δ 157.4, 157.3, 135.6 (×2), 135.6 (×2), 135.5 (×2), 135.5 (×2), 134.0, 133.9, 133.8, 133.8, 132.6, 132.0, 131.3, 130.9, 129.6 (×2), 129.5 (×2), 129.2 (×2), 129.1 (×2), 127.7, 127.7, 127.6 (×4), 127.5 (×4), 122-102 (m×2, C$_6$F$_{13}$), 114.4, 114.4, 114.3, 114.3, 108.4, 107.8, 91.6, 91.5, 79.8, 78.8, 74.3, 74.0, 73.7, 73.4, 70.3, 70.2, 69.9, 69.6, 66.3 (×2), 61.1, 61.0, 61.0, 60.9, 34.8, 34.7, 32.8, 32.5, 28.2, 28.1, 27.8, 27.7, 27.9 (t×2, J$_{CF}$=21.3 Hz), 26.8 (×6), 20.6, 20.5, 19.6, 19.1, 15.3, 15.3 15.0, 14.9; HRMS (MALDI-TOF) m/z 1045.3903 ([M+N$^+$], C$_{48}$H$_{59}$F$_{13}$O$_7$SiNa requires 1045.3720).

Example 5

Preparation of Alkyl Iodide 24

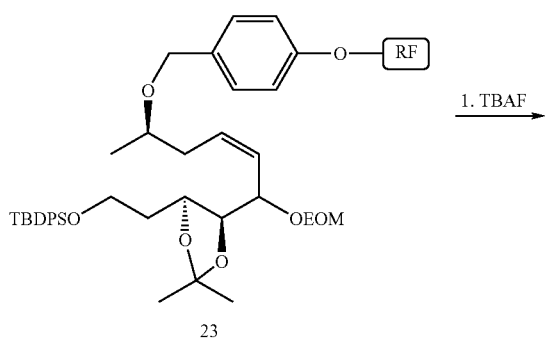

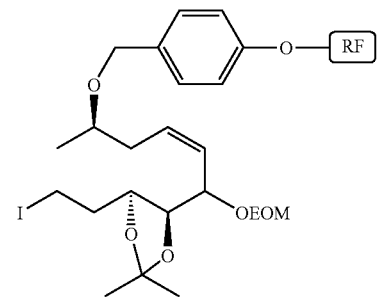

Step 1: Preparation of Alcohol 40. To a solution of alcohol 23 (1.0 equiv, 1.90 g, 1.86 mmol.) in THF (5 mL) at room temperature was added a tetrabutylammonium fluoride solution (2.5 equiv, 4.65 mL, 4.65 mmol, 1.0M in THF). The resulting mixture was stirred for 12 hr then SiO$_2$ (1 g) and benzoic acid resin (5 equiv, 9.3 mmol, 1.55 g) and loaded directly on the fluorous column. The column was eluted as for compound 21 to afforded the primary alcohol 40 (1.38 g, 92%) as a colorless oil: Rf=0.25 (Hexane/EtOAc 2/1); $^1$H NMR (CDCl$_3$, 400 MHz, 25° C.) δ 7.46 (d, J=5.9 Hz, 4H), 7.05 (d, J=5.9 Hz, 4H), 6.0-5.98 (m, 2H), 5.63-5.54 (m, 2H), 4.90 (d, J=8.0 Hz, 1H), 4.89 (d, J=7.5 Hz, 1H), 4.86 (d, J=8.0 Hz, 1H), 4.85 (d, J=7.5 Hz, 1H), 4.74-4.59 (m, 8H), 4.44-4.35 (m, 2H), 4.21 (t, J=5.9 Hz, 4H), 4.02-3.66 (m, 10H), 2.76-2.69 (m, 2H), 2.65-2.43 (m, 6H), 2.31-2.24 (m, 4H), 2.18-1.97 (m, 4H), 1.86-1.83 (m, 2H), 1.69 (s, 3H), 1.61 (s, 3H), 1.57 (s, 3H), 1.52 (s, 3H), 1.41-1.37 (m, 12H); $^{13}$C NMR (CDCl$_3$, 100 MHz, 25° C.) δ 158.1 (×2), 132.8, 132.4, 131.5, 131.5, 129.2 (×4), 127.9, 126.6, 121.9-105.2 (m×2, C$_6$F$_{13}$), 114.39 (×4), 108.6, 108.1, 91.8, 91.6, 80.1, 78.8, 76.7, 76.2, 74.3, 73.9, 70.0, 69.9, 69.5, 69.4, 66.4 (×2), 64.0, 63.2, 61.1, 60.9, 34.9, 34.8, 32.1, 31.9, 27.9, 27.8, 27.7 (t×2, J$_{CF}$=21.3 Hz), 25.7, 25.3, 20.6, 20.5, 19.5, 19.4, 14.8, 14.7; HRMS (MALDI-TOF) m/z 807.2384 ([M+Na$^+$], C$_{32}$H$_{41}$F$_{13}$O$_7$Na requires 807.2542).

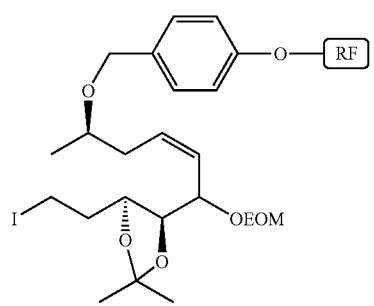

24

Step 2: Preparation of Alkyliodide 24 To a solution of alcohol 40 (1.0 equiv, 1.16 g, 1.47 mmol) in THF (5 mL) were added triphenylphosphine (1.5 equiv, 580 mg, 2.21 mmol) and imidazole (1.5 equiv, 252 mg, 1.84 mmol). The resulting mixture was cooled down to 0° C., followed by the addition of I$_2$ (1.5 equiv, 564 mg, 1.84 mmol). After 1 h at 0° C., the reaction was loaded directly on the fluorous column and eluted as for compound 21 to afford alkyl iodide 24 as a colorless oil (1.20 g, 915): Rf=0.85 (Hexane/EtOAc 2/1); $^1$H NMR (CDCl$_3$, 400 MHz, 25° C.) δ 7.55 (d, J=8.0 Hz, 4H), 7.14 (d, J=8.0 Hz, 4H), 6.16-6.10 (m, 2H), 5.69-5.59 (m, 2H), 4.98 (d, J=7.0 Hz, 1H), 4.96 (d, J=6.5 Hz, 1H), 4.95 (d, J=7.0 Hz, 1H), 4.93 (d, J=6.5 Hz, 1H), 4.81-4.69 (m, 8H), 4.56-4.51 (m, 1H), 4.47-4.43 (m, 1H), 4.37-4.29 (m, 2H), 4.30 (t, J=6.0 Hz, 4H), 4.03-3.75 (m, 6H), 3.67-3.57 (m, 2H), 3.55-3.41 (m, 2H), 2.82-2.67 (m, 2H), 2.69-2.52 (m, 6H), 2.40-2.34 (m, 5H), 2.19-2.11 (m, 1H), 1.73 (s, 3H), 1.66 (s, 3H), 1.65 (s, 3H), 1.60 (s, 3H), 1.54-1.48 (m, 12H); $^{13}$C NMR (CDCl$_3$, 100 MHz, 25° C.) δ 158.2 (×2), 133.2, 132.7, 131.6, 131.6, 129.3 (×2), 129.3 (×2), 127.9, 126.3, 121.0-108.1 (m×2, C$_6$F$_{13}$), 114.5 (×2), 114.4 (×2), 108.9, 108.4, 91.8, 91.7, 79.9, 79.2, 77.4, 76.9, 74.4, 74.0, 70.1, 70.0, 69.2, 69.5, 66.5 (×2), 64.3, 63.4, 35.0, 34.8, 34.3, 34.1, 28.2 (t×2, J$_{CF}$=19.8 Hz), 28.1, 27.8, 25.9, 25.5, 20.7 (×2), 19.8, 19.7, 15.3, 15.2, 3.20, 2.72; HRMS (MALDI-TOF) m/z 917.1313 ([M+Na$^+$], C$_{32}$H$_{40}$F$_{13}$IO$_6$Na requires 917.1559).

Example 6

Preparation of Cyclization Precursors 25, 26 and 27

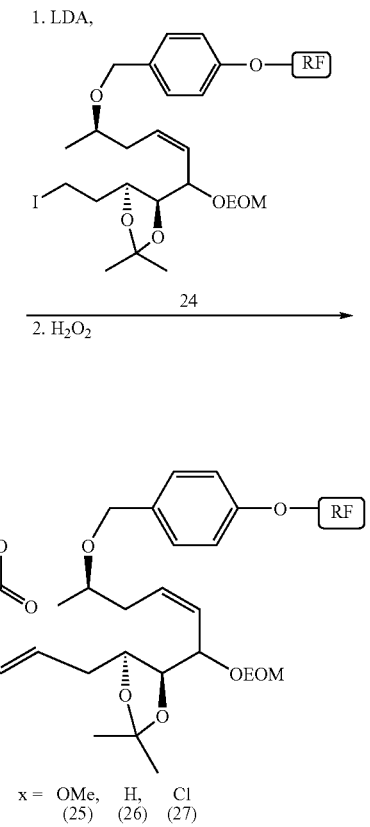

Procedure for alkylation reaction, followed by the oxidation syn-elimination (25, 26 and 27). To a solution of selenoether 13, 14 or 15 (1.0 equiv, 13: 162 mg, 335 μmol, 14: 152 mg, 335 μmol, 15: 163 mg, 335 μmol) in THF/HMPA 10/1 (5.5 mL) cooled at −78° C. was added at once a freshly prepared solution of 0.56 M LDA in THF (2.0 equiv, 1.19 mL, 671 μmol) at −78° C. The mixture immediately turned red. The reaction was stirred 10 min at −78° C. and a solution of the pre-cooled alkyl iodide 24 (1.0 equiv, 300 mg, 336 μmol) in THF (1 mL) was added very slowly along the side of the flask. After stirring at the same temperature for 10 min, the reaction was quenched with benzoic acid resin (5.0 equiv, 1.67 mmol, 280 mg) brought to room temperature and loaded directly on the fluorous silica (20 g) and eluted with 50% MeOH in H$_2$O (30 mL), then 80% MeOH in H$_2$O (30 mL) and finally 100% MeOH (20 mL) to recover corresponding seleno-ethers 25' (377 mg, 90%), 26' (360 mg, 88%) or 27' (385 mg, 91%) as mixtures of 4 diastereoisomers: 25' Rf=0.30 (Hexane/EtOAc 4/1), 26' Rf=0.56 (Hexane/EtOAc 4/1), 27' Rf=0.60 (Hexane/EtOAc 2/1). To a stirred solution of previously prepared seleno-ether 25', 26' or 27' (1.0 equiv, 25': 368 mg, 295 μmol, 26': 360 mg, 295 μmol, 27': 369 mg, 295 μmol) in THF (2 mL) at 23° C. was added H$_2$O$_2$ 35% (2.0 equiv, 50.6 μl, 590 μmol) After 2 h, the reaction was loaded directly on the fluorous silica and eluted as described above to afford compound 25 (249 mg, 82%), 26 (250 mg, 80%) or 27 (233 mg, 79%) as colorless oils:

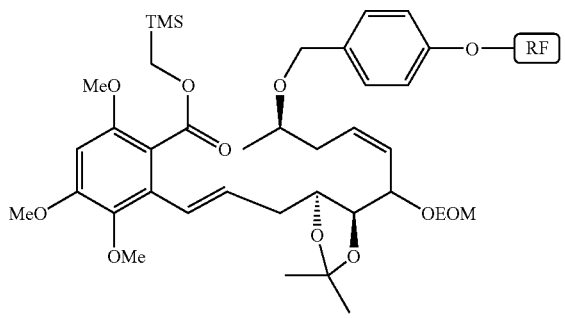

Compound 25: Rf=0.5 (Hexane/EtOAc 2/1); $^1$H NMR (CDCl$_3$, 400 MHz, 25° C.) δ 7.26 (d, J=8.6 Hz, 2H), 7.25 (d, J=8.6 Hz, 2H), 6.85 (d, J=8.6 Hz, 2H), 6.84 (d, J=8.6 Hz, 2H), 6.51 (bd, J=16.1 Hz, 1H), 6.46 (d, J=16.1 Hz, 1H), 6.41 (s×2, 2H), 6.32-6.19 (m, 2H), 5.89-5.79 (m, 2H), 5.42 (dd, J=10.8, 10.8 Hz, 1H), 5.39 (dd, J=9.6, 9.6 Hz, 1H), 4.77-4.65 (m, 4H), 4.55-4.41 (m, 8H), 4.36-4.31 (m, 4H), 4.26-4.21 (m, 2H), 4.08-4.00 (m, 4H), 3.87 (s×2, 6H), 3.80 (s×2, 6H), 3.69 (s, 3H), 3.67 (s, 3H), 3.65-3.47 (m, 6H), 2.56-2.23 (m, 12H), 2.10-2.04 (m, 4H), 1.48 (s, 3H), 1.40 (s, 3H), 1.34 (s, 3H), 1.30 (s, 3H), 1.22-1.18 (m, 12H), 1.10-1.06 (m, 4H), 0.05 (s×2, 18H); $^{13}$C NMR (CDCl$_3$, 100 MHz, 25° C.) δ 169.3, 169.2, 158.3, 158.2, 156.7, 156.1, 154.0, 153.2, 140.8, 140.6, 133.6, 133.2, 132.9, 132.6, 132.4, 132.1, 131.6, 131.6, 129.4, 129.3, 129.3, 129.2, 128.1, 127.8, 125.1, 124.7, 120-110 (m×2, C$_6$F$_{13}$), 117.5, 117.4, 114.5, 114.5, 114.4, 114.4, 108.6, 108.1, 96.3, 93.9, 92.6, 91.9, 79.5, 78.9, 77.4, 77.3, 74.4, 74.1, 70.1, 70.0, 69.8, 69.6, 66.5 (×2), 64.4, 64.2, 63.6, 63.6, 60.6, 60.5, 56.7, 56.6, 56.2, 56.2, 34.8, 34.6, 34.5, 33.9, 29.8 (×2), 29.5 (×2), 28.1 (t×2, J$_{CF}$=20.1 Hz). 20.8, 20.7, 19.7 (×2), 17.4 (×2), 15.3, 15.2, -1.36 (×6); HRMS (MALDI-TOF) m/z 1097.3922 ([M+Na$^+$], C$_{48}$H$_{63}$F$_{13}$O$_{11}$SiNa requires 1097.3881).

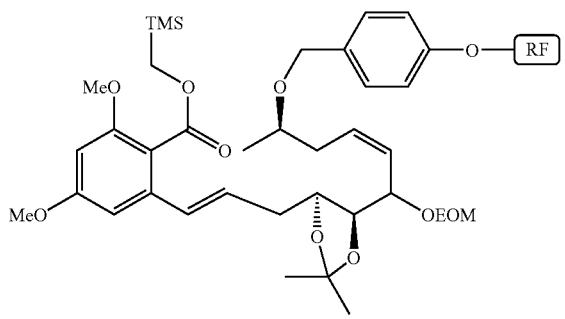

Compound 26: Rf=0.45 (Hexane/EtOAc 4/1); $^1$HNMR (CDCl$_3$, 400 MHz, 25° C.) δ 7.55 (d, J=8.1 Hz, 2H), 7.53 (d, J=8.6 Hz, 2H), 7.13 (d, J=8.6 Hz, 2H), 7.12 (d, J=8.1 Hz, 2H), 6.93 (d, J=2.2 Hz, 1H), 6.90 (d, J=2.2 Hz, 1H), 6.78 (d, J=16.1 Hz, 1H), 6.73 (d, J=16.1 Hz, 1H), 6.63 (bs×2, 2H), 6.61-6.47 (m, 2H), 6.18-6.08 (m, 2H), 5.71 (dd, J=9.7, 9.7 Hz, 1H), 5.68 (dd, J=9.7, 9.7 Hz, 1H), 5.00 (d, J=7.0 Hz, 1H), 4.98 (d, J=7.0 Hz, 1H), 4.96 (d, J=8.6 Hz, 1H), 4.95 (d, J=8.6 Hz, 1H), 4.84-4.64 (m, 8H), 4.57-4.53 (m, 2H), 4.46-4.41 (m, 2H), 4.40-4.36 (m, 2H), 4.30-4.25 (m, 4H), 4.10 (s, 3H), 4.09 (s, 3H), 4.06 (s×2, 6H), 4.04-3.76 (m, 6H), 2.86-2.51 (m, 10H), 2.38-2.32 (m, 6H), 1.78 (s, 3H), 1.71 (s, 3H), 1.70 (s, 3H), 1.65 (s, 3H), 1.56-1.48 (m, 12H), 1.40-1.30 (m, 4H), 0.34 (s, 9H), 0.33 (s, 9H); $^{13}$C NMR (CDCl$_3$, 100 MHz, 25° C.) δ 168.4, 168.3, 161.4 (×2), 158.2 (×2), 158.1 (×2), 137.4, 137.3, 132.5 (×2), 131.6 (×2), 135.5, 130.1, 129.3, 129.2 (×4), 128.7, 128.0, 125.6, 120-110 (m×2, C$_6$F$_{13}$), 116.4 (×2), 114.5 (×2), 114.4 (×2), 108.7, 108.2, 101.7, 101.6, 97.8, 97.7, 91.8, 91.7, 78.9, 78.9, 77.4, 77.0, 74.3, 74.0, 70.1, 70.0, 69.5, 69.4, 66.5 (×2), 64.3, 64.2, 63.5, 63.4, 56.0 (×2), 55.5 (×2), 35.0, 34.8, 33.9, 33.8, 30.4 (×2), 29.8 (×2), 29.7 (×2), 28.1 (t×2, J$_{CF}$=20.1 Hz), 20.7 (×2), 19.7, 19.6, 17.5 (×2), 15.2, 15.1, -1.46 (×6); HRMS (MALDI-TOF) m/z 1083.3813 ([M+Na$^+$], C$_{47}$H$_{61}$F$_{13}$O$_{10}$SiNa requires 1083.3724).

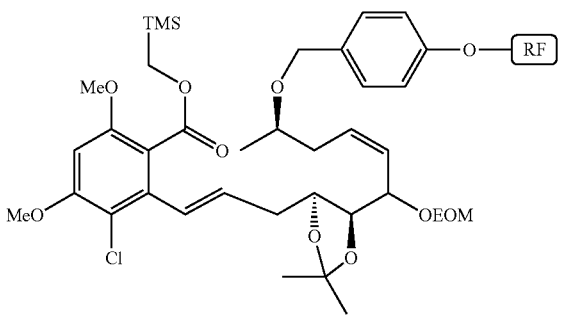

Compound 27: Rf=0.54 (Hexane/EtOAc 2/1); $^1$H NMR (CDCl$_3$, 400 MHz, 25° C.) δ 7.55 (d, J=8.6 Hz, 2H), 7.53 (d, J=8.0 Hz, 2H), 7.13 (d, J=8.6 Hz, 2H), 7.12 (d, J=8.0 Hz, 2H), 6.87 (d, J=16.1 Hz, 1H), 6.81 (d, J=16.1 Hz, 1H), 6.71 (s×2, 2H), 6.40-6.27 (m, 2H), 6.18-6.09 (m, 2H), 5.70 (dd, J=11.3, 11.3 Hz, 1H), 5.68 (dd, J=11.8, 11.8 Hz, 1H), 5.00 (d, J=7.0 Hz, 1H), 4.99 (d, J=7.0 Hz, 1H), 4.97 (d, J=7.0 Hz, 1H), 4.95 (d, J=7.0 Hz, 1H), 4.84-4.68 (m, 8H), 4.64-4.58 (m, 4H), 4.56-4.48 (m, 2H), 4.38-4.28 (m, 4H), 4.18 (s×2, 6H), 4.11 (s×2, 6H), 4.00-3.96 (m, 2H), 3.90-3.85 (m, 2H), 3.81-3.77 (m, 2H), 2.92-2.83 (m, 2H), 2.80-2.67 (m, 4H), 2.65-2.51 (m, 6H), 2.38-2.32 (m, 4H), 1.71 (s, 3H), 1.69 (s, 3H), 1.60 (s, 3H), 1.54 (s, 3H), 1.50-1.47 (m, 12H), 1.37-1.32 (m, 4H), 0.33 (s×2, 18H); $^{13}$C NMR (CDCl$_3$, 100 MHz, 25° C.) δ 167.6, 167.5, 158.1, 158.1, 156.4, 156.3, 155.9, 156.0, 136.2, 136.1, 134.1, 133.7, 132.9, 132.4, 131.6, 131.5, 129.3 (×2), 129.2 (×2), 128.1, 127.3, 127.2, 126.7, 120-110 (m×2, C$_6$F$_{13}$), 117.5, 117.4, 114.5 (×2), 114.4 (×2), 113.7, 113.7, 108.6, 108.2, 95.3 (×2), 91.9, 91.7, 78.9, 78.9, 77.4, 77.0, 74.3, 74.1, 70.1, 69.9, 69.6, 69.4, 66.5 (×2), 64.2 (×2), 63.4, 63.3, 56.5 (×2), 56.3 (×2), 34.9, 34.8, 34.2, 34.1, 30.4 (×2), 29.8, 29.7, 28.1 (t, J$_{CF}$=20.2 Hz), 28.0 (t, J$_{CF}$=21.0 Hz), 20.7, 20.6, 19.7, 19.6, 17.4 (×2), 15.2, 15.1, -1.43 (×6); HRMS (MALDI-TOF) m/z 1117.3356 ([M+Na$^+$], C$_{47}$H$_{60}$ClF$_{13}$O$_{10}$SiNa requires 1117.3334).

Example 7

Mitsunobu Cyclization

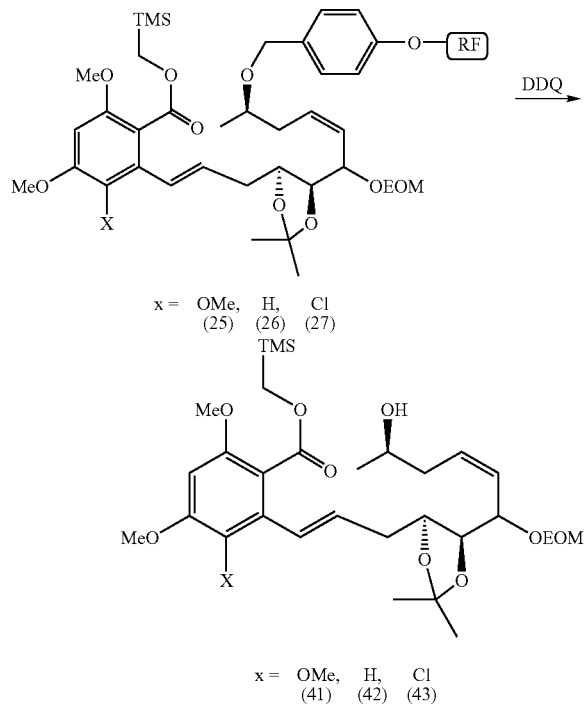

Step 1: PMB de-protection (41, 42 and 43). To a solution of compound 25, 26 or 27 (1.0 equiv, 25: 251 mg, 230 μmmol, 26: 244 mg, 230 μmol, 27: 252 mg, 230 μmol) in CH$_2$Cl$_2$/H$_2$O 2/1 (12 mL) at 23° C. was added DDQ (1.2 equiv, 63 mg, 276 μmol). The reaction mixture was stirred for 2 hours and loaded directly on a fluorous column (20 g) then eluted as described for 25-27 to obtain compound 41-43 in the 80% MeOH fraction with a purity level of ca. 85%. Flash chromatography (SiO$_2$, SiO$_2$, Hexane/EtOAc from 50/1 to 5/1) afforded desired alcohol 41 (111 mg, 77%), 42 (109 mg, 80%) or 43 (101 mg, 70%) as colorless oils:

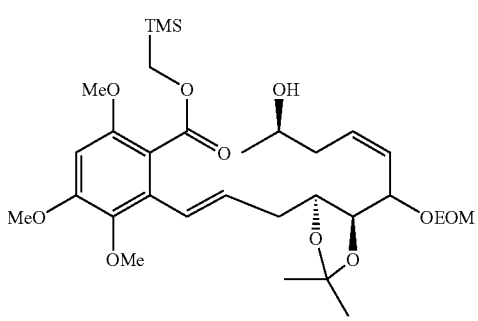

Alcohol 41, less polar major isomer: Rf=0.21 (Hexane/EtOAc 2/1); $^1$H NMR (CDCl$_3$, 400 MHz, 25° C.) δ 6.52 (d, J=16.1 Hz, 1H), 6.41 (s, 1H), 6.27 (dt, J=16.1, 7.0 Hz, 1H), 5.87 (dt, J=10.8, 8.0 Hz, 1H), 5.49 (dd, J=10.8, 10.2 Hz, 1H), 4.74 (d, J=7.0 Hz, 1H), 4.57 (d, J=7.0 Hz, 1H), 4.36-4.32 (m, 2H), 4.27-4.20 (m, 1H), 4.08 (d, J=8.6 Hz, 1H), 4.05 (d, J=8.6 Hz, 1H), 3.87 (s, 3H), 3.84-3.80 (m, 1H), 3.80 (s, 3H), 3.69 (s, 3H), 3.67-3.52 (m, 2H), 2.53-2.47 (m, 2H), 2.33-2.29 (m, 2H), 1.44 (s, 3H), 1.31 (s, 3H), 1.25-1.20 (m, 6H), 1.10-1.06 (m, 2H), 0.05 (s, 9H), 2 OH signals no visible; $^{13}$C NMR (CDCl$_3$, 100 MHz, 25° C.) δ 168.3, 154.0, 153.2, 140.8, 133.3, 132.6, 130.6, 130.3, 125.1, 116.1, 108.5, 96.3, 92.1, 78.5, 77.6, 69.3, 66.8, 64.3, 63.6, 60.5, 56.7, 56.2, 38.0, 34.6, 28.1, 25.9, 23.2, 17.4, 15.0, -1.35 (×3); HRMS (MALDI-TOF) m/z 647.3322 ([M+Na$^+$], C$_{32}$H$_{52}$O$_{10}$SiNa requires 647.3228). More polar minor isomer: Rf=0.20 (Hexane/EtOAc 2/1); $^1$H NMR (CDCl$_3$, 400 MHz, 25° C.) δ 6.47 (d, J=16.1 Hz, 1H), 6.41 (s, 1H), 6.21 (dt, J=16.1, 7.0 Hz, 1H), 5.83 (td, J=10.2, 4.3 Hz, 1H), 5.44 (dd, J=10.2, 10.2 Hz, 1H), 4.73 (d, J=7.0 Hz, 1H), 4.71 (d, J=7.0 Hz, 1H), 4.36-4.32 (m, 2H), 4.27-4.20 (m, 1H), 4.18-4.11 (m, 1H), 3.87 (s, 3H), 3.80 (s, 3H), 3.69 (s, 3H), 3.70-3.69 (m, 2H), 3.67-3.52 (m, 2H), 2.73-2.67 (m, 1H), 2.64-2.60 (m, 1H), 2.48-2.39 (m, 1H), 2.36-2.32 (m, 1H), 1.51 (s, 3H), 1.35 (s, 3H), 1.25-1.21 (m, 6H), 1.10-1.06 (m, 2H), 0.05 (s, 9H), 2 OH signals no visible; $^{13}$C NMR (CDCl$_3$, 100 MHz, 25° C.) δ 168.4, 154.0, 153.2, 140.7, 133.9, 132.9, 130.5, 130.3, 125.2, 116.0, 108.7, 96.4, 92.8, 79.9, 77.3, 70.0, 67.4, 64.4, 63.6, 60.5, 56.6, 56.2, 38.4, 34.5, 28.0, 26.1, 22.6, 17.4, 15.2, -1.35 (×3); HRMS (MALDI-TOF) m/z 647.3169 ([M+Na$^+$], C$_{32}$H$_{52}$O$_{10}$SiNa requires 647.3228).

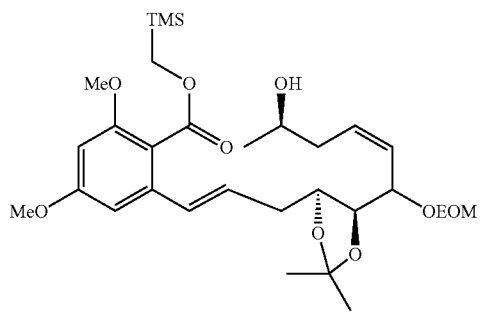

42

Alcohol 42: Rf=0.54 (Hexane/EtOAc 1/1); $^1$H NMR (CDCl$_3$, 400 MHz, 25° C.) δ 6.65 (d, J=2.2 Hz, 1H), 6.61 (d, J=2.2 Hz, 1H), 6.48 (d, J=15.6 Hz, 1H), 6.44 (d, J=16.2 Hz, 1H), 6.34 (s, 1H), 6.33 (s, 1H), 6.31-6.21 (m, 2H), 5.89-5.81 (m, 2H), 5.47 (dd, J=10.8, 10.8 Hz, 1H) 5.45 (dd, J=8.0, 8.0 Hz, 1H), 4.73-4.68 (m, 2H), 4.61-4.55 (m, 2H), 4.39-4.35 (m, 4H), 4.31-4.26 (m, 2H), 4.18-4.08 (m, 4H), 3.82 (s, 3H), 3.81 (S, 3H), 3.77 (s×2, 6H), 3.72-3.64 (m, 3H), 3.59-3.50 (m, 3H), 2.64-2.54 (m, 4H), 2.48-2.45 (m, 4H), 1.46 (s, 3H), 1.42 (s, 3H), 1.37 (s, 3H), 1.33 (s, 3H), 1.20-1.19 (m, 12H), 1.17-1.08 (m, 4H), 0.05 (s, 18H), 2 OH signals no visible; $^{13}$C NMR (CDCl$_3$, 100 MHz, 25° C.) δ 168.4, 168.3, 161.4, 161.3, 158.1, 158.0, 137.4, 137.3, 133.8, 132.7, 130.3, 130.2, 130.0, 129.9, 129.0, 128.9, 116.4 (×2), 116.3 (×2), 108.8, 108.6, 101.7, 101.6, 97.9, 97.8, 92.0, 91.9, 78.9, 78.7, 77.5, 77.1, 69.9, 69.1, 67.3, 66.8, 64.4, 64.3, 63.6, 63.5, 56.0, 56.0, 55.6, 55.5, 38.4, 38.0, 34.0, 33.9, 30.4 (×2), 29.8, 29.7, 17.5 (×2), 15.2, 15.1, -1.38 (×6); HRMS (MALDI-TOF) m/z 647.3080 ([M+Na$^+$], C$_{31}$H$_{50}$O$_{9}$SiNa requires 617.3122).

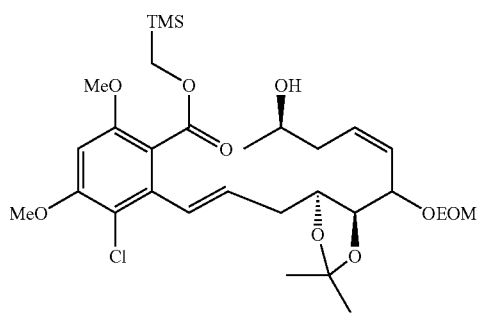

43

Alcohol 43: Rf=0.21 (Hexane/EtOAc 2/1); $^1$H NMR (CDCl$_3$, 400 MHz, 25° C.) δ 6.57 (d, J=16.1 Hz, 1H), 6.52 (d, J=16.1 Hz, 1H), 6.42 (s×2, 2H), 6.10-5.96 (m, 2H), 5.89-5.80 (m, 2H), 5.47 (dd, J=10.8, 10.8 Hz, 1H), 5.42 (dd, J=10.8, 10.8 Hz, 1H), 4.72 (d, J=6.9 Hz, 1H), 4.70 (d, J=7.5 Hz, 1H), 4.58 (d, J=7.5 Hz, 1H), 4.55 (d, J=6.9 Hz, 1H), 4.46 (dd, J=9.7, 9.6 Hz, 1H), 4.37-4.28 (m, 4H), 4.27-4.21 (m, 2H), 4.16 (dd, J=11.8, 5.9 Hz, 1H), 4.09 (dd, J=9.7, 3.8 Hz, 1H), 4.05 (dd, J=8.6, 5.4 Hz, 1H), 3.89 (s×2, 6H), 3.82 (s×2, 6H), 3.74-3.66 (m, 2H), 3.61-3.50 (m, 4H), 2.53-2.43 (m, 4H), 2.31-2.25 (m, 4H), 1.44 (s, 3H), 1.41 (s, 3H), 1.36 (s, 3H), 1.30 (s, 3H), 1.24-1.19 (m, 12H), 1.07-1.02 (m, 4H), 0.04 (s, 18H), 2 OH signals no visible; $^{13}$C NMR (CDCl$_3$, 100 MHz, 25° C.) δ 167.7, 167.6, 156.3, 156.3, 155.9 (×2), 136.3, 136.1, 134.0, 133.9, 133.6, 132.7, 130.3 (×2), 127.4, 127.3, 117.5, 117.4, 113.8, 113.7, 108.8, 108.6, 95.5, 95.4, 92.1 91.9, 79.9, 78.7, 77.5, 76.7, 69.4, 69.2, 67.4, 66.7, 64.3 (×2), 63.7, 63.6, 56.5 (×2), 56.4 (×2), 38.4, 38.0, 34.2, 34.1, 30.4 (×2), 28.1, 28.1, 26.1, 26.0, 17.4 17.3, 15.2, 15.1, −1.39 (×6); HRMS (MALDI-TOF) m/z 651.2772 ([M+Na$^+$], C$_{31}$H$_{49}$ClO$_9$SiNa requires 651.2733).

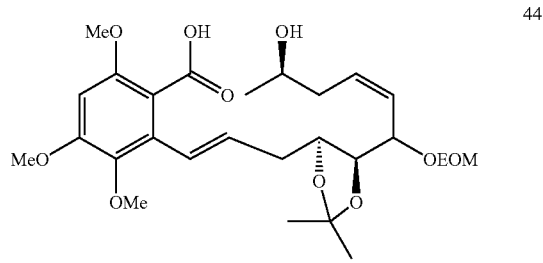

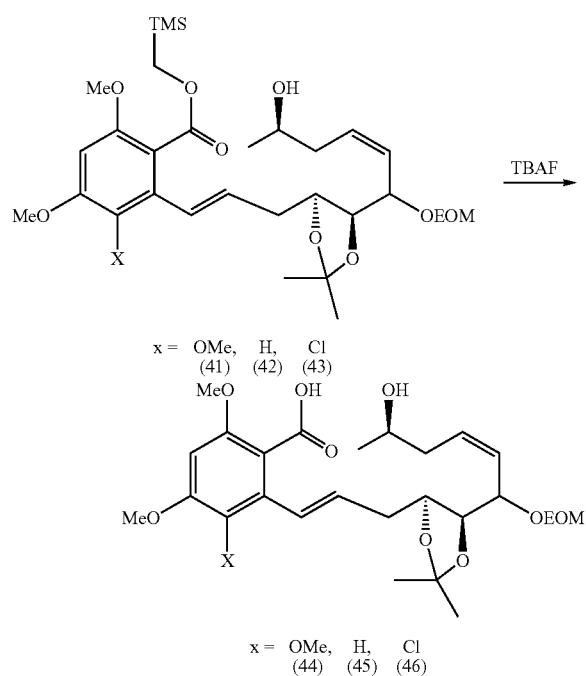

Step 2: Preparation of Acids 44, 45 and 46.

To a solution silyl-ester 41, 42 or 43 (1.0 equiv, 41: 149 mg, 160 μmol, 42: 93 mg, 160 μmol, 43: 99 mg, 160 μmol) in THF (2 mL) at 23° C. a solution of 1M solution of tetra-butyl-ammonium fluoride in TI-IF (3.0 equiv, 480 μl, 480 μmol) was added. The reaction mixture was quenched after 30 min using sat. NH$_4$Cl$_{aq}$, extracted with EtOAc, dried over Na$_2$SO$_4$ and concentrated under reduce pressure. Flash chromatography (SiO$_2$, Hexane/EtOAc from 10/1 to EtOAc/MeOH 50/1) provided desired acid 44 (73 mg, 87%), 45 (69 mg, 87%) or 46 (74 mg, 88%) as colorless oils:

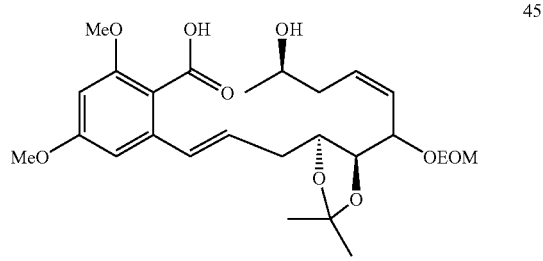

44

Acid 44: Rf=0.50 (EtOAc/MeOH); $^1$H NMR (CO(CD$_3$)$_2$, 400 MHz, 25° C.) δ 6.69 (s×2, 2H), 6.55-6.38 (m, 4H), 5.87-5.81 (m, 2H), 5.45 (dd, J=9.7, 9.7 Hz. 1H), 5.39 (dd, J=10.5, 10.5 Hz, 1H), 4.70 (d, J=6.7 Hz, 1H), 4.63 (d, J=7.0 Hz, 1H), 4.59 (d, J=7.0 Hz, 1H), 4.57 (d, J=6.7 Hz, 1H), 4.27-4.23 (m, 2H), 4.16-4.13 (m, 2H), 4.09-4.01 (m, 2H), 3.88 (s×2, 6H), 3.81 (s×2, 6H) 3.66 (s, 3H), 3.65 (s, 3H), 3.69-3.48 (m, 2H), 3.47-3.42 (m, 4H), 2.63-2.58 (m, 2H), 2.52-2.49 (m, 2H), 2.30 (dd×2, J=5.9, 5.9 Hz, 4H), 1.43 (s, 3H), 1.38 (s, 3H), 1.29 (s, 3H), 1.28 (s, 3H), 1.18-1.13 (m, 12H), 2 OH signals no visible; HRMS (MALDI-TOF) m/z 525.2722 ([M+H$^+$], C$_{27}$H$_{40}$O$_{10}$H requires 525.2700).

45

Acid 45: Rf=0.45 (EtOAc/MeOH); $^1$H NMR (CO(CD$_3$)$_2$, 400 MHz, 25° C.) δ 6.75 (d, J=1.8 Hz, 1H), 6.73 (d, J=1.8 Hz, 1H), 6.64 (d, J=15.8 Hz, 2H), 6.50 (d, J=1.8 Hz, 2H), 6.41 (dt×2, J=15.8, 7.3 Hz, 2H), 5.84 (dt×2, J=10.1, 7.9 Hz, 2H), 5.39 (dd, J=9.7, 9.7 Hz, 1H), 5.38 (dd, J=9.7, 9.7 Hz, 1H), 4.69 (d, J=6.7 Hz, 1H), 4.62 (d, J=9.0 Hz, 1H), 4.60 (d, J=9.0 Hz, 1H), 4.57 (d, J=6.7 Hz, 1H), 4.27 (ddd×2, J=9.6, 3.6, 3.0 Hz, 2H), 4.09 (dd×2, J=8.5, 6.0 Hz, 2H), 3.84 (s×2, 6H), 3.81 (s×2, 6H), 3.81-3.75 (m, 4H), 3.70-3.65 (m, 2H), 3.55-3.47 (m, 2H), 2.66-2.60 (m, 2H), 2.54-2.47 (m, 2H), 2.29 (dd, J=6.7, 6.7 Hz, 4H), 1.38 (s×2, 6H), 1.27 (s×2, 6H), 1.78-1.12 (m, 12H), 2 OH signals no visible; HRMS (MALDI-TOF) m/z 517.2498 ([M+Na$^+$], C$_{26}$H$_{38}$O$_9$Na requires 517.2414).

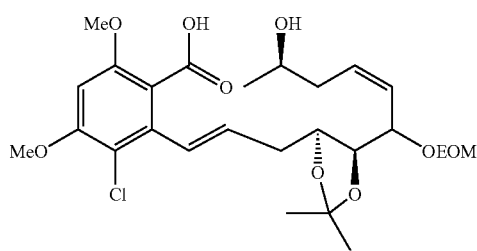

46

Acid 46: Rf. 0.51 (EtOAc/MeOH); $^1$H NMR (CO(CD$_3$)$_2$, 400 MHz, 25° C.) δ 6.78 (s×2, 2H), 6.58 (d, J=16.1 Hz, 1H), 6.56 (d, J=16.1 Hz, 1H), 6.21 (dt, J=16.1, 6.4 Hz, 1H), 6.15 (dt, J=16.1, 6.9 Hz, 1H), 5.87-5.80 (m, 2H), 5.45 (dd, J=9.7, 9.6 Hz, 1H), 5.39 (dd, J=9.7, 9.6 Hz, 1H), 4.70 (d, J=7.0 Hz, 1H), 4.60 (d, J=9.1 Hz, 1H), 4.58 (d, J=9.1 Hz, 1H), 4.57 (d, J=7.0 Hz, 1H), 4.24 (ddd×2, J=9.6, 5.9, 4.3 Hz, 2H), 4.08 (dd×2, J=8.1, 5.9 Hz, 2H), 3.94 (s×2, 6H), 3.87 (s×2, 6H), 3.80-3.76 (m, 4H), 3.72-3.66 (m, 2H), 3.55-3.47 (m, 2H), 2.64 (ddd, J=7.5, 3.7, 1.1 Hz, 1H), 2.61 (ddd, J=7.5, 4.8, 1.1 Hz, 1H), 2.54-2.47 (m, 2H), 2.33-2.29 (m, 4H), 1.42 (s, 3H), 1.37 (s, 3H), 1.29 (s, 3H), 1.28 (s, 3H), 1.18-1.14 (m, 12H), 2 OH signals no visible; HRMS (MALDI-TOF) m/z 551.1950 ([M+Na$^+$], C$_{26}$H$_{37}$ClO$_9$Na requires 551.2024).

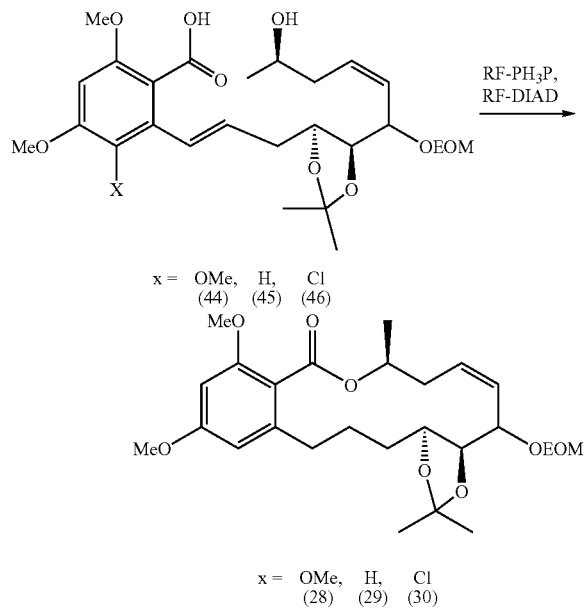

x = OMe, H, Cl
    (44)  (45) (46)

x = OMe, H, Cl
    (28)  (29) (30)

Step 3: Macrocyclization reaction for the synthesis of compounds 28, 29 and 30. A solution of compound 44, 45 or 46 (1.0 equiv, 44: 52 mg, 100 μmol, 45: 50 mg, 100 μmol, 46: 53 mg, 100 μmol) in toluene (10 mL) was treated with fluorous-DIAD (2.0 equiv, 168 mg, 200 mmol) and fluorous-Ph$_3$P (2.0 equiv, 142 mg, 280 mmol) and the mixture was stirred at 23° C. for 2 hours. Then the solvents were evaporated, the crude dissolved in DMF (0.5 mL) and loaded onto a fluorous column (10 g) and eluted as described to a fluorous column and eluted with 50% MeOH in H$_2$O (20 mL), then 80% MeOH in H$_2$O (30 mL) and finally 100% MeOH (20 mL). The desired compounds were recovered in the 80% MeOH fractions with >80% purity: 28 (41 mg, 81%), 29 (38 mg, 80%) or 30 (41 mg, 81%) as white powders.

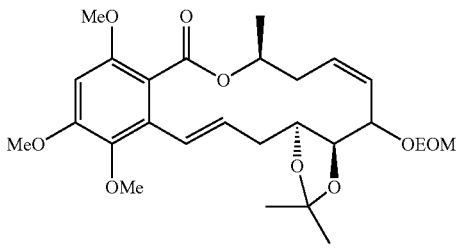

28

Macrocycle 28: Rf=0.44 (Hexane/EtOAc 1/1); $^1$H NMR (CDCl$_3$, 400 MHz, 25° C.) δ 6.62 (d, J=16.4 Hz, 1H), 6.56 (d, J=16.4 Hz, 1H), 6.42 (s, 1H), 6.39 (s, 1H), 6.15 (dt×2, J=15.6, 7.3 Hz, 2H), 5.99-5.87 (m, 2H), 5.69 (dd, J=9.4, 9.4 Hz, 1H), 5.64 (dd, J=10.7, 10.7 Hz, 1H), 5.35-5.29 (m, 2H), 4.75 (dd, J=7.2, 0.8 Hz, 1H), 4.71 (d, J=7.0 Hz. 1H), 4.65 (d, J=7.0 Hz, 1H), 4.63 (d, J=7.2 Hz, 1H), 4.44-4.40 (m, 2H), 4.32-4.30 (m, 2H), 3.87 (s, 3H), 3.86 (s, 3H), 3.80 (s, 3H), 3.79 (s, 3H), 3.78-3.70 (m, 4H), 3.70 (s, 3H), 3.67 (s, 3H), 3.56-3.52 (m, 2H), 3.11 (ddd×2, J=16.1, 11.6, 4.6 Hz, 2H), 2.87-2.53 (m, 6H), 1.42 (s, 3H), 1.37 (s, 3H), 1.33 (s, 3H), 1.31 (s, 3H), 1.18-1.13 (m, 12H); HRMS (MALDI-TOF) m/z 529.2464 ([M+Na$^+$], C$_{27}$H$_{38}$O$_9$Na requires 529.2413).

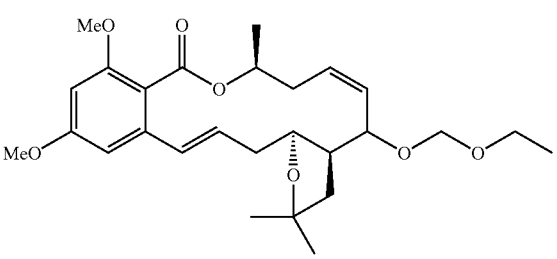

29

Macrocycle 29: Rf=0.25 (Hexane/EtOAc 1/1); $^1$H NMR (CDCl$_3$, 400 MHz, 25° C.) δ 6.63 (d×2, J=15.6 Hz, 2H), 6.48 (s, 1H), 6.47 (s, 1H), 6.37 (s, 1H), 6.35 (s, 1H), 6.23-6.11 (m, 2H), 5.95 (td, J=11.8, 5.4 Hz, 1H), 5.87 (td, J=11.3, 5.9 Hz, 1H), 5.65 (dd, J=9.1, 9.1 Hz, 1H), 5.57 (dd, J=9.7, 9.7 Hz, 1H), 5.39-5.31 (m, 2H), 4.80 (dd, J=7.5, 7.5 Hz, 1H), 4.75-4.73 (m, 1H), 4.70 (d, J=6.4 Hz, 1H), 4.69 (d, J=7.0 Hz, 1H), 4.65 (d, J=6.4 Hz, 1H), 4.64 (d, J=7.0 Hz, 1H), 4.46-4.43 (m, 1H), 4.40-4.36 (m, 1H), 4.34-4.31 (m, 1H), 4.28-4.22 (m, 1H), 3.86 (s, 3H), 3.85 (s, 3H), 3.81 (s, 3H), 3.80 (s, 3H), 3.70-3.64 (m, 2H), 3.60-3.52 (m, 2H), 3.06 (ddd, J=15.1, 11.3, 3.8 Hz, 1H), 2.87-2.74 (m, 1H), 2.67-2.53 (m, 4H), 2.31-2.23 (m, 2H), 1.41 (s, 3H), 1.38 (s, 3H), 1.37 (s, 3H), 1.32 (s, 3H), 1.20-1.14 (m, 12H); $^{13}$C NMR (CDCl$_3$, 100 MHz, 25° C.) δ 166.8, 166.2, 160.5, 160.4, 156.9, 156.9, 137.2, 137.0, 131.0, 130.3, 129.5, 128.9, 128.3 (×2), 128.1, 128.0, 115.2, 115.0, 107.1 (×2), 102.4, 101.8, 96.8, 96.7, 92.1, 91.7, 79.9, 78.2, 76.4, 75.9, 74.9, 74.8, 69.8, 68.5, 62.9, 62.8, 55.1, 55.0, 54.6, 54.5, 34.9, 33.2, 32.6, 32.4, 26.0, 25.7, 24.5, 23.9, 17.2 (×2), 14.2, 14.1; HRMS (MALDI-TOF) m/z 499.2310 ([M+Na$^+$], C$_{26}$H$_{36}$O$_8$Na requires 499.2308).

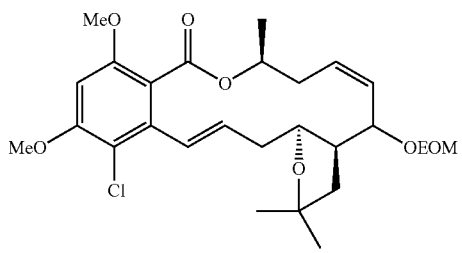

30

Macrocycle 30: Rf=0.20 (Hexane/EtOAc 1/1); $^1$H NMR (CDCl$_3$, 400 MHz, 25° C.) δ 6.61 (d, J=15.8 Hz, 2H), 6.42 (s, 1H), 6.41 (s, 1H), 6.32-6.26 (m, 2H), 6.04-5.94 (m, 2H), 5.70 (dd, J=10.1, 10.1 Hz, 1H), 5.68 (dd, J=10.5, 10.5 Hz, 1H), 5.38-5.33 (m, 2H), 4.73 (d, J=9.0 Hz, 1H), 4.71 (d, J=7.0 Hz, 1H), 4.64 (d, J=9.0 Hz, 1H), 4.62 (d, J=7.0 Hz, 1H), 4.45-4.41 (m, 2H), 4.32 (dd×2, J=6.4, 6.4 Hz, 2H), 3.92 (s, 3H), 3.90 (s, 3H), 3.84 (s, 3H), 3.83 (s, 3H), 3.71-3.64 (m, 2H), 3.57-3.49 (m, 4H), 3.09-3.01 (m, 2H), 2.69-2.61 (m, 2H), 2.31-2.25 (m, 2H), 2.04-2.00 (m, 2H), 1.42 (s, 3H), 1.39 (s, 3H), 1.36 (s, 3H), 1.32 (s, 3H), 1.18-1.13 (m, 12H); $^{13}$C NMR (CDCl$_3$, 100 MHz, 25° C.) δ 167.6, 166.7, 156.4, 156.3, 155.7, 155.0, 136.1, 136.0, 133.6, 132.9, 130.9, 130.3, 129.4, 129.3, 128.0, 127.6, 117.0 (×2), 113.8 (×2), 108.7, 108.1, 95.6, 95.4, 92.5, 92.2, 80.4, 79.3, 77.4, 76.7, 71.3 (×2), 70.3, 69.6, 63.9, 63.7, 56.5, 56.4, 56.4, 56.3, 35.8, 34.9, 33.2, 33.1, 26.6, 26.4, 25.8, 25.1, 18.9 (×2), 15.2, 15.1; HRMS (MALDI-TOF) m/z 533.1922 ([M+Na$^+$], C$_{26}$H$_{35}$ClO$_8$Na requires 533.1918).

Example 8

Formation of Radicicol A and Radicicol A Analogues

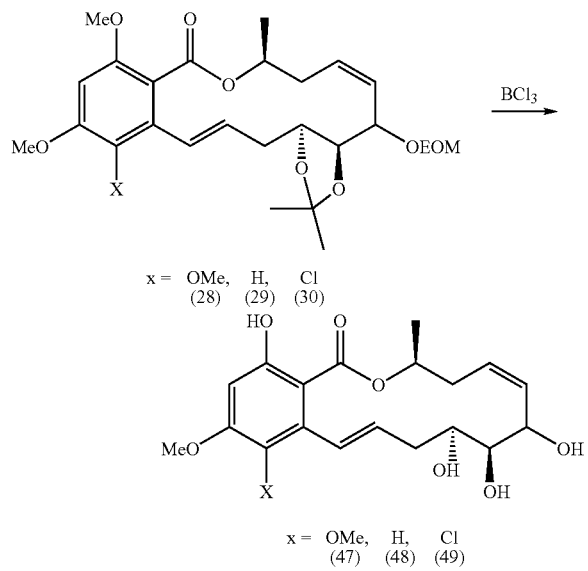

Step 1: deprotection reaction, synthesis of compounds 47, 48 and 49. To a solution of macrocycle 28, 29 or 30 (1.0 equiv, 28: 20 mg, 40 μmol, 29: 19 mg, 40 μmol, 30: 20 mg, 40 μmol) in CH$_2$Cl$_2$ (4.0 mL) at 0° C. was added a 1 M solution of BCl$_3$ in hexane (6 equiv, 240 μL, 240 μmol) and the reaction was monitored by LCMS. The reaction were all complete within 15-30 min. The reaction was then quenched with sat. NaHCO$_{3aq}$. (100 μL) and MeOH (200 μL) stirred for 5 min, further diluted with CH$_2$Cl$_2$ (4.0 mL), filtered through a pad of SiO$_2$ (150 mg) and washed with 20% MeOH in EtOAc. Evaporation of the solvents followed by PTLC (SiO$_2$, 2% MeOH in EtOAc) afforded de-protected compound 47 (14 mg, 88%, as a mixture of two isomers), 48 (12 mg, 82%, 9 mg of the more polar isomer+3 mg of the less polar one) or 49 (14 mg, 86%, 11 mg of the less polar isomer+3 mg of the more polar one) as white powders.

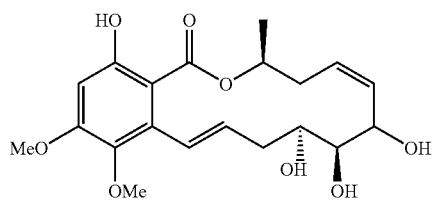

47

Macrocycle 47: Rf=0.20 (EtOAc/MeOH 20/1); $^1$H NMR (CD$_3$OD, 400 MHz, 25° C.) δ 6.77 (d, J=16.6 Hz, 1H), 6.62 (d, J=15.6 Hz, 1H), 6.53 (s×2, 2H), 5.99-5.89 (m, 3H), 5.79 (dd, J=9.6, 9.6 Hz, 1H), 5.73-5.61 (m, 2H), 5.40-5.31 (m, 2H), 4.78 (dd×2, J=8.0, 5.4 Hz, 2H), 4.71-4.64 (m, 2H), 3.93 (s×2, 6H), 3.81 (bd, J=5.4 Hz, 1H), 3.67 (bd, J=6.4 Hz, 1H), 3.63 (s×2, 6H), 3.11-3.03 (m, 1H), 2.97-2.90 (m, 1H), 2.79-2.64 (m, 3H), 2.57-2.49 (m, 1H), 2.46-2.40 (m, 2H), 1.51 (d, J=5.9 Hz, 3H), 1.47 (d, J=5.9 Hz, 3H), 4OH signals no visible; HRMS (MALDI-TOF) m/z 417.1567 ([M+Na$^+$], C$_{20}$H$_{26}$O$_8$Na requires 417.1526).

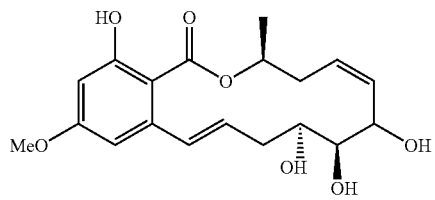

48

Macrocycle 48, more polar major isomer: Rf=0.15 (2% MeOH in EtOAc); $^1$H NMR (CDCl$_3$, 400 MHz, 25° C.) δ 12.35 (s, 1H), 7.20 (dd, J=15.0, 2.2 Hz, 1H), 6.43 (d, J=2.7 Hz, 1H), 6.40 (d, J=2.7 Hz, 1H), 5.86 (ddd, J=11.3, 11.3, 1.6 Hz, 1H), 5.72 (ddd, J=15.0, 11.3, 3.2 Hz, 1H), 5.62 (td, J=11.3, 4.3 Hz, 1H), 5.27-5.20 (m, 1H), 4.99 (d, J=9.6 Hz, 1H), 4.11 (ddd, J=10.8, 5.4, 2.7 Hz, 1H), 3.81 (s, 3H), 3.43 (d, J=2.7 Hz, 1H), 3.06-2.97 (m, 1H), 2.86-2.80 (m, 1H), 2.59-2.50 (m, 1H). 2.30-2.25 (m, 1H), 1.45 (d, I=5.9 Hz, 3H), 3 OH signals no visible; $^{13}$C NMR (CDCl$_3$, 100 MHz, 25° C.) δ 166.4, 164.2, 157.9, 142.7, 133.9, 130.3, 130.1, 128.0, 119.4, 108.5, 100.4, 75.0, 72.5, 72.3, 64.5, 55.6, 39.0, 35.0, 21.6; HRMS (MALDI-TOF) m/z 387.1434 ([M+Na$^+$], C$_{19}$H$_{24}$O$_7$Na requires 387.1420). Less polar minor isomer: Rf=0.28 (2% MeOH in EtOAc); $^1$H NMR (CDCl$_3$, 400 MHz, 25° C.) δ 12.03 (s, 1H), 7.19 (d, J=15.0 Hz, 1H), 6.45 (d, J=2.2 Hz, 1H), 6.41 (d, J=2.2 Hz, 1H), 6.09 (dd, J=11.0 Hz, 8.6 Hz, 1H), 5.99 (dd, J=11.0 Hz, 4.3 Hz, 1H), 5.68 (ddd, J=15.0 Hz, 11.3, 2.7 Hz, 1H), 5.29-5.22 (m, 1H), 4.58-4.53 (m, 1H), 4.10-4.04 (m, 3H), 3.82 (s, 3H), 2.68-2.64 (m, 1H), 2.40-2.34 (m, 1H), 2.31-2.21 (m, 1H), 1.43 (d, J=5.9 Hz, 3H), 3 OH signals no visible; $^{13}$C NMR (CDCl$_3$, 100 MHz, 25° C.) δ 171.4, 166.0, 164.5, 143.1, 134.2, 133.7, 128.7, 127.3, 108.1, 103.4, 100.4, 75.6, 72.6, 72.0, 58.7, 55.6, 47.1, 37.3, 21.6; HRMS (MALDI-TOF) m/z 387.1390 ([M+Na$^+$], C$_{19}$H$_{24}$O$_7$Na requires 387.1420).

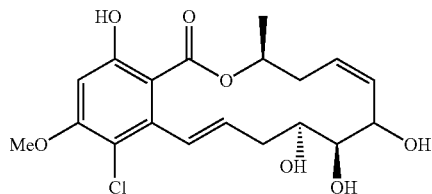

49

Macrocycle 49, less polar major isomer: Rf=0.30 (2% MeOH in EtOAc); $^1$HNMR (CDCl$_3$, 400 MHz, 25° C.) δ 12.20 (s, 1H), 6.52 (dd, J=15.4, 2.4 Hz, 1H), 6.47 (s, 1H), 5.84-5.81 (m, 2H), 5.61 (ddd, J=15.4, 11.0, 3.0 Hz, 1H), 5.50-5.46 (m, 1H), 4.79-4.78 (m, 1H), 4.12 (dd, J=11.0, 5.5 Hz, 1H), 3.91 (s, 3H), 3.68 (bd, J=4.3 Hz, 1H), 2.98-2.89 (m, 2H), 2.66-2.58 (m, 1H), 2.46-2.42 (m, 1H), 1.43 (d, J=6.1 Hz, 3H), 3 OH signals no visible; $^{13}$C NMR (CDCl$_3$, 100 MHz, 25° C.) δ 171.1, 163.9, 160.5, 140.4, 132.7, 132.6, 132.5, 128.6, 125.1, 105.5, 99.8, 77.4, 73.1, 72.3, 71.5, 56.6, 38.6, 33.1, 19.0; HRMS (MALDI-TOF) m/z 421.1101 ([M+Na$^+$], C$_{19}$H$_{23}$ClOC$_7$Na requires 421.1030). More polar minor isomer: Rf=0.25 (2% MeOH in EtOAc); $^1$H NMR (CDCl$_3$, 400 MHz, 25° C.) δ 12.14 (s, 1H), 6.69 (dd, J=15.8, 1.2 Hz, 1H), 6.47 (s, 1H), 5.83-5.78 (m, 1H), 5.66-5.54 (m, 2H), 5.39-5.35 (m, 1H), 4.88 (bd, J=9, 1 Hz, 1H), 4.06-4.02 (m, 1H), 3.49 (s, 3H), 3.35 (bs, 1H), 3.02-2.83 (m, 2H), 2.63-2.50 (m, 1H), 2.31-2.25 (m, 1H), 1.38 (d, J=6.1 Hz, 3H), 3 OH signals no visible; HRMS (MALDI-TOF) m/z 421.1084 ([M+Na$^+$], C$_{19}$H$_{23}$ClO$_7$Na requires 421.1030).

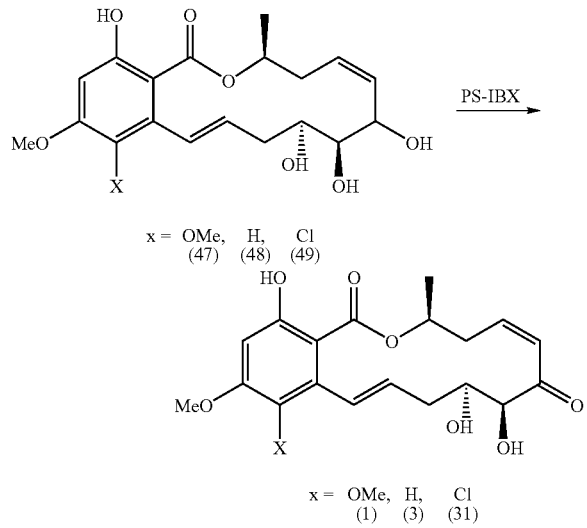

Step 2: Allylic oxidation, synthesis of compounds 1, 3 and 31. To a solution of compound 47, 48 or 49 (1.0 equiv, 47: 10 mg, 25 μmol, 48: 9 mg, 25 μmol, 49: 10 mg, 25 mol, as single isomers or as a mixture) in CH$_2$Cl$_2$ at 23° C. polymer bound IBX resin (3.0 equiv, 1.1 mmolg, 68 mg, 75 μmol) was added. The reactions were monitored by LCMS and found to go to completion within 1 hour without overoxidation of the other alcohols. The reaction were filtered an loaded directly on PTLC (SiO$_2$, 2 or 3% MeOH in EtOAc) to afford de-protected radicicol A (8 mg, 90%), 3 (7 mg, 80%) or 31 (9 mg, 92%).

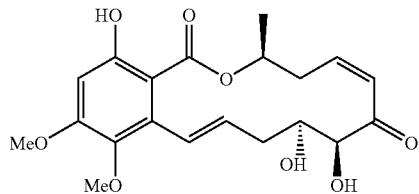

Radicicol A (1)

Radicicol A (1): Rf=0.56 (5% MeOH in EtOAc); $^1$H NMR (CDCl$_3$, 400 MHz, 25° C.) δ 12.07 (s, 1H), 6.46 (dd, J=15.6, 1.3 Hz, 1H), 6.40 (s, 1H), 6.33 (dd, J=11.6, 2.3 Hz, 1H), 6.19 (td, J=11.6, 2.7 Hz, 1H), 6.10 (ddd, J=15.6, 10.5, 3.5 Hz, 1H), 5.36-5.28 (m, 1H), 4.53 (bd, J=2.4 Hz, 1H), 3.97-3.96 (m, 1H), 3.86 (s, 3H), 3.72 (bd, J=5.4 Hz, 1H), 3.55 (s, 3H), 3.41 (dt, J=17.5, 11.3 Hz, 1H), 2.52 (dq, J=17.5, 2.4 Hz, 1H), 2.36-2.29 (m, 1H), 2.06 (ddd, J=16.1, 10.8, 2.2 Hz, 1H), 1.42 (d, J=6.1 Hz, 3H), OH signal no visible; $^{13}$C NMR (CDCl$_3$, 100 MHz, 25° C.) δ 199.4, 171.5, 161.8, 159.0, 146.6, 140.2, 133.5, 132.8, 125.6, 125.2, 103.1, 99.5, 80.9, 73.6, 73.5, 60.2, 55.9, 37.8, 37.0, 20.8; HRMS (MALDI-TOF) m/z 415.1372 ([M+Na$^+$], C$_{20}$H$_{24}$O$_8$Na requires 415.1369).

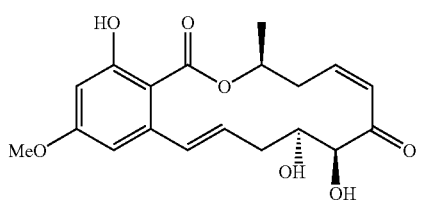

3

Macrocycle 3: Rf=0.44 (3% MeOH in EtOAc); $^1$H NMR (CDCl$_3$, 500 MHz, 25° C.) δ 12.15 (s, 1H), 6.87 (d, J=15.1 Hz, 1H), 6.40 (d, J=2.4 Hz, 1H), 6.38 (d, J=2.4 Hz, 1H), 6.33 (dd, J=11.4, 2.6 Hz, 1H), 6.20 (td, J=11.1, 2.6 Hz, 1H), 5.98 (ddd, J=15.1, 8.4, 4.1 Hz, 1H), 5.27-5.21 (m, 1H), 4.50 (bs, 1H), 4.00-3.98 (m, 1H), 3.81 (s, 3H), 3.58 (dt, J=17.0, 11.3 Hz, 1H), 2.50 (dq, J=17.0, 2.1 Hz, 1H), 2.23-2.19 (m, 1H), 2.13 (ddd, J=15.7, 10.8, 3.0 Hz, 1H), 1.47 (d, J=6.1 Hz, 3H), 2 OH signals no visible; $^{13}$C NMR (CDCl$_3$, 125.75 MHz, 25° C.) δ 199.2, 171.5, 166.1, 164.4, 147.5, 143.1, 132.9, 130.2, 125.3, 108.2, 103.5, 100.4, 80.8, 73.8, 73.7, 55.6, 37.6, 37.2, 20.9; HRMS (MALDI-TOF) m/z 385.1260 ([M+Na$^+$]. C$_{19}$H$_{22}$O$_7$Na requires 385.1264).

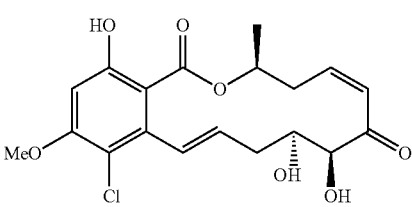

31

Macrocycle 31: Rf=0.60 (2% MeOH in EtOAc); $^1$H NMR (CDCl$_3$, 400 MHz, 25° C.) δ 12.12 (s, 1H), 6.45 (s, 1H), 6.40 (d, J=16.1 Hz, 1H), 6.32 (dd, J=11.3, 2.7 Hz, 1H), 6.18 (td, J=11.3, 2.7 Hz, 1H), 5.83 (ddd, J=16.1, 10.2, 3.2 Hz, 1H), 5.43-5.38 (m, 1H), 4.55 (bs, 1H), 3.96-3.94 (m, 1H), 3.91 (s, 3H), 3.37 (dt, J=17.0, 10.8 Hz, 1H), 2.51 (dm, J=17.0 Hz, 1H), 2.37-2.32 (m, 1H), 2.09 (ddd, J=16.6, 10.8, 1.6 Hz, 1H), 1.39 (d, J=6.5 Hz, 3H), 2 OH signals no visible; $^{13}$C NMR (CDCl$_3$, 100 MHz, 25° C.) δ 199.5, 171.1, 164.4, 163.9, 146.5, 140.1, 134.1, 127.5, 125.8, 114.4, 105.4, 99.7, 81.0, 73.8, 73.1, 56.6, 37.1, 37.1, 21.0; HRMS (MALDI-TOF) m/z 419.0875 ([M+Na$^+$], C$_{19}$H$_{21}$ClO$_7$Na requires 419.0874).

Example 9

Kinase Inhibition of Exemplary Compounds

Radicicol A (1) and analogues 3 and 31 were tested for its inhibition in a panel of 24 kinase (AKT1, ARKS, Aurora-A, Aurora-B, B-RAF-VE, CDK2/CycA, CDK4/CycD1, CK2-α1, FAK, EPHB4, ERB2, EGF-R, IGF1-R, SRC, VEGF-R2, VEGF-R3, FLT3, INS-R, MET, PDGFR-β, PLK1, SAK, TIE2, COT) at 10 µM using the procedure described below.

All protein kinases were expressed in Sf9 insect cells as human recombinant GST-fusion proteins or His-tagged proteins by means of the baculovirus expression system. Kinases were purified by affinity chromatography using either GSH-agarose (Sigma) or Ni-NTH-agarose (Qiagen). The purity of each kinase was checked by SDS-PAGE/silver staining and the identity of each kinase was verified by western blot analysis with kinase specific antibodies or by mass spectroscopy.

Protein Kinase Assay

A radiometric protein kinase assay ($^{33}$PanQinase® Activity Assay) was used for measuring the kinase activity of the 24 protein kinases. All kinase assays were performed in 96-well FlashPlates™ from Perkin Elmer (Boston, Mass., USA) in a 50 µl reaction volume. The reaction cocktail was pipetted in 4 steps in the following order:

20 µl of assay buffer
5 µl of ATP solution (in H$_2$O)
5 µl of test compound (in 10% DMSO)
10 µl of substrate/10 µl of enzyme solution (premixed)

The assay for all enzymes contained 60 mM HEPES-NaOH, pH 7.5, 3 mM MgCl$_2$, 3 mM MnCl$_2$, 3 µM Na-orthovanadate, 1.2 mM DTT, 50 µg/ml PEG$_{20000}$, 1 µM [γ-$^{33}$P]-ATP (approx. 5×10$^{05}$ cpm per well).

For the 24 kinase assays, the amounts of enzyme and substrate were used per well are shown in Table 2 below:

The reaction cocktails were incubated at 30° C. for 80 minutes. The reaction was stopped with 50 µl of 2% (v/v) H$_3$PO$_4$, plates were aspirated and washed two times with 200 µl of 0.9% (w/v) NaCl or 200 µl H$_2$O. Incorporation of $^{33}$P$_i$ was determined with a microplate scintillation counter (Microbeta Trilux, Wallac). All assays were performed with a BeckmanCoulter/Sagian robotic system.

Using the same method described above, compound 31 was evaluated in a panel of 127 kinase enzymes. The results of the evaluation are shown in FIG. 1. The kinases VEGF-R2 AND VEGF-R3, PDGFR-α and PDGFR-β as well as MEK1 where inhibited at nanomolar concentrations. The kinases FLT3, KIT and VEGF-R1 were inhibited at low micromolar concentrations by the compound.

Evaluation of Raw Data

Figure 3:
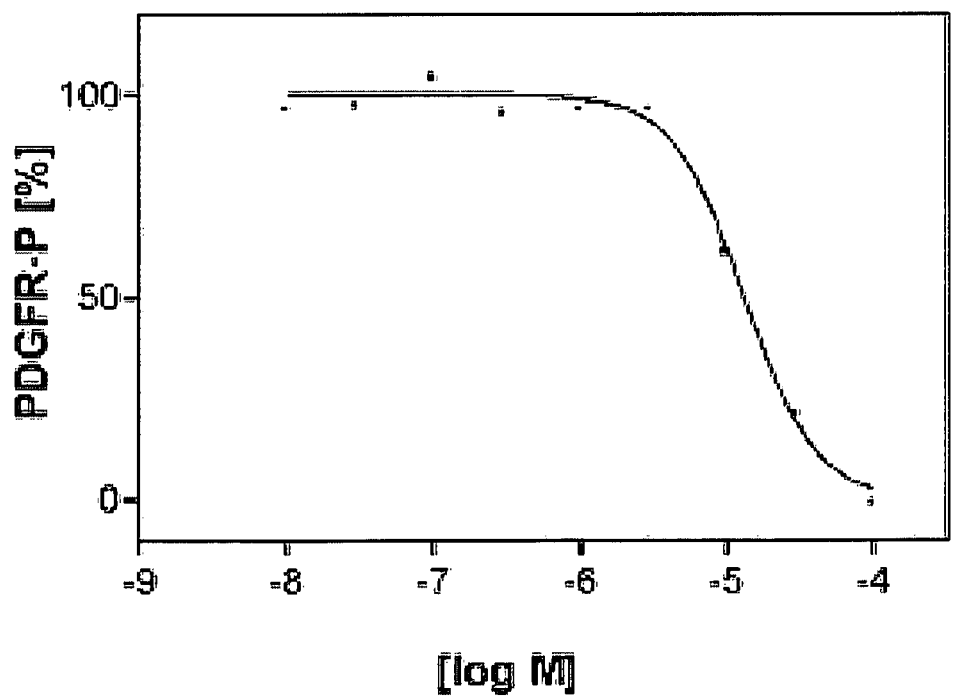
FIG. 3 shows PDGFR-β autophosphorylation in the presence of compound 31.

In agreement with the proposal that the enone moiety acts as a Michael acceptor, none of the products lacking the cis-enone showed significant activity (data not shown). Radicicol A exhibited potent inhibitory activity (low nM) against VEGF-R2, VEGF-R3, FLT3 and PDGFR-β (Table 3). A number of RALs such as pochonins C and D are substituted with a chlorine atom at the 5 position rather than a methoxy, as with analogue 31. Compound 31 was also found to be a potent inhibitor of therapeutically important kinases (Table 3). The activity of this compound was further evaluated in a panel of 127 kinase showing that the kinases inhibited at nM concentrations were VEGF-R2 and 3, PDGFR-α and β as well as MEK1. Kinases inhibited at low µM concentrations included FLT3, KIT and VEGF-R1 which also bear a cysteine in the active site. The potential efficacy of this compound in vivo was then assessed by measuring the level of VEGF-R2 autophosphorylation in the presence of its ligand (VEGF$_{165}$). Thus immortalized HUVECs known to express high levels of VEGF-R2 were incubated with inhibitor 31 for 90 min and then stimulated with VEGF$_{165}$ for 7 min. The level of autophosphorylation was measured by ELISA using antiVEGF-R2 as capture antibody and anti-phosphotyrosine as detection antibody. Results are expressed as percentage of maximal autophosphorylation in the absence of inhibitor (FIG. 3). Compound 31 was found to have a cellular IC$_{50}$ of 440 nM

TABLE 2

| # | Kinase | Kinase Lot # | Kinase ng/50 µl | Substrate | Substrate ng/50 µl |
|---|--------|--------------|-----------------|-----------|--------------------|
| 1 | AKT1 | SP007 | 100 | GSK3(14-27), Lot 005 | 1000 |
| 2 | ARK5 | 002 | 100 | Autosphos. | — |
| 3 | Aurora-A | SP004 | 50 | tetra(LRRWSLG) | 500 |
| 4 | Aurora-B | SP007 | 100 | tetra(LRRWSLG) | 250 |
| 5 | B-RAF-VE | 001 | 20 | MEK1-KM(Lot 013) | 250 |
| 6 | CDK2/CycA | SP005 | 100 | Histone H1 | 125 |
| 7 | CDK4/CycD1 | 006 | 50 | Rb-CTF, Lot 010 | 500 |
| 8 | COT | 017 | 400 | Autophosphorylation | — |
| 9 | EGF-R | SP014 | 25 | Poly(Glu,Tyr)$_{4:1}$ | 125 |
| 10 | EPHB4 | SP006 | 10 | Poly(Glu,Tyr)$_{4:1}$ | 125 |
| 11 | ERBB2 | SP011 | 200 | Poly(Glu,Tyr)$_{4:1}$ | 125 |
| 12 | FAK | SP006 | 100 | Poly(Glu,Tyr)$_{4:1}$ | 125 |
| 13 | IGF1-R | 012 | 20 | Poly(Glu,Tyr)$_{4:1}$ | 125 |
| 14 | SRC | 004 | 10 | Poly(Glu,Tyr)$_{4:1}$ | 125 |
| 15 | VEGF-R2 | 011 | 50 | Poly(Glu,Tyr)$_{4:1}$ | 125 |
| 16 | VEGF-R3 | SP011 | 100 | Poly(Glu,Tyr)$_{4:1}$ | 125 |
| 17 | FLT3 | SP007 | 100 | Poly(Ala,Glu,Lys,Tyr)$_{6:2:5:1}$ | 125 |
| 18 | INS-R | SP005 | 25 | Poly(Ala,Glu,Lys,Tyr)$_{6:2:5:1}$ | 125 |
| 19 | MET | SP011 | 100 | Poly(Ala,Glu,Lys,Tyr)$_{6:2:5:1}$ | 125 |
| 20 | PDGFR-beta | SP012 | 50 | Poly(Ala,Glu,Lys,Tyr)$_{6:2:5:1}$ | 125 |
| 21 | PLK1 | 007 | 50 | Casein | 250 |
| 22 | SAK | 002 | 200 | Autophosphorylation | — |
| 23 | TIE2 | SP006 | 200 | Poly(Glu,Tyr)$_{4:1}$ | 250 |
| 24 | CK2-alpha1 | SP003 | 200 | Casein | 1000 | which is consistent with its inhibition at the enzymatic level (90 nM). Consistently, PDGFR-β autophosphorylation was mildly inhibited by 31 ($IC_{50}$=13 μM) whereas autophosphorylation of TIE2 was unaffected.

TABLE 3

| # | Kinase | Inhibition of Kinases $IC_{50}$ (nM)* | | |
|---|---|---|---|---|
| | | Cmpd 1 | Cmpd 3 | Cmpd 31 |
| 1 | AKT1 | | | |
| 2 | ARK5 | | | |
| 3 | Aurora-A | | | |
| 4 | Aurora-B | | | |
| 5 | B-RAF-VE | | 6300 | |
| 6 | CDK2/CycA | | | |
| 7 | CDK4/CycD1 | | | |
| 8 | COT | | | |
| 9 | EGF-R | | | |
| 10 | EPHB4 | 9100 | | |
| 11 | ERBB2 | | | |
| 12 | FAK | | | |
| 13 | IGF1-R | | | |
| 14 | SRC | 9600 | 9600 | |
| 15 | VEGF-R2 | 26 | 52 | 90 |
| 16 | VEGF-R3 | 66 | 110 | 210 |
| 17 | FLT3 | 110 | 170 | 1800 |
| 18 | INS-R | | | |
| 19 | MET | | | |
| 20 | PDGFR-beta | 210 | 340 | 370 |
| 21 | PLK1 | | | |
| 22 | SAK | | | |
| 23 | TIE2 | | | |
| 24 | CK2-alpha1 | | | |

*empty cells indicate $IC_{50}$ > 100000 nM

Example 10

Level of VEGF-R2 Autophosphorylation in Presence of $VEGF_{165}$

The potential efficacy of compound 31 in vivo was assessed by measuring the level of VEGF-R2 autophosphorylation in the presence of its ligand ($VEGF_{165}$). Thus immortalized HUVECs known to express high levels of VEGF-R2 were incubated with inhibitor 31 for 90 min and then stimulated with $VEGF_{165}$ for 7 min. The level of autophosphorylation was measured by ELISA using antiVEGF-R2 as capture antibody and anti-phosphotyrosine as detection antibody. Results are expressed as percentage of maximal autophosphorylation in the absence of inhibitor (FIG. 2). Compound 31 was found to have a cellular $IC_{50}$ of 440 nM which is consistent with its inhibition at the enzymatic level (90 nM). Consistently, PDGFR-β autophosphorylation was mildly inhibited by 31 ($IC_{50}$=13 μM, FIG. 3) whereas autophosphorylation of TIE2 was unaffected.

The description and examples provided herein are merely illustrative, and the invention is not so limited. Numerous variations, permutations and derivatives of these compounds, procedures and uses will occur to those of ordinary skill in the art, and are contemplated within the scope of the invention.

What is claimed is:

1. A compound of formula I, tautomers thereof, or a pharmaceutically acceptable salt thereof:

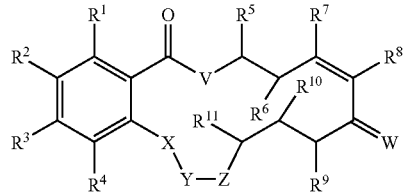

I $R^1$, $R^2$, $R^3$ and $R^4$ are each independently hydrogen, halogen, cyano, —OR, —$NRR^X$, —$NRS(O)R^X$, —$NRS(O)_2R^X$, —SR, —S(O)R, —$S(O)_2R$, —OC(O)R, —C(O)R, —C(O)OR, —$NRC(O)R^X$, —$C(O)NRR^X$, —OC(O)OR, aliphatic, heteroaliphatic, acyl, aryl, heteroaryl, alkylaryl, arylalkyl, alkylheteroaryl or heteroarylalkyl;

$R^5$ is hydrogen, aliphatic, heteroaliphatic, aryl, heteroaryl, alkylaryl, arylalkyl, alkylheteroaryl, or heteroarylalkyl;

$R^6$ is H;

$R^7$ and $R^8$ are each independently hydrogen, halogen, cyano, —OR, —$NRR^X$, —$NRS(O)R^X$, —$NRS(O)_2R^X$, —SR, —S(O)R, —$S(O)_2R$, —OC(O)R, —C(O)R, —C(O)OR, —$NRC(O)R^X$, —$C(O)NRR^X$, —OC(O)OR, aliphatic, heteroaliphatic, aryl, heteroaryl, alkylaryl, arylalkyl, alkylheteroaryl, heteroarylalkyl, or a leaving group;

$R^9$ and $R^{10}$ are each independently hydrogen, azide, —OR, —$NRR^X$, —$NRS(O)R^X$, —$NRS(O)_2R^X$, —SR, —S(O)R, —$S(O)_2R$, —OC(O)R, —C(O)R, —C(O)OR, —$NRC(O)R^X$, —$C(O)NRR^X$, —OC(O)OR, aliphatic, heteroaliphatic, aryl, heteroaryl, alkylaryl or alkylheteroaryl;

$R^{11}$ is hydrogen;

V is O;

W is O;

X is O;

Y is $CH_2$;

Z represents a covalent bond, thereby X—Y—Z, together, forming —O—$CH_2$—; and

R and $R^X$ are independently hydrogen, aliphatic, heteroaliphatic, aryl, arylalkyl, alkylaryl, heteroaryl, alkylheteroaryl, heteroarylalkyl, acyl including acetyl, sulfonyl or a protecting group;

wherein aliphatic, aryl, heteroaryl, alkylaryl, arylalkyl, heteroarylalkyl or alkylheteroaryl are optionally substituted.

2. The compound of claim 1, wherein the compound has the structure of formula II:

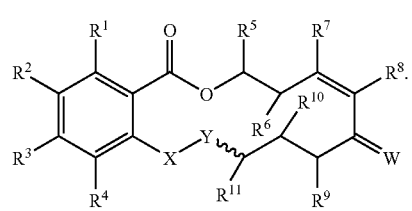

II

3. The compound of claim 1, wherein $R^{10}$ is H, OH or NR.

4. The compound of claim 1, wherein $R^1$ is OH; $R^3$ is OR, NR or halogen; and $R^4$ is H or halogen.

5. The compound of claim 1, wherein $R^1$ is OH and $R^4$ is chloro.

6. The compound of claim 1, wherein $R^1$ is OH and $R^4$ is hydrogen.

7. The compound of claim 1, wherein $R^5$ is H or methyl, $R^7$ is hydrogen, halogen or lower alkyl.

8. The compound of claim 1, wherein $R^5$ is H or methyl, $R^8$ is hydrogen, halogen or lower alkyl.

9. The compound of claim 1, wherein $R^5$ is H or methyl, $R^7$ is lower alkyl, chloro or fluoro; and $R^8$ is hydrogen or fluoro.

10. A pharmaceutical composition comprising an effective kinase-inhibiting amount of a compound of claim 1 in combination with a pharmaceutically acceptable carrier.

11. The composition of claim 10, wherein the composition comprises particles that are less than about 2 microns average particle size.

12. The composition of claim 10, wherein the composition is incorporated into a biodegradable or non-biodegradable polymer.

13. The composition of claim 10, further comprising an additive.

14. The composition of claim 13, wherein the additive is selected from an anti-oxidant, a buffer, a bacteriostat, a liquid carrier, a solute, a suspending agent, a thickening agent, a flavoring agent, a gelatin, glycerin, a binder, a lubricant, an inert diluent, a preservative, a surface active agent, a dispersing agent, a biodegradable polymer, or any combination thereof.

15. The composition of claim 10, wherein the carrier is suitable for oral, parenteral, inhalation, topical, or intradermal administration.

16. The compound of claim 1, wherein the compound has the formula:

| Compound Designation | Structure |
|---|---|
| 104 | 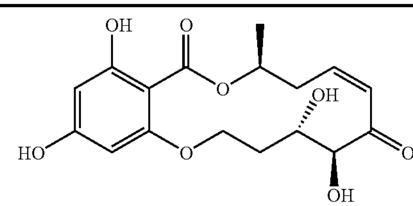 |
| 105 | 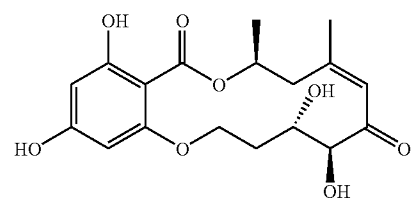 [SMILES: C/C1=C/C(=O)[C@@H](O)[C@@H](O)CCOc2cc(O)cc(O)c2C(=O)O[C@@H](C)C1] |
| 106 | 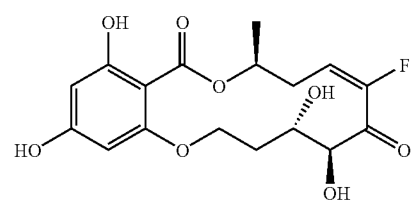 [SMILES: C[C@H]1C/C=C(/F)C(=O)[C@@H](O)[C@@H](O)CCOc2cc(O)cc(O)c2C(=O)O1] |
| or | |
| 118 | 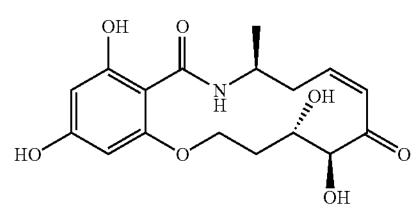 [SMILES: C[C@H]1C/C=C\C(=O)[C@@H](O)[C@@H](O)CCOc2cc(O)cc(O)c2C(=O)N1] |

* * * * *

UNITED STATES PATENT AND TRADEMARK OFFICE
CERTIFICATE OF CORRECTION

PATENT NO. : 8,513,440 B2
APPLICATION NO. : 12/663079
DATED : August 20, 2013
INVENTOR(S) : Nicolas Winssinger et al.

It is certified that error appears in the above-identified patent and that said Letters Patent is hereby corrected as shown below:

In the Specification

Column 7,

Lines 56-67, " 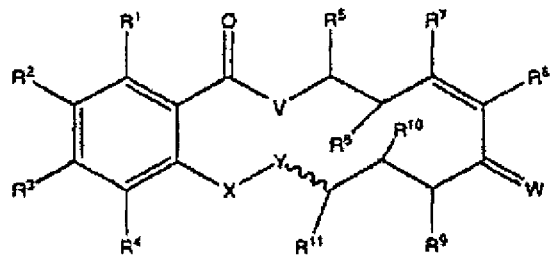 II " should read

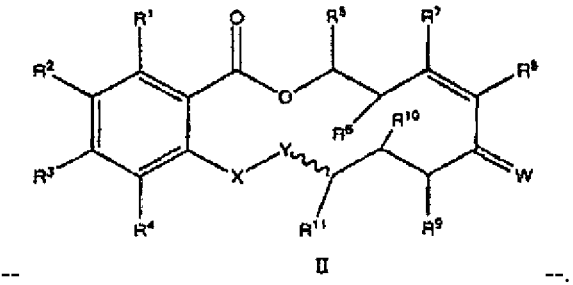

-- II --.

Column 8,
Line 62, "II, IIa or II" should read --II, IIa or III--.

Column 19,
Line 19, "formula IR" should read --formula III--.

Column 33,

Signed and Sealed this
Seventh Day of April, 2015

Michelle K. Lee
*Director of the United States Patent and Trademark Office*

Compound Designation 127, " 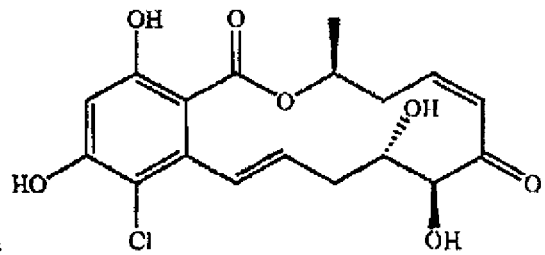 " should read

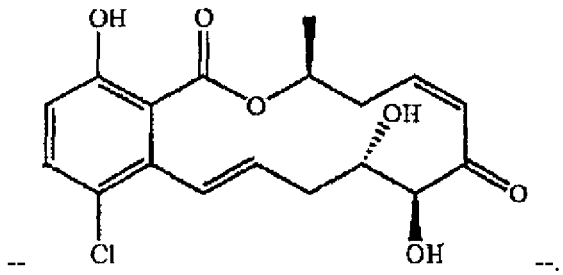
-- --.

Column 39,
Line 66, "is an straight" should read --is a straight--.

Column 46,
Line 2, "have ability to" should read --have the ability to--.

Column 49,
Line 55, "radicicol a analogues" should read --radicicol A analogues--.
Line 56, "provided. neurodegenerative" should read --provided. Neurodegenerative--.

Column 50,
Lines 33-34, "IIb or or" should read --IIb or III, or--.

Column 54,
Line 46, "radicicol analogues" should read --radicicol A analogues--.

Column 60,
Line 16, "Hexamethylphosphotictriamide" should read --Hexamethylphosphorictriamide--.

Column 61,
Line 18, "as it can isomerizes to" should read --as it can isomerize to--.

Column 64,
Line 52, "was remove" should read --was removed--.

Column 65,

Line 7, " 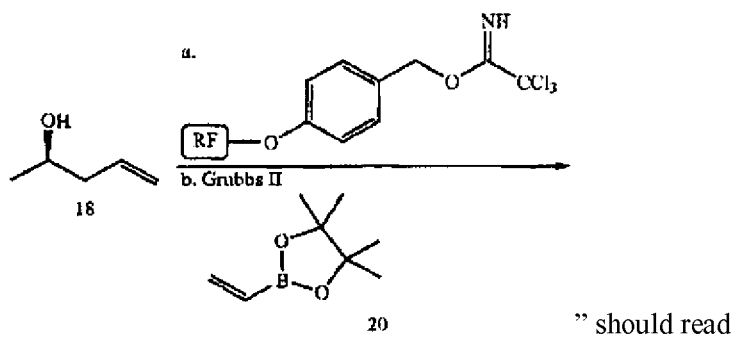 " should read

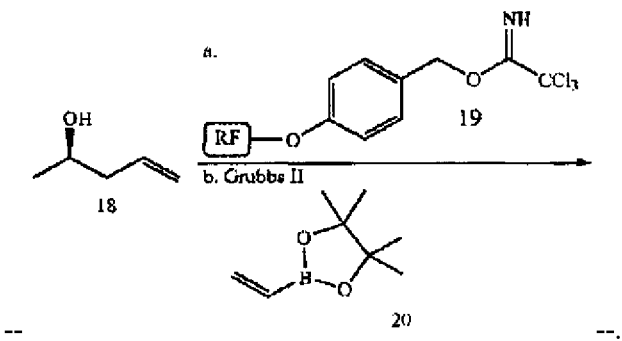 --.

Column 66,

Lines 44-45, " 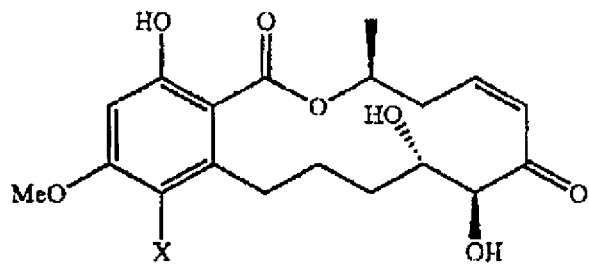 " should read

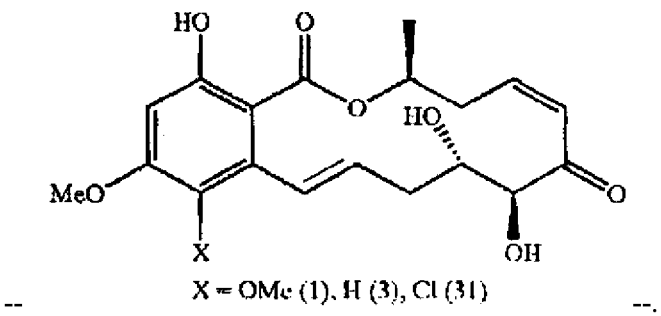 --.

Columns 65-66,
Lines 50-51, "10 min; and then NaOME (2.2 equiv, 1M in CH$_2$Cl$_2$), Et$_2$O, -20° C., 10 min; and then NaOMe (2.2 equiv, 1M in MeOH), -20° C., 30 min, 89%" should read
--10 min; and then NaOMe (2.2 equiv, 1M in MeOH), -20 °C, 30 min, 89%;--.
Line 56, "(trcyclohexyphosphine), TBAF = tetrabutylammonium fluoride," should read
--(tricyclohexylphosphine), HMPA = hexamethylphosphoramide, Imid = imidazole, LDA = lithium diisopropylamide, TBAF = tetrabutylammonium fluoride,--.
Column 75,

CERTIFICATE OF CORRECTION (continued)
U.S. Pat. No. 8,513,440 B2

Lines 61-64, " 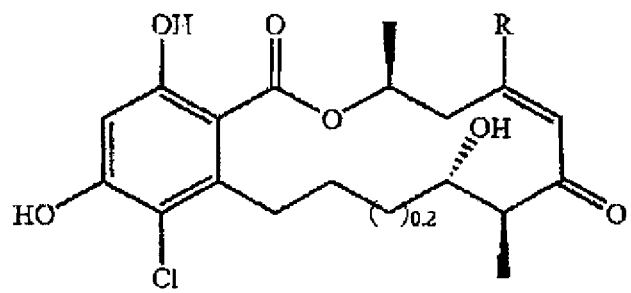 " should read

-- 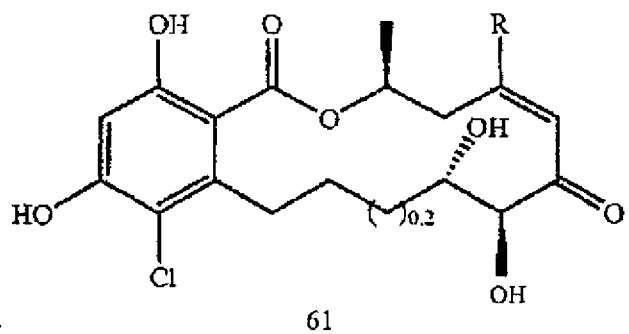 --.

Column 76,

Lines 43-48, " 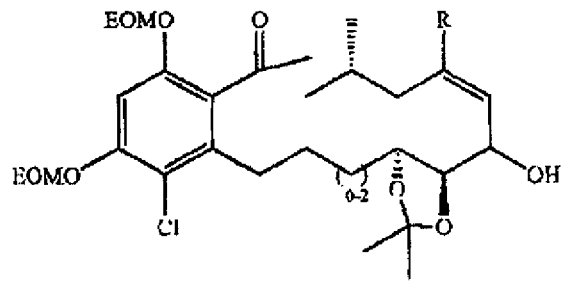 " should read

-- 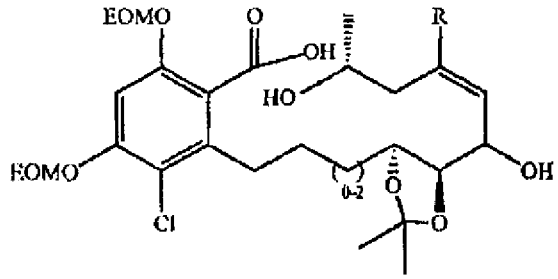 --.

Column 80,

Line 60, "(60E-254)" should read --(60F-254)--.

Column 82,
Line 64, "~4.0 mmoUg," should read --~4.0 mmol/g,--.

Column 84,
Lines 34-35, "under reduce pressure" should read --under reduced pressure--.

Column 85,
Lines 18-19, "signal no visible;" should read --signal not visible;--.
Line 53, "mmoUg" should read --mmol/g--.

Column 86,
Line 51, "under reduce pressure" should read --under reduced pressure--.

Column 87,
Lines 34-35, "([M+Na]$^+$," should read --([M+Na$^+$],--.

Column 89,
Line 14, "signals no visible;" should read --signals not visible;--.

Column 93,
Line 40, "rnlz" should read --$m/z$--.

Column 95,
Line 36, "230 μmmol," should read --230 μmol,--.

Column 96,
Line 5, "signals no visible;" should read --signals not visible;--.
Line 23, "signals no visible;" should read --signals not visible;--.

Column 98,
Line 9, "under reduce pressure" should read --under reduced pressure--.

Column 99,
Line 14, "Rf. 0.51" should read --$Rf$ = 0.51--.

Column 101,
Line 30, "nilz" should read --$m/z$--.
Line 67, "reaction were" should read --reactions were--.

Column 103,

CERTIFICATE OF CORRECTION (continued)
U.S. Pat. No. 8,513,440 B2

Line 60, "25 mol," should read --25 μmol,--.
Line 62, "1.1 mmolg," should read --1.1 mmol/g,--.
Line 65, "reaction were filtered an loaded" should read --reactions were filtered and loaded--.